(12) United States Patent
Sanyal et al.

(10) Patent No.: US 9,334,535 B2
(45) Date of Patent: May 10, 2016

(54) **POLYNUCLEOTIDE SEQUENCES OF *CANDIDA DUBLINIENSIS* AND PROBES FOR DETECTION**

(71) Applicant: JAWAHARLAL NEHRU CENTRE FOR ADVANCED SCIENTIFIC RESEARCH, Bangalore, Karnataka (IN)

(72) Inventors: Kaustuv Sanyal, Karnataka (IN); Sreedevi Padmanabhan, Karnataka (IN); Jitendra Thakur, Karnataka (IN)

(73) Assignee: JAWAHARLAL NEHRU CENTRE FOR ADVANCED SCIENTIFIC RESEARCH, Bangalore, Karnataka (IN)

(*) Notice: Subject to any disclaimer, the term of this patent is extended or adjusted under 35 U.S.C. 154(b) by 38 days.

(21) Appl. No.: 14/248,249

(22) Filed: Apr. 8, 2014

(65) Prior Publication Data

US 2014/0295443 A1    Oct. 2, 2014

Related U.S. Application Data

(63) Continuation of application No. 13/061,937, filed as application No. PCT/IN2008/000760 on Nov. 7, 2008, now abandoned.

(30) Foreign Application Priority Data

Sep. 25, 2008 (IN) ............................ 2341/CHE/2008

(51) Int. Cl.
*C12Q 1/68* (2006.01)
*C07H 21/02* (2006.01)

(52) U.S. Cl.
CPC ............ *C12Q 1/6869* (2013.01); *C12Q 1/6895* (2013.01)

(58) Field of Classification Search
CPC ......................... C12Q 1/6869; C12Q 1/6895
See application file for complete search history.

(56) References Cited

U.S. PATENT DOCUMENTS 6,821,770 B1    11/2004    Hogan
2002/0038015 A1    3/2002    Milliman et al.

FOREIGN PATENT DOCUMENTS

KR    20020033027 A    5/2002
WO    WO 03/097868 A1    11/2003
WO    WO 2007/038578 A1    4/2007

OTHER PUBLICATIONS

New England Bioloabs Catalog, 1998 "Pandom Primers Kit" in two pages.

*Primary Examiner* — Teresa E Strzelecka
(74) *Attorney, Agent, or Firm* — Knobbe, Martens, Olson & Bear, LLP

(57) ABSTRACT

The present invention relates to identification of centromeric sequences of *Candida dubliniensis* and localization of CdCse4p centromeric histone to the identified region. Also the present invention relates to distinguishing *Candida dubliniensis* from other members of genus *Candida*.

18 Claims, 9 Drawing Sheets

SEQUENCE LISTING

```
<160> NUMBER OF SEQ ID NOS: 140

<210> SEQ ID NO 1
<211> LENGTH: 4567
<212> TYPE: DNA
<213> ORGANISM: Candida dubliniensis

<400> SEQUENCE: 1
acaacaatca acaatttctg ctcctcatgc cattacattt acagatagtc atactacaag     60
cctgtcaacc ccatatgaaa aaaaacttc ttacaaacca gttcacgttg caactggcac    120
aactccagca aacataaaca tcccctaaaa aaaagcctac atacatttta aacgcttgac    180
attctcctgc tcaacaaatt caaaagttag ctcatttgcg aataaggtga tacccactta    240
ataaaaacgt acaccttcgg caataaattc ttcttgctta tactcgcctt ttcttaatca    300
gggagatcac ttacatacca caataaacac caagctcttc caaactaaac aaagcaatct    360
cgaaactgac ctctttcttt caataactaa taaacgattt ggaataccca caaagtcaca    420
aattatacag caaaacctcc tacaaaatca atgatatcaa catttcaaac aggaacaaaa    480
gaaaatcgtt tgtatcaatt gattctcttc ctaatacaaa ctaaacacct tgtaattagt    540
tcttataacc aagaataact aaacaataca aaagctacca aatattatca cgtgaccaaa    600
gctaaatgtc ctatctatcc cccctccgaa atcacataaa tctgaacaga tcaggcaaca    660
catgacacct aagttagact tgcaagtagt aatatcggcc aaccatttgg tacttcacac    720
```

```
agcaccaaac taaaacagac tatatgtgaa cgctctacat ttcttacctt tcatgaacac    780
gtcaatccaa ggaatagaat caacattcca cttatgctat gaaacttgac tcttaaaata    840
ctatcacttc cccettacct catgtataca agaagcctta aaaacactat ttcttttca     900
caaatgctgc aatcaactag aattgctaat accccttttt aaacgtgaca cgctcaaaca    960
tacccaccta taaacatcac ataaaaatga aacagcattc actaaagcaa ccataaaacc   1020
gaacacactc ataacttaac taatacactt ccttcatcaa aacactcaat tgctaaaaaa   1080
gaaccaacta atgaaattga ctcaaaacaa aaactaatca gaccgattct ttagataaat   1140
cttagaatgt ccatttcctc acgcaacttt tccatactcc ttgacaatta ttctagtacc   1200
agtacttcgg catgaagaag tctctgatgg tccccggacg tcaactgcaa aaacaaggaa   1260
agtcgcctaa atcttgtaaa gcgctcaact ctttacgaca actcatctct tcgacaagat   1320
caaagaaac gaaacaacg aaaccagta atgctttgcc tatcaataca gaaaaacaaa      1380
cgtcactgtt tcaacaaaag ccacagtcta aaagccttaa atgaacctat tgtgcgttgc   1440
aatttcttta ccattctttc cttgtcttcc taccaaccag tgttaaacca tgcctgtctc   1500
aaaacctcat ttttgaagca tcttctatag taagactctc ctgttttcaca ctaattagct  1560
agacaaaagt tacactttac ttctttatgt atactctgtt gatcagcttc ccattatggt   1620
gatttttcaga aaaaagcga tatataataa ttttttaaac tttcacaata aagaaaatat   1680
tgttttgaca tcacttcaat taaattggct tctagcttta aagttcctca gcttgtagta   1740
aatacccctgc tgttgcctat cactactaa ttcagtcaca ttcctaaagg catttcaata   1800
caacatcatt ccaaagctaa aactataata aactactact ctacaagcgg acggacttgc   1860
tcgggtcaac agctcaaata aattccacaa gtaaatagtat agcatgacaa acatattcat  1920
gaacaccaga atcgggtgca tctaagaagg gttttacttt aatcatagtt ttttagatgc   1980
agcaattggt atcaaggatg tatattggaa ttcaatatac cataagaatt agaccgaaaa   2040
aactacagtt tgactttact cgacacttgc gtatattttc ttagaatatt cagtttgcac   2100
aacaatttaa ttatcaaagc aggattcgtg ctgactatag gtgataaaacc ctactgaggt  2160
caggaaagct aacaagtttt tcctactatc cgtatttgac gggtgcaagg ttatattgta   2220
aaactggtat aacaaaagtg gccctatcag tattgttaat atttagtttg gcaatggtta   2280
acatagttgt atttattgta ttttgattgg gtcaatcgaa acgaacatat gagatgcttc   2340
atttgctttg ctcaacaagt aatcatttca ctgcttaatg cagtatttga ttctatttta   2400
aagaattggg cccgcagagc tgccaaactt agtttacgtc tgtaaaagat tatgtgttga   2460
tttgtatgct agtgtttagg ctcgttgact tttccacata aatactatat tagttcttag   2520
tcattatagc agtcacacag tatcgcattg cgatcttctc ctttcttttg attgtgttga   2580
tgatatgcag aagcttaaaa aactaaatat tcttatcacc cttgtgttga tgcgaagaca   2640
ataattcata ttacttttat agttgggatt tgcaatctca taaacacttt tgattcaagt   2700
taaagaggta atgaagtaag agtctgacta ttggagtagg gaaatggttt tgctgtatt    2760
ggctatattg tttcagttct aacatgagcg tattgatagc agtgtatttg tgatatagga   2820
gactctaggt gccattttgt gcttgttat gtagagaatt actgatgatt gtgtgagggc    2880
atatagatgc actttattga gaatcgatgt tgagaataaa gtaaagtttg ggtagcatta   2940
tcttgttaaa agttgcagtg cattgtacga ggtaagctcc aatgatgatc tggcgaggtt   3000
tatagatatt gctcaagtct gcttgtgtca ggaatgcttc gttttgttgg gatatgattt   3060
```

-continued

```
ccaatgattc tgagcctggt gcagttgggc aacctaaatg aattgatgga ggtgggtttg    3120
aagttgtctc ggatcagttg caagcgatta tttagagatg ccggttatcg tttggtaaaa    3180
gtaagacatg attaacacgg tatgaattga tagcttgtgt aatgcttgta tcgtggaaaa    3240
aaaatgggag gtgaatgagt tttaacaaag tctttgtaat ttataaagtt gaagttcact    3300
gttttatatg tttactgttt tgagactgtt ggaaggtagg ggatacgtta ttgggattta    3360
gtttttggtc tcgccatagt tgttattgtt gttgtcagtt tagtggatgc ttcaaaactg    3420
gaaggactag attgtttggt tttgattgag ttctctttgt gggtactgta ggtttgctat    3480
tgatgatgat tatagaacaa gattttttga caaagagtca aggatgtctt attagtgtac    3540
aagagacgta gtcaggtcaa ggttgattga ttgtagttag gattgctata ttgtattgtt    3600
agaatatttt tttgtccagt tgaaagtgag cactccattgt gatcgattga atagcttata    3660
tttgaaaagg atttgaagac taggactgtt ctgccgagat gattgtgtgt gagagaatat    3720
ggaaggggcg ctgattaaca agtaggctga aaaactatat gttgttgtta gtattggtgg    3780
ggatgaaaga ggaatgaaaa cttcaatacg tggtctcctt cgacgtcaga cgacatgaga    3840
tagagtcagt ggtatatgca aaattgagga aggtttgcca agttaaatag tatatgaaga    3900
tgtttgactg ataatctttc tacagataca aaggtttagt gtcatgattc atgtagatgg    3960
gatatattta tcattgcctc aaagtggatt atcctagtgt gtttgcattt gaagaaatgg    4020
aattagagtt tcttaccagt gggaagtaga aaaagcactt actagatgag acaatttgcg    4080
ctttacttga gtttatagag ttatgagtgc attgcgtgaa tgaatgtcat tgaaatagtc    4140
actcggttgt tggcaattat tggttactat gtgttttcc gatggcagag ttatagtggt    4200
attgtatgaa tgattcaaat ctgtcacgta gtcatgtcaa catggaggga gggttcccca    4260
gacagattga atctgaccgt tagataatat agtaacttag gcttaaccta ttttatattg    4320
gtttagacaa caagaatttg cagaatatat tgatcgcaag cgaagcacga aatgacgctt    4380
agatgtctaa ctaattcccc cattcgttgg gagatttgct acataaatag aatagctgca    4440
cttcccttta ctattatata cttattggat agggtctagc tggttttaga ggacaatgcg    4500
aagtgacaat tcaatttctg gttgctatat tcaattggtg agctatagag cgtatttgag    4560
agataag                                                              4567
```

<210> SEQ ID NO 2
<211> LENGTH: 3168
<212> TYPE: DNA
<213> ORGANISM: Candida dubliniensis

<400> SEQUENCE: 2

```
ttataccccc gaattaacaa gtgcgcccct cctcccataa gtcgtcattg caacataaat     60
gtatgtcttg tctcaaaaca tttcctcttc ctgttcagcc gtaaaatcct aaatccacat    120
tcttatgaga gcctgactat tcatcaatct ggtaaacgaa agcacctgca ctgactacct    180
aaatatactc actctagtca tcataatcaa atacaggact tctcaacatt gacctacaca    240
aactacaaaa cctgttacag gataccagag attgcgttaa aaactcttgc cacattccac    300
aattctaaac ttccgaattt ttagctttcc attgtatcaa gttacaatct taatttcacc    360
cacttgaagt actttaaaat tatacctatt ttgagttcag caattcctta ggatgaaact    420
ttggttgata gtcttgaaat caaatatagt atctatagta tcaatgcctt gaacaaaaag    480
gtatcagacc atctggcaaa accaccattc ttcgcccaaa gagtttgctt ctcatccaac    540
tttattgcca aactatcttt atacgctcag aagcaattaa agctattaaa ctagtggagc    600
```

-continued

```
accaatcatt tcattactcg actatgtggt aactgaataa tatcactcgg tacttagtaa      660
cattgactac tgtacactgc attctcccgg aaaacatatt tcaaggtatt cgatctatat      720
gttttatggg aaaaaatttc cttaagtttg tctttcctgt tcaatgtacc aagaacaaca      780
ttaaattaat tctacctgtt ctgaaatgtg ggagccactc aaagtcagga cctagccttag     840 ttagatgttc tatgtctaaa tcgaagaagt atgtaaacaa gcttctgctg gagacttatt     900
tttcaaaagc tacatctatt tcaatgcac tccgagactg attagaataa ctacattcat      960
ccggatacac cttggcgtat actcaaaacg tcaaacggtt tgtaacattt agcagttaaa    1020
ggttgatcct ccaaacagca gaatgcaaat acatcatatg taagcgctaa atttttatt     1080 caagtggata agtatattg atgttgttct gagaactaca atgtttagtt tgcaattaag    1140
tgagttaggt ttctatttgt atatgtttga gtatgctgct ggctgtttca gagcaattca    1200
gagacttaga atactatata caactacact tcttgtctct ccccatgcca gtgaatatct    1260
gtatcaaagg gttacataat atgcatcctt ctacctatgc atctggtgga tactttgggt    1320
tattcataca atttcagtat gaaaaaatgc atttgtatta ttacctcaat tagcttcaca    1380
gccagtaatc aagtcctcta taggcgtaac acaagatttc ggtattactg gcgatattct    1440
gttgaatagc tgcagacaaa cctttgatct gttttgtagg atggacagga aaagtatgtg    1500
tcaattggtc atctaccaat tatttccatt tcatggtaag gtgatgtgcc agtgcgaatt    1560
tgttaaggca ggtaatctaa ctggttggta gatttctatg tccaggagaa acatgtgtaa    1620
tacttggtgc aactggagag ctagtacatc ggaggaaatt gcttgttgac tctccaaatg    1680
tgtaccaact ttaagtaggt agcgatttac atttcattct tatttgttct attctttaga    1740
agagaagaaa ttctatgatt cggcagtaca atataacgaa agaggttgat tatgtctact    1800
tacaattatt catatgattt ttgagtattt gagacttcga tttcatcagt tcaattgatg    1860
gggttgttct ggcgcaacac aaattaagga aacgtatgtc tgattccttt ttgcttagaa    1920
ttcaattcca tgccagccta tactattctt cgaggcagtg ttacctcttg ggtaatttta    1980
agaatattat gtattggggt ttggtttcac attttgtagg atagtttcaa tctatttggc    2040
aataatgcaa aaagctatgc cagtttagtc ttgtcttgat ctgttaacag actatcttgt    2100
agtattggtt ggattaacta ggttgagttt ttggggttgg aagtaattca agaagcaagt    2160
gttgattgta actagttttc tgatttatgt ttgaaacctc aaggcaccag tatgtaattg    2220
tggaatatga attcaagctt tagcttggtt agtgagctga gttatagtct atttattcag    2280
aattgtggta cgaacctttg tattttgtaa tttatccccg agtgcagcta gtgttgttta    2340
attttgatat agttgtagct gaagttggca tactgaggtt tagcatttat agagaaggtt    2400
gttgatattg tgagaaggtt gaagtattta gtgcagatat tatttgtatt tttgatggtt    2460
tagtaactta gtggtgttgc ttatatttgg attgttaatt ggaaatgaaa cggtcgtgaa    2520
ggcaggtgta tactaggttt tgaagaattg catatttcca ggggactttg tcactaatat    2580
tctatgatgt gtaccttggt ggtatgtggt gttttacgtt gagtcgagtg taaactttgg    2640
tagccagtga tatcagagtt aatggtttcc atatttaggt ttgttactcc aagttgctat    2700
cattatagtg tataagatca tagctcggga ttatgagggc tgttttgaaa ttaggtatga    2760
ataagaggca agagactaaa gaatatggca agttgcgagg gtatcaagct ggtttagaga    2820
cggttatttt atcaggaatt taattttggg tgtggtaggt ggatgaacaa tgtggttagg    2880
gaaccgaaaa aatttgaaga ataatgaaat ttttagttgt tattagaatg gtacaagaga    2940
```

-continued

```
tataagaatt tcgagaggac ttggttcgtg ctgggattgt ttccttgatg aggatacagg    3000
tgtgactcgt atttttgtgg aggg tttggg atattaatcg aaggtcgttg catattagaa   3060
gggcggaatt ataaaaaagg ttgaaggaat gtgaaaacag agcttgtata aaaatgtatt   3120
ggagcgggaa atgcactatt gaagtgctgg gagtttt att tgggtacg              3168
```

<210> SEQ ID NO 3
<211> LENGTH: 3610
<212> TYPE: DNA
<213> ORGANISM: Candida dubliniensis

<400> SEQUENCE: 3

```
ttcatccatc atatcacaaa tcctactgct aatatcagct caatatatca aatagtcccg      60
tgggttccac ataattaagc agatagcttg ggcacttatc atcataacat gcgtatatct     120
gtatatcaag cgacaacttg gatcctgaac gacacggttt ctgcaacttt tttaaaccct    180
ttcccctctc cccaactttc aaaataacta aatacagtgc cagtaacaag ataaaactat    240
cctatatagc acatcttact taaattctct tccttctctc agaacccacc atactcacaa    300
gcttcttaaa aaactgagtc ctcctcaata gcactagaac actctaaaca tctgctcccc    360
tagattgatg ttgaactatc aatactaata ccaatacaat tcaaaccat acttccaaat     420 taacaacttt tcctctttcg tcttccatat cttacatgtc gtaattcctc tcttaccgga    480
cttatgatca acctattact aaaggaaaga cactactgta gagttcctgt caaacgctct    540
aagctcacct tcggcaataa ctacgaacca ctccagttga aaactatagc aaatcaagac    600
aggtaagtgc taaataaata caatagaaat atcaaaacct ctacattggc caatttactc    660
tcaaaagctg ccgaaccaca acacatccac aaacaaactt ttctgagtaa tcttaaacca    720
ttcctctcta gcaaccgtc tcccataaac ttcaccttaa ccataattca ttatttcatc     780
cattcgaaac acctattcca atatcggaag aggagaagtt caccgagcta ccaatttgag    840
caaatataaa ccaacttaaa gatccattgc tcctgataaa ccaaaccta tgcgctaaga    900 catttcattt tacccaaagc cattagcatc aaccaaaagc taacatatct gccaaaactt    960
gatccggtaa atcatccata tactctaagt cgaaaccaac gtttaattga acttatcttc   1020
ccaacaattt ggcgaggatg gtttaaaatt ctcaacgcaa catgcattat tcttctaatt   1080
gaaaactcat tatccaaaca ctaaataacc tcaaagaag tgataatact tatcataatg    1140
aaccctcata ccaacaacct ctaaccaaaa tcacaacaac tccacaaatc ctttatatac   1200
tttttcccca tcaaaaacaa agccaaaaat accgtgatac taaatcacat taatagaaca   1260
aaacatgcct tcattccact attttcaaac tagaagactc tcatctacaa aaattgtgct   1320
acactgagaa ctaccatttg cttgtcgcct atattatcaa ttcaagtact tccaccaaac   1380
catcatggcc acatccaccc acattggtta caaactaacc attaaaacaa actaaatcaa   1440
aacataacta ttataacaaa taatagcact actagatcgt gagtagcagc acagattatt   1500
ctacaacaag ttctcgctat gaatgtgcta atttctcagt acacctacca tcacaacata   1560
atctactcct ttaagtctaa gaacacctac tgcaagccat tacattaaac ataatttcaa   1620
gacaaaaatt gacgcagaaa ttgttgtcaa ctcttctgga aaaacaaccc ttctgaaacc   1680
aataataagc aatagtatac actacttcta caagctgttt ataatcctgg aaacagatag    1740
ttaaatagaa gcgaggcatt actgattaga tactgcctga gaagattcca aaccacccga    1800
caactactac taatttcccct acgacatgaa cacatcaaac tactcgccca ccaatgttta    1860
agtagtctaa tatataaacc ttataattgg taattctttg atgctaacca agaagcttgc    1920
```

-continued

```
aatcagaaaa ggaaggaaag aaattaatct tttcaaacta cagcagcctc gtttcgcaag    1980
ttttcaacaa aagcatagca ttactctctt taggtattga acgtttcagt gaagaatatc    2040
tatttatata cgttttggtt tgtaaagcga gttcacagca taagcctcta catactctgt    2100
atatgattat attaatgcat tattttgaag tatttaccag aagtttggct attctatatg    2160
tgtgctttag aggtagctcg tttgatttga acattgtggt tgcactgaaa accaaagttt    2220
gtgtaagttt tgtcagttaa atcttcttct taggttttct attgatatat gtagtagtaa    2280
aaattgtaaa ctgatgccat tactgattaa tcaacagtgc aattcaaatt taatagagta    2340
gtccagttta ggatatttca agttgtagct gctcagcata tggctttgtt gtcctgaatc    2400
aattcttctt ggtataggga ttagcttact gacaaagatt aatgtaggtg agaggagacg    2460
gtttgcttaa atgagatact aaaatattaa actattgatt tacacagatt attttttatag   2520 ttagtagtcc tatgcacaaa agtacttgaa ttggatgagg gaccaccgtt gaaaagcaaa    2580
ttgataatgc gaattgtagt gatttgtatt ggtcaattga tgcaccagta caatagtgaa    2640
cttggaattt atcttttaca aactattatt gtagctagtt aacaaagtaa tttaattgcg    2700
agatagtctc cgagtatttg ggtaatgtat tatttcaacc cttgactata tccaatggtc    2760
tggttatgtt acggttattg tttacggtag acgaaattaa cttgtggagc accttaagag    2820
ttgaggcttt ttttatggtt gtgaggactt agaggaatca ctagaagcga tagctttaag    2880
gcaatgatgc aatcatagaa cagtttgcta aactgtagaa ggtagctggt tgtgttcatg    2940
tggtttgtga taaaggttcc atcggttaaa acgttttttcc ttgttgttgg cattttgtgc    3000
ataattatgg aagagtaata actccacgct gttgatccca ctgtatactg aaacgtaggt    3060
tttccagagg caaatgattt gctagttttg aatgtattgt gaggttcaaa atgaaattgc    3120
tgagacgttg tatcaagctc atttcaagtt gtagtaatga attgaacatt ctacaagtat    3180
caagagacgt tggttctatt ggagatatac taatgtaata tttaggtctg tttgagcgtg    3240
attgtggtaa tgactgacta tcctcagatg gtgagagaag ttttttcactt ggttgcagtt    3300 caaataaggt tttcacactg gcagggctgg tagaaattgt taggtatgac cgaattactt    3360
ttttgaggct agtcggtggt taacggttgt gtgctttatt tgattttgac aggcttgata    3420
cgattgcttc ttatgttggc gtgagcatgt gccacggtat cagttgttca tagaggttag    3480
tagagacgat gatgcttatt aatttttaaga tacgtgagtt ttctgatgtt tgcgctgtct    3540
gttgtcggtt tatgtatgct gaatcatata ataattttaa ttggcatcgg cgatggtgtt    3600
tattccgagt                                                          3610
```

<210> SEQ ID NO 4
<211> LENGTH: 4804
<212> TYPE: DNA
<213> ORGANISM: Candida dubliniensis

<400> SEQUENCE: 4

```
cacaattccc agtaaaccat tataaaagga aaagctttca accaactccc tgcaaatgta     60
aacctaaagc acagagctct attctttaaa atccaatcct tagccacaca acatgtaagt    120
tggcttacta ggagcctaca aatcagatta tgaatgtagc aaacatactt aattatgctt    180
cagaaaagat acacccatgg acttgaaaac attatctcaa atacacctca agtcagacaa    240
tacaaaactt atagctgttg catactgcaa taggtaagaa catgaaaaca atagagttta    300
catcaatctc attttcgaat cagccaaact tcaaaaatat aaactattcc taatcaatat    360
```

```
acttcacctc attcattatt gcgcaactca cgaaaacatc taccattact actacttgga    420
acaatgaaac aattgcaaaa cgagcccttta catataaaga agaataaccc aggtgcgtac   480
attgttgaaa tgaatcgggt tcaactaaaa ttgaccacta ccgggaccaa acattaaacc    540
acgaattaaa gcatgcactg aatgcaaaca ccattaaaaa tgtctactgt taagtgatta    600
cattttcgtg tgttttctac agacgaacgc aattctacaa tgctaatcaa agctgtagtt    660
agactagtta agtcctctat atgatttaaa gacactgcgc tttctttata gcctattaat    720
tgctaaacga cccctcaaa atgctttcta agaagatgct ttggctattc gattttacta     780
aactacgtat cctgttcctg cagtctaaca gggcattgtg aatttgcaac aaagttttca    840
attcgttttc ctgatgccaa tcatcactta aattaggtt tcacgtgcta cagttatgct     900
tctttcagat gttggtacag cctcaggtca atcggttttg gtttggttgc tgatgatcgt    960
cgtacgtagt atcgagataa tcctaagtaa catcaaaaaa tacattgccg tatggtagca   1020
atgtagctgt tccagacacc tagtaaatga ttaaagcttg cgtttcttaa caaagaaaac   1080
tgagtttgtc gtcgtcgaat gcaggcaagt atggggatta gtgctttaga gctaaggagt   1140
tgaacgtgtc tttccaactt gtccaacaac gtattcagtc agcttaagct ttttgttcat   1200
gcattagagt tttgattatt ctggtatttc ttactagggt ccaccttcgt aaagtgatac   1260
ttgcttgaaa gtttctacat aaatattaat tgcaagtatt agtttgaaat tgagcaaccg   1320
gtggttcgag gagattgtcg gttgaaatgg gaaattagta tatttgagta agtttgctag   1380
ctggattact gtttccaaca actagtaggg ttcatttgaa cttatactat agaagtgttt   1440
ttgcgaataa gttcttgatt gggacagatt aaaatatttg tgcataatta aaagagtttt   1500
aataagttac ttaataaagc tatactcgta ctagagacat tcctttagtc acgcctcaga   1560
gctagaaaat ttaagctgcg ttggctttgc ttctgataag caacgtttag tcaattcatt   1620
ggaagatgta gtagggtgta tcaaatattg agaaattttg gattgtcttt tacggaagaa   1680
aaggttcttt aaactttgat tgggggagca ttagaatttg agcatttata gttgaagctt   1740
tcttttccaa gtgtatacta cattttcttc tttaattgga ttatcttaga taaaggaaat   1800
tacgtaagat gtaaagttta taggaattaa agtgacattt gcatggtatg aatatgatta   1860
atgacaaatt gtattatgga ggtggtggag taatgggtgt acggtattat cgtttatttg   1920
aaaatgactt ggtcgcctgg ttttcgacga agactggaag atacggagaa ttggttaata   1980
gtgttgacca ttggtgatgc agcaatagag ttccaagtga gttattgatt aatcgatgct   2040
atctattttg gcggtgaatt gacaggaatt tctttttttt ttaattacta catgcatatt   2100
tctcgtgtga ttttcagatt ctcagttact agtttaggaa gaaaattcaa taaagagtca   2160
tcttttctac tgcaaaatat gtatggagcc ggttcgaaat tagtatttct attactataa   2220
atagaaaaaa tatgcaatta tcctcccta aatttccttt tttggattct ttatcccttg     2280
aaacctttgc ctaggtcgac aactctaggt cgaagtggta ctacttcctc gcactagaga   2340
attgaactcg gccccatctc ttcggcttct catttcaagt cttaataatt tatactcaat   2400
aaaacaaaca actacatata aaatcaaact ttatataaaa taataagaac aattcattca   2460
tttaatctcc ttcgtttttc tgacttgtta gtatatgata agtttctctt gccagaagat   2520
aaatgtttca atctttctt aagtacaagg tacgttatat aaatatcatt gaactggctt    2580
ttttcgtata gctttcgtct tttaatatca gcaattaatt cggatagttg ggggagaccg   2640
ttctccatat catcgagttt ctcaaagtta tctgcactta ttcttgatat attcagcgta   2700
ttctgacttg ttgaagctgt tgtattatga cttgttgagg ctgttgtatt gtcaattgct   2760
```

```
aaagctgttg tattgtgatg tggaggtggc agtgaagtga gcagctcaat taaaataggt   2820
tataaatctt tcaaaagatg catatttgtt aagaaaactt tggatatcat tttcagtatt   2880
tctggattga ataaaatatg ctgcaagtct tttattatca ggtcatgaat agccttttgt   2940
cgctgcttgt cttcaaaaac tacaatttgt tttaatttca gagccacatt ttggcaactt   3000
ctgtaaattg gatccaacat tgaattgatt atttcaacta ttggagtttg ttgttgtatt   3060
gaagtcctca attcttcaac caattttttg cttagccgac tattatggta gtagctattt   3120
gaaaaatcat ggttatggtg ataaatccaa tcagcaaacc actgttcccc tttatgtttc   3180
tgctgaacta tgattttgc tggacagttt attttttatg gattcttttc tgtttctttt   3240
ttttcacagc aaatacattg ttgatattgt tttcattcgc ggcttcactt tgattttgtt   3300
gatggtttaa acttgtttga gtataggaat caccacggtt gcagtggtat tcctcgtatt   3360
ccacagcagc gttcttgtga ccgtgagaaa ccttaggcta ctttatgtga tatgacacat   3420
taattatgat caaatcatta acttaaactc atctcattga atacaaaacc tctataaaca   3480
agtatatact ttgtaaaaac tcgtttgtgc ccttgatatt gaatcataaa tccaagttgg   3540
ctggaaaatg tacatctcac taacaattta tctatctgta attgttgaag tggaaaacta   3600
gtttagatca taccataact tcaagtaaat gcaaattaat agccctaagc ccctgtccaa   3660
ttcaagttaa atgatccact caacagccct aataataaga tttcatggat aatgaacatg   3720
ccactcgcta ttcaatcctc aaaataaaaa cccactttag catcaagcaa tttgagcaat   3780
aacatccgac agaaattgtc aaatagaagt acaccatttt tgaattatta taactcacca   3840
aattgcaatt ccaaaagttt gacacctact ggtcaaacaa aaatcaataa ctcatctata   3900
ttagttagtt agtaagcaca gttttttaaa aacaagggta ttaatcatac atatcatgac   3960
ttaaagtatc tgtaatccca gtagcagtaa ctatttgatt gatttatgat ggaaactgat   4020
ggattgatga acgaatggtg aaagaagaag gagaaagaag tggtggtgag aggaaaataa   4080
ttgaggtcac gccagcctgg catttatcat tatgaagaag aaaaaggaca gagcaaggga   4140
tgaaagatat tttggaggta agcaaaatgt aaacaaaaaa atgtaaacaa aaggagtaca   4200
acatgcagaa ttcttatgct caaatatgca tgttatcgcc attggcaatt ttctgtcaat   4260
tcaccgccaa aatagatagc atctgattaa tcaagaggaa cgattttgtt tatgtttgat   4320
ttttactttg atgagaggtc aggcagttat ttgatgccat gtatacttgg caacttcttg   4380
caggttatca ttttatggat attaatggtt tatatgtaat tcattttcac gtcgtttaaa   4440
agtagagctt ttagagggtt ttctactgtg ttgtattttg tgagaattgt atactcaaag   4500
aatccacaat tccatgactt gttggataat ttgtaaaaat atataaatgt atgtattgag   4560
acattgttac tatgtggtgg agggtcatcc atttgttggt tggaaaactg tttttcagtt   4620
aggtctttct ttggttttgt ttgtcggtag tccgtcattc ttgggttaat gatgacaaga   4680
cttttcccta gatgttcttc tctgagagtt tgaaatgggt ggattcggtt gggctggcta   4740
agtttggagt ggattattta gaaacgagag ttttgtttat ttggtagggt gcatgagggt   4800
cgcc                                                               4804
```

<210> SEQ ID NO 5
<211> LENGTH: 3833
<212> TYPE: DNA
<213> ORGANISM: Candida dubliniensis

<400> SEQUENCE: 5

```
atggcctctc ccttacaaaa tttgccccag ctgatactat tgagtcacac atcacactcg      60
tttgctaaac cgaccatttg aatcctagct tctcgtgtac aagtattcat caaacatatc     120
tttgcttctt ttcacttcgt ctcaaaaaag atacaccttt gaaacactcc cgaagcttca     180
gctattacct caatcacccc tcatctccct acctctttat tcgcataata tctgttttat     240
tacctctcta tcccagcaat accatagtat ttcttgcacc ctattttaac tactcgcaga     300
caaccgagtt tacatcaata tgctaaacat tcctctgcca cacctcacac cacaaacttc     360
atgtcttcca tagtcatgcc tctaaactat cccagcgatg acaacaacat cttgccatca     420
acaattgctc caaagaaaaa cgatactatg tagtatcgcg aaaacaaaaa acacgatgaa     480
gcactcttgt agaatcagcc gtcactacgt taccacgcta acccattcca atcaagtgaa     540
cattaaacta actatactgt ggatgaaata atgtatttg caccaccatt tcccattcct      600
cacacataca aactgatttg cactaagtga atattgcaac cttccaaaaa tttgttactt     660
acaatcttct gatttctccc tgaagtcctc ctcaagctga ctcaactctg tttaggtact     720
tcgaacctat acaatatgta aataacagta cagagaaacg tgtctatcta aaagttcttg     780
cgtaaattaa aacaaattca ttttgactat tgtcagtgcc agcaacaaca tattgtaaaa     840
atcataagtt aatcacgagt taccatacta tttagttgac aagttccttt attccgagaa     900
cattgctgac ataaagaaat gcctatagca tccgttttca taccgcaacg acacctcgaa     960
ttttactcat ttgttatagc atattctctt ttgcactatc aatcaattt caaccgatac     1020 ctcaaaatac tgctaataac agattgaaga caatttgatc acaccatcat tttgtcccga    1080
gaatttgaaa agaatataa ttatcaactt accaattcta gtcctgtcat ttcaaagtac     1140
caaacaaaga atagcagcac aaagaataag cataaatttg acattgtctc acaaggcaat    1200
tgcaccaaaa atcaaataac gaactgcaag agtactccca tatcaaatct gtaaccgaat    1260
catcaggatt tattagaact acccgatgca attacactaa caaatagaat tctttcctga    1320
ctcaaaactt atacactacg aagctgtgag acttctcaca gaatctcaaa ttttagtact    1380
tttctccaaa agtttttaca caatagaaac aaaatatact caatttatca aaaaatagct    1440
tatataaact tttttctaat tcaattttt ccatttacca tgacacaatc tatattgtct     1500
ctattcaaga aaccacactt aaatacaaac atcatcatgt atcttctgcg tagaatagac    1560
gcattcatgt tgaacataac atgagctcca gtaccaacga aaacgacttc ctcattatct    1620
taacaacatt ttaccttaac agttaaaaac ttaaacaaaa taaatatcaa actaatgcat    1680
ggtacaaact cctgtattaa acatggtttc tcgactacat tggcagtttt caaatgcaga    1740
agtgtaaagg gagtcgtaag cttcttgagt aatcatttgg acaaacaaag ccaccgctaa    1800
tatcacgtct acacatatga cagggagctt ctaacaagca cactctcccg agccatacta    1860
ggggccatta gataaacgta tacacacagt gcatttactt aagcaacggt taaatctcat    1920
ttcaagaaga tatgcttggg taggtcagat acattttctg acagagtaga tttcaattct    1980
tcccaggatc cgatcgacat aaattcgatt tctcagtgtt tgattgcaat ccattatcca    2040
agaacttatt ttattgacta acccttttct ctcaggaata tgtgcgttaa catatataga    2100
ttgccctgat tattgacttt aataacttga acaagaatgc cttacttatc atttgatgat    2160
attatactgc aatcattagt cctaaaccca tgaaagtttt attgaaaata gagcttgtcc    2220
ctgcaatctg gttaagtctt ctatttatag agtcgtgata actctgaggc tattataatg    2280
tgttacataa ttttgatcca atttaatgat tctacttggg actaattgga ataaagattg    2340
tttggtgaat ctggaatagc atttcacttc aagtaaatta gagaatattt ggaatagttc    2400
```

```
tctggtagtc ttaataattg tagacaagca atctgagaac attaaatggt agtagcagaa    2460
ctaactaact tttgaagaaa atcacgttcc cgagctgctc tttggatgta aggcgaaagc    2520
caggttacgt acatggtatc cacattctaa atggaaaatg agtgactaca aggaaattca    2580
attcataaga tcattcgcag atactattac gatattggtt tctgtattga cgagctgaca    2640
acgcgtggaa agttttcat catgctggct tgtaggtgtc gttgaatctg caaatctaaa     2700
cgtgtggaac agcaggaaat acaaaattgg ttttagttgc attgtatatt ttaatatgaa    2760
ttgtatggtg atcccgttta gagtagtacg aaagttttg aagacctgtt atgtgttcat     2820
ccagttgtct ataggctcac ttttgttctc atgttggatg gtggtctctc aagtcgctca    2880
ttaaaggcat atatgtatga taattggttc cacaaggcag ctgaaacact taacaaaaca    2940
ccttctttac acaagtgagt tacttacgta aggtaggagt ttgtagtaat ctagtttgta    3000
tagcttttgg tgtatttgca tagatctcga ggagaggctt ctcactagaa catgttgtca    3060
gtggagcaat ctgttaggtg tttaaatttt ttgcagtgga gtaagttctt attactatct    3120
ttacggtgag gttgtataaa tcacctttcg gcttagcaga acctaatcgc catgcttgtc    3180
cttaatatat gtgttgatgt ggtattacgt gtgcatatca gtgtaaggat agatatttgc    3240
gtgtagttta aaggtgtaa gaggtcacat tttgcataat atcaagttgt gtttagtgtt     3300
tgggatgatt ttgttggagg tagaagcata tttgaagagt gcagtattaa gcttagattt    3360
aaaatttgtg tttatgaggc ggatttgagt ttcatagatt ccaagggccc gttggattgt    3420
tgtaataatt ggttgtgggt tttatttgta tctcgttaat tgggcgtgaa gaatatggtt    3480
ttgagctgct ctatggatga atcagtagga ggtgtttggg cgataactga tttatttggt    3540
tgtagatgga aaaggcaatt ataattatcg gtatgtcgtt ttctttggag caattgttga    3600
tggtaagatg ttgttgtcat cgctgggata gtttagaggc atgactgtgg aagacatgaa    3660
gattgtggtg tgaggtgtgg cagaggaatg tttagcatat tgatgtaaac tcgtttgtca    3720
gcgagtagtt aaaatagggt gcaagaaata ctatggtatt gctgggatag agaggtaata    3780
aaacagatat tatgcaaata aaagaggta gggagatgag gggtgattga ggt            3833
```

<210> SEQ ID NO 6
<211> LENGTH: 3649
<212> TYPE: DNA
<213> ORGANISM: Candida dubliniensis

<400> SEQUENCE: 6

```
agaagcagcg acccaacaga taataatgta agtaatcctt ttcaatcaaa tacaaataac     60
caccgaaaca attgtcagca aatagaattt taaaaaatg aatctcaaat actgacaata    120
acctctccct ctcaaatact accaactccg tactcttcaa ttgcactgta actattacat    180
caaaacaacc aaatcacagc atcaaactct tgatatattg actctaccca atttcgctca    240
aatgacagac caagctatat tgttgcagcc attcatatca acattatttt taaccagctg    300
tgtctctcac ctctctaatc tcattccact aaaccgacta gctgcaaaac tcacctcgtc    360
cacaaaaaac ccatatcttc cctaccttag caaatcatcc cagaagtgat cacctctttc    420
tccagaaata gactggttga caatacgaca taaagtcaaa aaactgaaca atcatcata    480 cttgtttata atatcaacta cgttccctaa caaattactt ttaaaacatc cattcaatgc    540
gaaggcaaag ttagtattgt cagtaataat tattccacaa gtacagcgct aagctgagcc    600
atgtgttagc ttcgaaattg atacaaaatt tactaaaact acaaaagcca acaaccgtaa    660
```

```
caaaatcagc taagttatgt ctaaaattac cgtgatatgt tcctcttttta aaaatatcgg    720 aatattacat ttctgaaaag tttaaaaatt caaaagaag gcttcacct aatactttca       780 agtacatgtg atagatctca ttacaaaata aaagactcat tcctttcaat caagccaatg     840
accatcttat acttcaacaa accactctac gctctattct aaaaatatgt cttgcaagta     900
ccccgagtac tctaaaccag tagaaacgtt ttttgaagtt acactgtaac cacttcgaca     960
cctcgatcca ctagaaattt aatttccaag ttagagtgtc cattccccaa acttcatacg    1020
gaccacgtag atcctagaca ttagtttaca aaaattgctg gcagatatca tctcaaacca   1080
tataaaccta cccgtttact atagacacta taacattctc tctatatctg tgcatttctc   1140
aagtccttcc agcattccca gaacctcata tatcaaaaat atacaacaca tcgttggcaa   1200
aagtaccaac tacctattca attagctcag tctttcttaa ctacgacact agatggcact   1260
agtcaaacac atgcttcaaa ttcaaataac tgcaatatct acaattcttc taaaaatgaa   1320
cgagcatgtt accattgatg gtcactttaa agtgcttttc attacaatac acaactttca   1380
agacaggcat aaaatacggg ggtccttttt gcaaatgcct gaacatatat ctatcctcct   1440
acaccacctt ctaacccct tgtacaaaca ttacttaatt tagaacacca tcatgccagc    1500
aaccattcac caattcgccc tagatacgct tgtttcaaaa gctgcccttc cgatcattta   1560
ctacattcaa caaccccaca agggacaaat aacagcaact gaatttttt gctgcagttc    1620 atagtaaccc cggttaattg atcttgtagc aaaactacac aatgattctt tccaaatcgg   1680
gctcataaca agctcttcac tatcagtcag ttctttaaaa gtaagtattc gcaggcataa   1740
tactagctct catcattaat tctgaagcca tagcattagt tcttttcaac accgcgttat   1800
gaaatgctcc aatctttaaa tccttttttac caactgtcca cctactccaa ccactagcac   1860
taactgcaat cttcggatgt gttggatttt taaatactat agaaacaaat tttagagagt   1920
aaggtcaagt cacagattgg aataacatca attctccaaa atttttttaag atacaatgac   1980 aaacagaacg taaaactagc attgaaacca ataacaagga aagagtatat aaaacatgtt   2040
tagcgatgca tactagagat aatatataga cttgttgatt tcataagtca ctgaatctat   2100 cttttcattat tatttttcta gtgtaaatag tttctttact attgaggata gtcaaatgat   2160
aaatgctttg catgagagat tggatttgaa catatattac aaaagatgtt cctcttctgt   2220 taccttttttg acagatattt aaagcctttc gatgatagtt aaataaaaga ctactgattt   2280 cttttttccca ttgcttaatt tatatcaatt tttcgaagtt gattatcgca accaggatcc   2340
tgtgatgtct tgagacttct actacatgta tttatgattg ttgattttaa agtagtgaag   2400
gcatatgctg tttgtgtgtc ggagtgctca gtgaattaag tttctttagg ttattggtca   2460
ttccaaaaga ttgactagtt tgtgtacttg atggtgtttc tcattgtaat tgaattcctg   2520 cattttttcta ttttatggag atattatgtt tgggatttag aatacgcatg gtaacactag   2580
agtgtgacat ttgaaagagc acaggtgatt attgagattt caagggtgt cgagcatgat    2640 gtaacaggaa tcagattatg actgtattat tatttagtaa tggtcgtttt gaagggtgtg   2700
gttgattggg gagacacttt tggtgactat gaaagcacaa tagttgttgc gagttgtctt   2760
taggtgtaca ttactcggct ttggattatt ggagatatag gtaatctttt taattgaagg   2820
tgctagaagt ctgaatgttt cattatgctt tgagaagtga tcatcatttg attcgcttta   2880
gtctgacttc tggtgtatgc tgaacttgca ttgatttgaa tttgttactc tgtagtttat   2940
gggcaaaatg ttagtttgag aggcaggtca gaaactggat tgagcaagga ggatttaagg   3000
acaaagttga taaaattaga ataggcataa ccgtaaaatg aaggttatat aaacatacat   3060
```

```
tgtttatgtg gttggtgaga gtgtcttgat tagtttagtc gactcggtcc tgattcgagc    3120
aggaatgaga tctataatgc taagctggct ttagcggttc ccttgctttg aaggcagaaa    3180
atgagccaag tttggttaga tgaatgtagg cacactttca agtatttgca tttttgaagt    3240
ttatgtgagc acggtgtttt caaaagtggc atgatttgtt ggcttatcca acgaagatga    3300
gatatcaaag gaacataatt gtatatcatt cagaagataa agaaataag tgacgtttaa     3360 atgatttaaa taaattggag aggaagaatt tgatattcac taaggtaagc gagatagaat    3420
tggaaagatg acgagagcat gtactcaact acgtgtcgta cgactctagc taatcatgat    3480
aaggaagtat taaaaagcta tgatcatgtc aagattgcaa atctaagcaa agtagcataa    3540
agccagtctg tctcatctgt gattttaagg gtaaatttca ttggcagtaa tgatctgcca    3600
tacctaatga atttgtcatc atttggttcc tcgcatttca atcaagatt              3649

<210> SEQ ID NO 7
<211> LENGTH: 2992
<212> TYPE: DNA
<213> ORGANISM: Candida dubliniensis

<400> SEQUENCE: 7
cccagaagta tccactaggg aacttgcatc ataaccccat tccccagcct cccaacaaag      60
aatatcacca tcattaaatt caatagtaga agcagtcaac agctaatttg attccgaaaa     120
actcaggttg ctgtaccatt gaccagaaca attgcgaact gtcttgcaac ctctcaagca     180
atcaaaactg acacaactga agcacaata agcattttc agtcctaaca caacatcctt      240
acagaacgaa ttgattgtaa gtctggtaac acttttaata atatctagac aacaacaaat    300
ctagttttac taaccttggc tacaactcta tgcataacac actcctcagt aataaaaatt    360
actctatatc atctgtacat gtgagcctac atcaaatcga atattggatg ataaaaacac    420
aaaccttctt ttcagaaaaa cagccaccac caaactcttt gaaagcagat aaaaacgaaa    480
taaacaaaaa atcaagctgc tatacaagta aggcgtagac ggcattactt tcatgatccc    540
taacaagctc catcctaaag ctatgatgtg tcaagatctc caaatgtaag caaatcactc    600
ttagcgtgca tttaacaaag ccattcacaa tccaacttcc tctctagtct atatacaccc    660
aattgtacaa caagttgtag tcacaagcct aagctatatt aactcattca tgatattatt    720
cctgccaaga gtggactcca ctattaacgt atagggtgac cccattcaac agcttctagc    780
aaaactatgc acttcagtct ttacttaatt ggacttccat cttgatacat tgcttctctc    840
ttgcctctgc gaaacacatg tttatcaaaa ttggaacttg gctaaaccaa cctcatcata    900
tattaataac ctcaaacaat gaaactgatt ccacccgaaa tattacatac tgcacaacag    960
caaccaaatt atcatgcacc actatctaca aaaacatttg ttcacctcaa taaacccatt   1020
gattctgaat gactaatcat tgcgtattaa taacaacacc ttgaatatat tagcgtccta   1080
tgatttaagt aggcgctaca tatgaacttc gtgccaggcc tattctaatg ctattacctg   1140
tatatatttc catactgcaa atactgactt ggagtatacc tttcatcatg tacagtgaac   1200
tctctcaaac atccgtatat gatttaatta atccaagaac cccgaatgac attcagacat   1260
tatctccaac taaatatac cgggattcct aaagaatttt ttcctgaaa tacactagaa      1320 ttccccgtta gctagtacaa ttcttcaaaa aaaaattcta ttccacatga actttgccag   1380
ataccatcta actcttaaac attcctcccc atctcatatg catgaccacc aaccagttcc   1440
actgcttcca atagcgaggg cggggagagg gcaaagccca agattacatt agattttta   1500
```

| | |
|---|---|
| tgtagatctt aatattctag catgtctcag cattacaaat tcattggaac tgcaaatcac | 1560 |
| ctgttcacaa accgatacgt taaagtaatc gataatatat ccttatacta cttttttttc | 1620 |
| cagtctattt caaagcacag taggcatcca agtgctatat cacaacctct gcttaataga | 1680 |
| ctgtgcacga tatattgtgg agctagctgg agaggtgagg ctagcagtat gtgactttgt | 1740 |
| ttctatttta ctttcatagg gaaatcaata cgtactaaaa tttacctttg ctaccatgtc | 1800 |
| taatatctgg tgagcaggaa gtaatcggct tcatatatta aattgtaaga cgattatgca | 1860 |
| tacgatgctc ccatagtttt ttattgcatt gatattcctt gtaaataatg gtgtcacaat | 1920 |
| tgtccaaata aataaaaaga gaacaatagt ttcagtacat ttgctgtctc ttcaaaacaa | 1980 |
| tgtataatgt ctctgctttg ctaaattgaa aaactggtaa tggaccaaca gttatgagct | 2040 |
| gctatttaaa attgcaaata ttcaatcaaa atgcttgcgg aatagaacgg tgactctgaa | 2100 |
| attttttgtta ttggtttcaa ctatctctta gctaatatca ggagaagttg agttaattct | 2160 |
| ttagaatagc attgatgagg tggcatccaa gcgataggtt attctaggtt ctattaagat | 2220 |
| tggttagttt tgaagtatat gatgtcactg tctttaatct acagttcttc cagtttgtgc | 2280 |
| cttatgttca cgaaaaggaa gagattctta ggtagagtga taaataattg gtactataga | 2340 |
| atataaacac tactttagga gattgagatt tcttattgta tgtgagaaac tttcttagca | 2400 |
| gaatcaaagt atggttgtat acgtaatatg atttcaaatt cagagaaaat aatgtgggta | 2460 |
| tgctcgtgaa catttataat tgtaggcttg cacaggaatc ataggaattg tggttgtatt | 2520 |
| gatttagaac agttatgatt acttttatga tagctggtgg ttttaggaga taaaatacgt | 2580 |
| agggtatttt ttggtcttgt gtggtgtcga aggtattgaa aacttgtatg gtaggaattt | 2640 |
| atatatgagg tgttgcaatt ggtggatgtt gtgtgtgagg cgtaaaatta aagataaaca | 2700 |
| gtagtatgag atattgcaag attggtgctc gattgtcagg gttgatgtga tggcactgat | 2760 |
| tacaattatt tgatagccta atttcacctg atggtactac agatcgatat aagttttggt | 2820 |
| taattttatg ttgttttttgt atgaaacgtt tagcaaatgg ccctttaaat ggtagagcat | 2880 |
| gggctaagtt cttttgtggt aaaatgtgtt tttgaaattg gatgtacatt atttgttaga | 2940 |
| catgatcata cagaatcatt tacaagcatt gctggttcaa agtcagttaa ta | 2992 |

<210> SEQ ID NO 8
<211> LENGTH: 4816
<212> TYPE: DNA
<213> ORGANISM: Candida dubliniensis

<400> SEQUENCE: 8

| | |
|---|---|
| atgctaccaa acatgagaa ccacagcagg tctggtgttt attccacagt gacttgggtg | 60 |
| tccacagtat gtcttccgca acaacagaat ctttttcgctg ccacagacgg aggcaccatc | 120 |
| accacaagcg ttatgccaga gcagcacaag gagtcattgc cacgcattga ccagcaacaa | 180 |
| gtaagcgtcg ggaacaacct ccaaaccaac ccgcaacttc aacaaaagtg aaactaagct | 240 |
| tgctgtatct cttctaaccg agtcagtcaa ccaacgaaat tgaacctatc aaagcacttg | 300 |
| cagcacacat tataaactgc aggattcttg gtcatatgtc ttgggatctc tagagatctg | 360 |
| gtttgcaaac gtaactaact tcaaaatgat ctaatcaaat cgctgacatc ctgaatgtca | 420 |
| aagcacaaaa acaacactat tttaattcaa atagtttgca actacttcta atgttgcata | 480 |
| cacaaacaac accgaaaaga cccatccgct cctgacaaat cttcaaattg acctaccaat | 540 |
| tcttcgctcg aacaaaagat tgggaaatgc atcaatcctt gaatcaaacc agagagtgag | 600 |
| atcctgtatt tctatttaca tttccatcta ttctcaaaac acgaaagcgt tatctgcgta | 660 |

```
attgcaatca ttctaattag gttatggaat atagaaaatc catttccaaa aagatagtct    720
tttataaaca agaaactcct gaatattcaa ctataactca ataccaccga tagcatataa    780
atctgacaat acagcatagc aatgaatctc tacaacacta atgtacgact atttcccaca    840
ttctattctg catagtccat gactgaaaca taacaagccc accatcaatt gggacgacca    900
ccaattccat ttcaatacac acaaaccgtg tttctaacca gatatctcgt ctcctataaa    960
catggacttc tcttcaccct taaccaaaca aagcgaagaa agtacattaa cacttgtact   1020
gctaagttca agcatagcct ctgctcttac caatacaagt tctaccaact tagattaata   1080
ccagaagcgt atctgtaacc tcatttagaa taatatttcc ttatactcat tcttaacttt   1140
tccaaacttt cacaaaccaa gtctaaacaa tcaatctgac caccactacc aacagtttcc   1200
acacaactca gcaagacacg tattgtcaat atcatactta tcctctgt tacttcacaa     1260 tcatccaaaa agctctatca aacaatagcc acctcccta taattacaac tcaaggtcat    1320
acacctttag aaacctaatt caaatagcta ttggtatcaa cagaccgaat gcaacactta   1380
gtctccaatt tcactacgga ttctcagaat ccatgcctaa tcgaatatct attctgggtg   1440 caccaaaacac cctttgtcta ctaacagaac ttgttttagt ctctgaatag ggagttacag   1500
ttctaaatca caactaaca cttgctgtat actcgatcta catgaagata ctcttgtgcc    1560
aattctgctt aataacactc tctaaaagac gaaccttagg aaaattccca agtagacata   1620
acacagttac agaactaact caacgaaact ctatacatca cagccagtaa tgtgactcag   1680
tgatcaataa aattcactta cttgcaaaca aaccaatggc ttcctgagtc aaatcaccat   1740
ctgagatgca aagcgtaatt ttggaaatag ctctcttttg cccatgtggc aataaatatt   1800
acgctacggc tgcaatccat cgtccctaca gtacacaccc aaagtaaagc cattgcacta   1860
cacaattcta gatgatatgc aaaacggatc caaataatat aaattctaca ctattctaat   1920
aaacataatc caaagagtt ctcgttaaaa tgcatttagc ggtagtacaa gatgcagtaa    1980
ctacaataaa tttgtcattg gttctctcaa cgatcgctat tctaatgaga atatgattca   2040
tagccagaaa gggtttgcag agacaacttt tcctaccact caatcccaat ttctctctag   2100
aagctactct ttgattttg ggtcaatcac agtacttaca ttcacaaagg caatggaaca    2160 tgttcctta gatcggtccg cattcaacca attggagctt tgactgatta cagaaccggt    2220
cgattgtggt ggatatttgg gttgcaatgt gctctttcta agaatcatcc taattgctct   2280
atcctcgtag tatactcgga tggttcaatg tacaatgaaa gcacgtcgga ttttgacaac   2340
tttaggatca accagtagaa tgtaagttca atgttgcacg aatgaacggt ttgctgtttt   2400
agatagacct gttagggtac tgtacattta cattgtaaaa gacaatcaaa aggctacgat   2460
gacaagatcg tgtaggcaac ctgctctttt gaaatgcgtt ttgtaataac tactactagc   2520
ttatactgtt gatacaactg tttagcatac actagtaatt gaagttttcg gacacctata   2580
taattatata tttgatgatc tgcatccacg atttgtttgc actatacaat tggtgctatt   2640
ttgtatcaat tcaaccacta attgtaaga tataacaaac gaattggctg ccaaatttac    2700
aaatctctga ttttttggtt tcccgtacct gcagctatag ctattgaagc ttcagttttc   2760
atcttcttaa gagctggttc tacataaatt agcttaaagg ttgacaaaaa tagattatgg   2820
ttatatggtt aaaggttgac aaaaatagat tatggttata tggttaccaa ctatgacgtt   2880
taggcgttat tctttctggt ggtttataat agaaggtaag tcgattatga gcgaaattaa   2940
tatgtgtaga gtatctgcca gttttatact taacagttag tggcttatgt tgatgctagt   3000
```

```
caactaatgc ctactttgta taccttcatc aatatataga tgtttagatt aatcaatttt    3060
gtttgacatt gtggaaagtt aatcgcgggt ataagaat ttgatagtgt gatgttttg       3120 acaggcttat caaatgagag cgagttttgt attttattaa atcgccaggt ttttagcaat    3180
gtttctgtaa aacgactttt cttattggca aggcgtgtgg taggctatta tatgttatct    3240
gaacatagca tagctaaagt ggttgttgcc atacatgaaa taaggttatt tgcaataagc    3300
tggaattttt gttcgaatta gaactggtac tggtataatg agatgacaat agtcatggaa    3360
aaatcagatt gctggtttgg ttggtagatt tgtttagtta tacggttact gaagttgtaa    3420
gaattagtag tttctaaaag gcaagagtat cggtagaaaa ttatggtgat agtactatag    3480
tcttatatta ggctttaatt ttcagatata tgagaaagat gtttggtctg ataattccta    3540
tgtacattta ttaatctatt ctacaggaag gggtcaattt ttctctttgg gttgagattc    3600
ttattctaaa ggcgcaaaat tttagaaggg ttatcacttt gcattttggc tgggactcca    3660
ggaatgcatt ggaacaatct gagtaagctg ccttttgtat gtggaaatga attgcgttgg    3720
gtaaagataa ttttaatgca gttttttcttg aataacggta cagagtgttt gaataaattt    3780
ttagtagttt gcagattcac gtagtgtgct tgccccacag cggcctcgtt tagttgctgt    3840
ttggcttggg ttgttgtttt ctgctttaaa ttatgtaatg taattggtat gggactggtg    3900
gtgagacccc aaaatgaaag tgattaatag actatgctag ttcgtattcc caaaatatat    3960
gcatgaagag ttccagtttt ggacattttg caatgggtga atttatatag cagtcttaac    4020
agacctccaa tgaatattgg gttaagatat tagttgtatt agtaaatctt gtgaggaaat    4080
agtgattaag ttttagtatt tggcagttat tctatttgcg agtgctacgt agctcattct    4140
ttgatttgtt ggtgggtatt gatctggatg ttgtgggtgg ctggtggtgc ttcaatgcga    4200
ggaatggtaa ggctttgtta attttgaaga ttgagttatt taatgtgctt gcacgtcttt    4260
taaattaatt ggattagatt gggaaagaag ttctttgtta atagtccttg atattttagt    4320
tgtaatggta tattgattaa cttccttaac ttttggaatt gtgaagaagt taaagcgttt    4380
ttctcgttgg taaatgagtc attgttggat tgatatggtc caggttttta aggtgcgtaa    4440
gttatcggga tttcctcagt caaaatatgc ttgtgttttt atatccggat tctgagacat    4500
gcttcagtgt atagatgtac aacgtaaaag tgggagttca ctgagcatga catgttgcag    4560
gaatggtaaa cccttgttaa ttaaccgttg gtgttgaagt tgccggttgg tttgagggtt    4620
gttcccgacg cttacttgtt gatggtcaat gcgtggcaat gactccttgt gctgctctgg    4680
cataacgctt gtggtgatgg tgccaacgtc tgtggcagcg aaaagattct gttgttgcgg    4740
aagacatact gtggacaccc aagtcactgt ggaataaaca ccagacctgc tgtggttctc    4800
atgttttggt agcagg                                                     4816
```

<210> SEQ ID NO 9
<211> LENGTH: 24
<212> TYPE: DNA
<213> ORGANISM: Candida dubliniensis

<400> SEQUENCE: 9

```
aagccctttg gatgttgact acgc                                              24
```

<210> SEQ ID NO 10
<211> LENGTH: 20
<212> TYPE: DNA
<213> ORGANISM: Candida dubliniensis

<400> SEQUENCE: 10

```
ccatcgacag ggcccatgtg                                              20

<210> SEQ ID NO 11
<211> LENGTH: 20
<212> TYPE: DNA
<213> ORGANISM: Candida dubliniensis

<400> SEQUENCE: 11
tatgattata ccccaatcca                                              20

<210> SEQ ID NO 12
<211> LENGTH: 20
<212> TYPE: DNA
<213> ORGANISM: Candida dubliniensis

<400> SEQUENCE: 12
aggatcagtt accaatgttg                                              20

<210> SEQ ID NO 13
<211> LENGTH: 28
<212> TYPE: DNA
<213> ORGANISM: Candida dubliniensis

<400> SEQUENCE: 13
caacaatcaa caatttctgc tcctcatg                                     28

<210> SEQ ID NO 14
<211> LENGTH: 28
<212> TYPE: DNA
<213> ORGANISM: Candida dubliniensis

<400> SEQUENCE: 14
aagtgggtat caccttattc gcaaatga                                     28

<210> SEQ ID NO 15
<211> LENGTH: 25
<212> TYPE: DNA
<213> ORGANISM: Candida dubliniensis

<400> SEQUENCE: 15 ccttttttaaa cgtgacacgc tcaaa                                       25

<210> SEQ ID NO 16
<211> LENGTH: 24
<212> TYPE: DNA
<213> ORGANISM: Candida dubliniensis

<400> SEQUENCE: 16
ggaaaagttg cgtgaggaaa tgga                                         24

<210> SEQ ID NO 17
<211> LENGTH: 24
<212> TYPE: DNA
<213> ORGANISM: Candida dubliniensis

<400> SEQUENCE: 17
cgggtgcatc taagaagggt ttta                                         24

<210> SEQ ID NO 18
<211> LENGTH: 28
<212> TYPE: DNA
<213> ORGANISM: Candida dubliniensis
```

```
<400> SEQUENCE: 18
caatataacc ttgcacccgt caaatacg                                        28

<210> SEQ ID NO 19
<211> LENGTH: 28
<212> TYPE: DNA
<213> ORGANISM: Candida dubliniensis

<400> SEQUENCE: 19
gttgcagtgc attgtacgag gtaagctc                                        28

<210> SEQ ID NO 20
<211> LENGTH: 27
<212> TYPE: DNA
<213> ORGANISM: Candida dubliniensis

<400> SEQUENCE: 20
tgcaactgat ccgagacaac ttcaaac                                         27

<210> SEQ ID NO 21
<211> LENGTH: 25
<212> TYPE: DNA
<213> ORGANISM: Candida dubliniensis

<400> SEQUENCE: 21
gatcgcaagc gaagcacgaa atgac                                           25

<210> SEQ ID NO 22
<211> LENGTH: 25
<212> TYPE: DNA
<213> ORGANISM: Candida dubliniensis

<400> SEQUENCE: 22
caatgtctgt tcgaccacca ttccc                                           25

<210> SEQ ID NO 23
<211> LENGTH: 25
<212> TYPE: DNA
<213> ORGANISM: Candida dubliniensis

<400> SEQUENCE: 23
agagcgagca cctggtattc ccaag                                           25

<210> SEQ ID NO 24
<211> LENGTH: 24
<212> TYPE: DNA
<213> ORGANISM: Candida dubliniensis

<400> SEQUENCE: 24
cacccaaagc ccagcttaaa ttcc                                            24

<210> SEQ ID NO 25
<211> LENGTH: 28
<212> TYPE: DNA
<213> ORGANISM: Candida dubliniensis

<400> SEQUENCE: 25
tttcaattta gctgactcct taccctgg                                        28

<210> SEQ ID NO 26
<211> LENGTH: 26
<212> TYPE: DNA
<213> ORGANISM: Candida dubliniensis
```

```
<400> SEQUENCE: 26
ttttcggtga ttttgccaag aagttc                                          26

<210> SEQ ID NO 27
<211> LENGTH: 25
<212> TYPE: DNA
<213> ORGANISM: Candida dubliniensis

<400> SEQUENCE: 27
cagcattcat ccgggtaaag tgttg                                           25

<210> SEQ ID NO 28
<211> LENGTH: 25
<212> TYPE: DNA
<213> ORGANISM: Candida dubliniensis

<400> SEQUENCE: 28
caacggatcc aaggtcacca catag                                           25

<210> SEQ ID NO 29
<211> LENGTH: 20
<212> TYPE: DNA
<213> ORGANISM: Candida dubliniensis

<400> SEQUENCE: 29
cgcggtccaa gaagataatc                                                 20

<210> SEQ ID NO 30
<211> LENGTH: 20
<212> TYPE: DNA
<213> ORGANISM: Candida dubliniensis

<400> SEQUENCE: 30
catcatggga tgtaattgct                                                 20

<210> SEQ ID NO 31
<211> LENGTH: 20
<212> TYPE: DNA
<213> ORGANISM: Candida dubliniensis

<400> SEQUENCE: 31
agtgtaagtc ttcgggatac                                                 20

<210> SEQ ID NO 32
<211> LENGTH: 20
<212> TYPE: DNA
<213> ORGANISM: Candida dubliniensis

<400> SEQUENCE: 32
gtgagcgaat agaataattg                                                 20

<210> SEQ ID NO 33
<211> LENGTH: 25
<212> TYPE: DNA
<213> ORGANISM: Candida dubliniensis

<400> SEQUENCE: 33
agctacatct attttcaatg cactc                                           25

<210> SEQ ID NO 34
<211> LENGTH: 20
<212> TYPE: DNA
```

```
<213> ORGANISM: Candida dubliniensis

<400> SEQUENCE: 34
aattgctctg aaacagccag                                          20

<210> SEQ ID NO 35
<211> LENGTH: 25
<212> TYPE: DNA
<213> ORGANISM: Candida dubliniensis

<400> SEQUENCE: 35 tataccccg aattaacaag tgcgc                                     25

<210> SEQ ID NO 36
<211> LENGTH: 25
<212> TYPE: DNA
<213> ORGANISM: Candida dubliniensis

<400> SEQUENCE: 36
cagtgcaggt gctttcgttt accag                                    25

<210> SEQ ID NO 37
<211> LENGTH: 28
<212> TYPE: DNA
<213> ORGANISM: Candida dubliniensis

<400> SEQUENCE: 37
catcagttca attgatgggg ttgttctg                                 28

<210> SEQ ID NO 38
<211> LENGTH: 29
<212> TYPE: DNA
<213> ORGANISM: Candida dubliniensis

<400> SEQUENCE: 38
aaactggcat agcttttttgc attattgcc                               29

<210> SEQ ID NO 39
<211> LENGTH: 24
<212> TYPE: DNA
<213> ORGANISM: Candida dubliniensis

<400> SEQUENCE: 39
atttcgagag gacttggttc gtgc                                     24

<210> SEQ ID NO 40
<211> LENGTH: 24
<212> TYPE: DNA
<213> ORGANISM: Candida dubliniensis

<400> SEQUENCE: 40
ccgtacccaa ataaaactcc cagc                                     24

<210> SEQ ID NO 41
<211> LENGTH: 20
<212> TYPE: DNA
<213> ORGANISM: Candida dubliniensis

<400> SEQUENCE: 41
tacaaagcgg gtgataagga                                          20

<210> SEQ ID NO 42
<211> LENGTH: 18
```

<212> TYPE: DNA
<213> ORGANISM: Candida dubliniensis

<400> SEQUENCE: 42
ggcgcaaaag gaaatagc                                          18

<210> SEQ ID NO 43
<211> LENGTH: 28
<212> TYPE: DNA
<213> ORGANISM: Candida dubliniensis

<400> SEQUENCE: 43
acactgtctt gtcttgtgtc tgaagtcg                               28

<210> SEQ ID NO 44
<211> LENGTH: 25
<212> TYPE: DNA
<213> ORGANISM: Candida dubliniensis

<400> SEQUENCE: 44
ttctctgtgt gtgggccctc agtac                                  25

<210> SEQ ID NO 45
<211> LENGTH: 27
<212> TYPE: DNA
<213> ORGANISM: Candida dubliniensis

<400> SEQUENCE: 45
tcatccatca tatcacaaat cctactg                                27

<210> SEQ ID NO 46
<211> LENGTH: 25
<212> TYPE: DNA
<213> ORGANISM: Candida dubliniensis

<400> SEQUENCE: 46
gttattttga aagttgggga gaggg                                  25

<210> SEQ ID NO 47
<211> LENGTH: 28
<212> TYPE: DNA
<213> ORGANISM: Candida dubliniensis

<400> SEQUENCE: 47
cctacgacat gaacacatca aactactc                               28

<210> SEQ ID NO 48
<211> LENGTH: 25
<212> TYPE: DNA
<213> ORGANISM: Candida dubliniensis

<400> SEQUENCE: 48
tgcttttgtt gaaaacttgc gaaac                                  25

<210> SEQ ID NO 49
<211> LENGTH: 28
<212> TYPE: DNA
<213> ORGANISM: Candida dubliniensis

<400> SEQUENCE: 49
aggctagtcg gtggttaacg gttgtgtg                               28

<210> SEQ ID NO 50

```
<211> LENGTH: 28
<212> TYPE: DNA
<213> ORGANISM: Candida dubliniensis

<400> SEQUENCE: 50
gactcggaat aaacaccatc gccgatgc                                      28

<210> SEQ ID NO 51
<211> LENGTH: 28
<212> TYPE: DNA
<213> ORGANISM: Candida dubliniensis

<400> SEQUENCE: 51
ggtccaatta gaatcgggtc gttccatg                                      28

<210> SEQ ID NO 52
<211> LENGTH: 25
<212> TYPE: DNA
<213> ORGANISM: Candida dubliniensis

<400> SEQUENCE: 52
cgtcatccct tctatctcta acgtg                                         25

<210> SEQ ID NO 53
<211> LENGTH: 24
<212> TYPE: DNA
<213> ORGANISM: Candida dubliniensis

<400> SEQUENCE: 53
atcatatcat gcagcccaac tccg                                          24

<210> SEQ ID NO 54
<211> LENGTH: 24
<212> TYPE: DNA
<213> ORGANISM: Candida dubliniensis

<400> SEQUENCE: 54
cggacgtagt gaaacgattg ttgg                                          24

<210> SEQ ID NO 55
<211> LENGTH: 27
<212> TYPE: DNA
<213> ORGANISM: Candida dubliniensis

<400> SEQUENCE: 55
acaattccca gtaaaccatt ataaaag                                       27

<210> SEQ ID NO 56
<211> LENGTH: 25
<212> TYPE: DNA
<213> ORGANISM: Candida dubliniensis

<400> SEQUENCE: 56
cattcataat ctgatttgta ggctc                                         25

<210> SEQ ID NO 57
<211> LENGTH: 21
<212> TYPE: DNA
<213> ORGANISM: Candida dubliniensis

<400> SEQUENCE: 57
tgctaaacga ccccctcaaa a                                             21
```

```
<210> SEQ ID NO 58
<211> LENGTH: 23
<212> TYPE: DNA
<213> ORGANISM: Candida dubliniensis

<400> SEQUENCE: 58
gtacgacgat catcagcaac caa                                              23

<210> SEQ ID NO 59
<211> LENGTH: 28
<212> TYPE: DNA
<213> ORGANISM: Candida dubliniensis

<400> SEQUENCE: 59
aattaattcg gatagttggg ggagaccg                                         28

<210> SEQ ID NO 60
<211> LENGTH: 25
<212> TYPE: DNA
<213> ORGANISM: Candida dubliniensis

<400> SEQUENCE: 60
attgagctgc tcacttcact gccac                                            25

<210> SEQ ID NO 61
<211> LENGTH: 22
<212> TYPE: DNA
<213> ORGANISM: Candida dubliniensis

<400> SEQUENCE: 61
gcagcgttct tgtgaccgtg ag                                               22

<210> SEQ ID NO 62
<211> LENGTH: 22
<212> TYPE: DNA
<213> ORGANISM: Candida dubliniensis

<400> SEQUENCE: 62
ttgaattgga cagggcttta gg                                               22

<210> SEQ ID NO 63
<211> LENGTH: 30
<212> TYPE: DNA
<213> ORGANISM: Candida dubliniensis

<400> SEQUENCE: 63
tgtggtggag ggtcatccat ttgttggttg                                       30

<210> SEQ ID NO 64
<211> LENGTH: 29
<212> TYPE: DNA
<213> ORGANISM: Candida dubliniensis

<400> SEQUENCE: 64
ggcgaccctc atgcacccta ccaaataaa                                        29

<210> SEQ ID NO 65
<211> LENGTH: 18
<212> TYPE: DNA
<213> ORGANISM: Candida dubliniensis

<400> SEQUENCE: 65
aagtacggat ggttgtta                                                    18
```

-continued

```
<210> SEQ ID NO 66
<211> LENGTH: 22
<212> TYPE: DNA
<213> ORGANISM: Candida dubliniensis

<400> SEQUENCE: 66
tagtcattct gccatctctt at                                              22

<210> SEQ ID NO 67
<211> LENGTH: 28
<212> TYPE: DNA
<213> ORGANISM: Candida dubliniensis

<400> SEQUENCE: 67
ccatgaacaa aaggttaggt ggtgctcc                                        28

<210> SEQ ID NO 68
<211> LENGTH: 25
<212> TYPE: DNA
<213> ORGANISM: Candida dubliniensis

<400> SEQUENCE: 68
ggggagttga atggtgtggt gttac                                           25

<210> SEQ ID NO 69
<211> LENGTH: 24
<212> TYPE: DNA
<213> ORGANISM: Candida dubliniensis

<400> SEQUENCE: 69
tccagcgtca gacatttttc cagt                                            24

<210> SEQ ID NO 70
<211> LENGTH: 18
<212> TYPE: DNA
<213> ORGANISM: Candida dubliniensis

<400> SEQUENCE: 70
tgccccgcgg ttgacagt                                                   18

<210> SEQ ID NO 71
<211> LENGTH: 26
<212> TYPE: DNA
<213> ORGANISM: Candida dubliniensis

<400> SEQUENCE: 71
tggcctctcc cttacaaaat ttgccc                                          26

<210> SEQ ID NO 72
<211> LENGTH: 28
<212> TYPE: DNA
<213> ORGANISM: Candida dubliniensis

<400> SEQUENCE: 72
gggagatgag gggtgattga ggtaatag                                        28

<210> SEQ ID NO 73
<211> LENGTH: 26
<212> TYPE: DNA
<213> ORGANISM: Candida dubliniensis

<400> SEQUENCE: 73
gctccagtac caacgaaaac gacttc                                          26
```

<210> SEQ ID NO 74
<211> LENGTH: 25
<212> TYPE: DNA
<213> ORGANISM: Candida dubliniensis

<400> SEQUENCE: 74
gcatttgaaa actgccaatg tagtc            25

<210> SEQ ID NO 75
<211> LENGTH: 27
<212> TYPE: DNA
<213> ORGANISM: Candida dubliniensis

<400> SEQUENCE: 75
gctgggatag tttagaggca gactgtg          27

<210> SEQ ID NO 76
<211> LENGTH: 25
<212> TYPE: DNA
<213> ORGANISM: Candida dubliniensis

<400> SEQUENCE: 76
cctcaatcac ccctcatctc cctac            25

<210> SEQ ID NO 77
<211> LENGTH: 24
<212> TYPE: DNA
<213> ORGANISM: Candida dubliniensis

<400> SEQUENCE: 77
aagggcaagg aacaagtcac aagt             24

<210> SEQ ID NO 78
<211> LENGTH: 21
<212> TYPE: DNA
<213> ORGANISM: Candida dubliniensis

<400> SEQUENCE: 78
tatcagcgcc ggttttagca c                21

<210> SEQ ID NO 79
<211> LENGTH: 19
<212> TYPE: DNA
<213> ORGANISM: Candida dubliniensis

<400> SEQUENCE: 79
gtgccaactt tctcctgat                   19

<210> SEQ ID NO 80
<211> LENGTH: 22
<212> TYPE: DNA
<213> ORGANISM: Candida dubliniensis

<400> SEQUENCE: 80
agcgattatt aagtctatgt gg               22

<210> SEQ ID NO 81
<211> LENGTH: 22
<212> TYPE: DNA
<213> ORGANISM: Candida dubliniensis

<400> SEQUENCE: 81

-continued gaagcagcga cccaacagat aa				22

<210> SEQ ID NO 82
<211> LENGTH: 22
<212> TYPE: DNA
<213> ORGANISM: Candida dubliniensis

<400> SEQUENCE: 82
ttgagcgaaa ttgggtagag tc				22

<210> SEQ ID NO 83
<211> LENGTH: 30
<212> TYPE: DNA
<213> ORGANISM: Candida dubliniensis

<400> SEQUENCE: 83
tgtccattcc ccaaacttca tacggaccac			30

<210> SEQ ID NO 84
<211> LENGTH: 25
<212> TYPE: DNA
<213> ORGANISM: Candida dubliniensis

<400> SEQUENCE: 84
gaatgctgga aggacttgag aaatg				25

<210> SEQ ID NO 85
<211> LENGTH: 24
<212> TYPE: DNA
<213> ORGANISM: Candida dubliniensis

<400> SEQUENCE: 85
gaaaccaata acaaggaaag agta				24

<210> SEQ ID NO 86
<211> LENGTH: 23
<212> TYPE: DNA
<213> ORGANISM: Candida dubliniensis

<400> SEQUENCE: 86
caatgggaaa agaaatcag tag				23

<210> SEQ ID NO 87
<211> LENGTH: 28
<212> TYPE: DNA
<213> ORGANISM: Candida dubliniensis

<400> SEQUENCE: 87
gacgagagca tgtactcaac tacgtgtc			28

<210> SEQ ID NO 88
<211> LENGTH: 25
<212> TYPE: DNA
<213> ORGANISM: Candida dubliniensis

<400> SEQUENCE: 88
gaatcttgat tgaaatgcga ggaac				25

<210> SEQ ID NO 89
<211> LENGTH: 30
<212> TYPE: DNA
<213> ORGANISM: Candida dubliniensis

<400> SEQUENCE: 89

```
catccaataa cattgattta ctacttttag                                    30

<210> SEQ ID NO 90
<211> LENGTH: 25
<212> TYPE: DNA
<213> ORGANISM: Candida dubliniensis

<400> SEQUENCE: 90
tttttttttc tcaaagattt agcag                                         25

<210> SEQ ID NO 91
<211> LENGTH: 21
<212> TYPE: DNA
<213> ORGANISM: Candida dubliniensis

<400> SEQUENCE: 91
tgtacgatca acccagagtg c                                             21

<210> SEQ ID NO 92
<211> LENGTH: 23
<212> TYPE: DNA
<213> ORGANISM: Candida dubliniensis

<400> SEQUENCE: 92
acatgccatt accaacaaca gtc                                           23

<210> SEQ ID NO 93
<211> LENGTH: 29
<212> TYPE: DNA
<213> ORGANISM: Candida dubliniensis

<400> SEQUENCE: 93
tagctgtatt aaaaaattct ggccgcata                                     29

<210> SEQ ID NO 94
<211> LENGTH: 25
<212> TYPE: DNA
<213> ORGANISM: Candida dubliniensis

<400> SEQUENCE: 94
tctgacaaaa aacctcgtat gaccc                                         25

<210> SEQ ID NO 95
<211> LENGTH: 26
<212> TYPE: DNA
<213> ORGANISM: Candida dubliniensis

<400> SEQUENCE: 95
ctagagctat gttgtgacag tccacc                                        26

<210> SEQ ID NO 96
<211> LENGTH: 25
<212> TYPE: DNA
<213> ORGANISM: Candida dubliniensis

<400> SEQUENCE: 96
cttctggaat tgagccaatc cctag                                         25

<210> SEQ ID NO 97
<211> LENGTH: 28
<212> TYPE: DNA
<213> ORGANISM: Candida dubliniensis
```

```
<400> SEQUENCE: 97
ctagctattc aagcatccgt aggcagtc                                      28

<210> SEQ ID NO 98
<211> LENGTH: 25
<212> TYPE: DNA
<213> ORGANISM: Candida dubliniensis

<400> SEQUENCE: 98
cccatacccg ggtggtgtag tataa                                         25

<210> SEQ ID NO 99
<211> LENGTH: 26
<212> TYPE: DNA
<213> ORGANISM: Candida dubliniensis

<400> SEQUENCE: 99
gtaggcgcta catatgaact tcgtgc                                        26

<210> SEQ ID NO 100
<211> LENGTH: 25
<212> TYPE: DNA
<213> ORGANISM: Candida dubliniensis

<400> SEQUENCE: 100
agataatgtc tgaatgtcat tcggg                                         25

<210> SEQ ID NO 101
<211> LENGTH: 21
<212> TYPE: DNA
<213> ORGANISM: Candida dubliniensis

<400> SEQUENCE: 101
tccaatgggt gctaagatga a                                             21

<210> SEQ ID NO 102
<211> LENGTH: 18
<212> TYPE: DNA
<213> ORGANISM: Candida dubliniensis

<400> SEQUENCE: 102
tcccgcctga ttttgaa                                                  18

<210> SEQ ID NO 103
<211> LENGTH: 28
<212> TYPE: DNA
<213> ORGANISM: Candida dubliniensis

<400> SEQUENCE: 103
ttatttgata gcctaatttc acctgatg                                      28

<210> SEQ ID NO 104
<211> LENGTH: 25
<212> TYPE: DNA
<213> ORGANISM: Candida dubliniensis

<400> SEQUENCE: 104
attaactgac tttgaaccag caatg                                         25

<210> SEQ ID NO 105
<211> LENGTH: 26
<212> TYPE: DNA
<213> ORGANISM: Candida dubliniensis
```

```
<400> SEQUENCE: 105
aacggtcacc tgatgaatag agtggc                                          26

<210> SEQ ID NO 106
<211> LENGTH: 25
<212> TYPE: DNA
<213> ORGANISM: Candida dubliniensis

<400> SEQUENCE: 106
gactgaagcg tccatacttg ggatc                                           25

<210> SEQ ID NO 107
<211> LENGTH: 26
<212> TYPE: DNA
<213> ORGANISM: Candida dubliniensis

<400> SEQUENCE: 107
cccagaagta tccactaggg aacttg                                          26

<210> SEQ ID NO 108
<211> LENGTH: 25
<212> TYPE: DNA
<213> ORGANISM: Candida dubliniensis

<400> SEQUENCE: 108
ttgttctggt caatggtaca gcaac                                           25

<210> SEQ ID NO 109
<211> LENGTH: 28
<212> TYPE: DNA
<213> ORGANISM: Candida dubliniensis

<400> SEQUENCE: 109
cacgcaacta gaatggcatg aatatatg                                        28

<210> SEQ ID NO 110
<211> LENGTH: 25
<212> TYPE: DNA
<213> ORGANISM: Candida dubliniensis

<400> SEQUENCE: 110
agatccggtg tctgtcttat tgctc                                           25

<210> SEQ ID NO 111
<211> LENGTH: 24
<212> TYPE: DNA
<213> ORGANISM: Candida dubliniensis

<400> SEQUENCE: 111
cctgcgttgt aatcatttgt tgtc                                            24

<210> SEQ ID NO 112
<211> LENGTH: 24
<212> TYPE: DNA
<213> ORGANISM: Candida dubliniensis

<400> SEQUENCE: 112
ttactccgcc tttgatccct attt                                            24

<210> SEQ ID NO 113
<211> LENGTH: 25
<212> TYPE: DNA
```

<213> ORGANISM: Candida dubliniensis

<400> SEQUENCE: 113
attaaggagc ttcgtgaggc tgtcg                                    25

<210> SEQ ID NO 114
<211> LENGTH: 25
<212> TYPE: DNA
<213> ORGANISM: Candida dubliniensis

<400> SEQUENCE: 114
catttccttc aaaggcaccg ggatg                                    25

<210> SEQ ID NO 115
<211> LENGTH: 25
<212> TYPE: DNA
<213> ORGANISM: Candida dubliniensis

<400> SEQUENCE: 115
acgttgctta ctggtggcta tgcgg                                    25

<210> SEQ ID NO 116
<211> LENGTH: 25
<212> TYPE: DNA
<213> ORGANISM: Candida dubliniensis

<400> SEQUENCE: 116
aagcttttat tgcggtgaac tgggg                                    25

<210> SEQ ID NO 117
<211> LENGTH: 28
<212> TYPE: DNA
<213> ORGANISM: Candida dubliniensis

<400> SEQUENCE: 117
acatataata gcctaccaca cgccttgc                                 28

<210> SEQ ID NO 118
<211> LENGTH: 25
<212> TYPE: DNA
<213> ORGANISM: Candida dubliniensis

<400> SEQUENCE: 118
tgacattgtg gaaagttaat cgcgg                                    25

<210> SEQ ID NO 119
<211> LENGTH: 28
<212> TYPE: DNA
<213> ORGANISM: Candida dubliniensis

<400> SEQUENCE: 119
tgaaattgga gactaagtgt tgcattcg                                 28

<210> SEQ ID NO 120
<211> LENGTH: 27
<212> TYPE: DNA
<213> ORGANISM: Candida dubliniensis

<400> SEQUENCE: 120
acagtttcca cacaactcag caagaca                                  27

<210> SEQ ID NO 121
<211> LENGTH: 25

<212> TYPE: DNA
<213> ORGANISM: Candida dubliniensis

<400> SEQUENCE: 121
tttgccggga taagctttta ttgcg          25

<210> SEQ ID NO 122
<211> LENGTH: 25
<212> TYPE: DNA
<213> ORGANISM: Candida dubliniensis

<400> SEQUENCE: 122
tttcaggaca ccagaagatg gccac          25

<210> SEQ ID NO 123
<211> LENGTH: 18
<212> TYPE: DNA
<213> ORGANISM: Candida dubliniensis

<400> SEQUENCE: 123
cccccgccgt gaaaaaca                  18

<210> SEQ ID NO 124
<211> LENGTH: 23
<212> TYPE: DNA
<213> ORGANISM: Candida dubliniensis

<400> SEQUENCE: 124
ctacaaacgc cacacccgaa act            23

<210> SEQ ID NO 125
<211> LENGTH: 25
<212> TYPE: DNA
<213> ORGANISM: Candida dubliniensis

<400> SEQUENCE: 125
acctcaacat cgacacagtc gcacc          25

<210> SEQ ID NO 126
<211> LENGTH: 25
<212> TYPE: DNA
<213> ORGANISM: Candida dubliniensis

<400> SEQUENCE: 126
agcagaaacc tcgatgtttg agccg          25

<210> SEQ ID NO 127
<211> LENGTH: 24
<212> TYPE: DNA
<213> ORGANISM: Artificial Sequence
<220> FEATURE:
<223> OTHER INFORMATION: oligonucleotide

<400> SEQUENCE: 127
aactatcaca gtcttgcctg gtga           24

<210> SEQ ID NO 128
<211> LENGTH: 20
<212> TYPE: DNA
<213> ORGANISM: Artificial Sequence
<220> FEATURE:
<223> OTHER INFORMATION: oligonucleotide

<400> SEQUENCE: 128
acagcaccag tgccccattt                                          20

<210> SEQ ID NO 129
<211> LENGTH: 35
<212> TYPE: DNA
<213> ORGANISM: Artificial Sequence
<220> FEATURE:
<223> OTHER INFORMATION: oligonucleotide

<400> SEQUENCE: 129
cccgagctcc aattaacaaa tattaattac aaatg                          35

<210> SEQ ID NO 130
<211> LENGTH: 33
<212> TYPE: DNA
<213> ORGANISM: Artificial Sequence
<220> FEATURE:
<223> OTHER INFORMATION: oligonucleotide

<400> SEQUENCE: 130
tgctctagac caaaatccct ctttctgtat ttg                            33

<210> SEQ ID NO 131
<211> LENGTH: 34
<212> TYPE: DNA
<213> ORGANISM: Artificial Sequence
<220> FEATURE:
<223> OTHER INFORMATION: oligonucleotide

<400> SEQUENCE: 131
cccgagctcc aagtgtattt ttcatctttg gtag                           34

<210> SEQ ID NO 132
<211> LENGTH: 34
<212> TYPE: DNA
<213> ORGANISM: Artificial Sequence
<220> FEATURE:
<223> OTHER INFORMATION: oligonucleotide

<400> SEQUENCE: 132
cccaagcttc tattttgcca ccaaaaccca tctt                           34

<210> SEQ ID NO 133
<211> LENGTH: 36
<212> TYPE: DNA
<213> ORGANISM: Artificial Sequence
<220> FEATURE:
<223> OTHER INFORMATION: oligonucleotide

<400> SEQUENCE: 133
cggggtaccg attgcaagaa gtactacata agagag                         36

<210> SEQ ID NO 134
<211> LENGTH: 37
<212> TYPE: DNA
<213> ORGANISM: Artificial Sequence
<220> FEATURE:
<223> OTHER INFORMATION: oligonucleotide

<400> SEQUENCE: 134
gcccgagctc gcaggtaaaa ttgttcttga ggagccg                        37

<210> SEQ ID NO 135
<211> LENGTH: 41
<212> TYPE: DNA
<213> ORGANISM: Artificial Sequence

```
<220> FEATURE:
<223> OTHER INFORMATION: oligonucleotide

<400> SEQUENCE: 135
acgcgtcgac cccccactga ttacgattat gaatctgatc c                                41

<210> SEQ ID NO 136
<211> LENGTH: 39
<212> TYPE: DNA
<213> ORGANISM: Artificial Sequence
<220> FEATURE:
<223> OTHER INFORMATION: oligonucleotide

<400> SEQUENCE: 136
catgccatgg cccaattcgt atcgatttct tctggtttc                                   39

<210> SEQ ID NO 137
<211> LENGTH: 211
<212> TYPE: PRT
<213> ORGANISM: Candida dubliensis

<400> SEQUENCE: 137
```

Met Ala Arg Leu Ser Gly Gln Ser Ser Gly Arg Gln Thr Gly Gln Gly
1               5                   10                  15

Thr Ser Ala Glu Ala Ile Arg Gln Gln Arg Glu Glu Leu Arg Arg Gln
            20                  25                  30

Arg Glu Leu Arg Leu Gln Gln Gln Gln Ala Glu Arg Gln Gln Gln
        35                  40                  45

Arg Gln Gln Tyr Arg Thr Glu Gln Ser Pro Ile Val Pro Ala Ala Thr
    50                  55                  60

Ser Ser Ser Arg Tyr Ser Gln Phe Gly Ile Tyr Arg Asn Gln Pro Gly
65                  70                  75                  80

Asp Val Val Asp Thr Leu Ala Ser Ser Leu Pro Arg Arg Thr Thr Thr
                85                  90                  95

Thr Arg Pro Glu Val Asn Arg Thr Val Pro Arg Val Lys Lys Arg Tyr
            100                 105                 110

Arg Pro Gly Thr Lys Ala Leu Arg Glu Ile Arg Gln Tyr Gln Lys Ser
        115                 120                 125

Thr Asp Leu Leu Ile Arg Lys Leu Pro Phe Ala Arg Leu Val Arg Glu
    130                 135                 140

Ile Ser Leu Asp Phe Val Gly Pro Ser Tyr Gly Leu Arg Trp Gln Ser
145                 150                 155                 160

Asn Ala Ile Leu Ala Leu Gln Glu Ala Ser Glu Ser Phe Leu Ile His
                165                 170                 175

Leu Leu Glu Asp Thr Asn Leu Cys Ala Ile His Ala Lys Arg Val Thr
            180                 185                 190

Ile Met Gln Lys Asp Ile Gln Leu Ala Arg Arg Ile Arg Gly Gln Ser
        195                 200                 205

Trp Ile Leu
    210

```
<210> SEQ ID NO 138
<211> LENGTH: 212
<212> TYPE: PRT
<213> ORGANISM: Candida dubliensis

<400> SEQUENCE: 138
```

Met Ala Arg Leu Ser Gly Gln Ser Ser Gly Arg Gln Thr Gly Gln Gly
1               5                   10                  15

```
Thr Ser Ala Glu Ala Ile Arg Gln Gln Arg Glu Leu Arg Arg Gln
        20                  25                  30

Arg Glu Leu Arg Leu Gln Gln Gln Gln Ala Glu Arg Gln Arg Gln
        35                  40                  45

Arg Pro Gln Tyr Arg Thr Glu Gln Ser Pro Ile Val Pro Ala Ala Thr
50                  55                  60

Ser Ser Ser Arg Tyr Ser Gln Phe Gly Ile Tyr Arg Asn Gln Pro Gly
65                  70                  75                  80

Asp Val Val Asp Thr Leu Ala Ser Ser Leu Pro Arg Arg Thr Thr Thr
                85                  90                  95

Thr Ala Arg Ser Asp Ile Asn Arg Thr Val Pro Arg Val Lys Lys Arg
            100                 105                 110

Tyr Arg Pro Gly Thr Lys Ala Leu Arg Glu Ile Arg Gln Tyr Gln Lys
            115                 120                 125

Ser Thr Asp Leu Leu Ile Arg Lys Leu Pro Phe Ala Arg Leu Val Arg
            130                 135                 140

Glu Ile Ser Leu Asp Phe Val Gly Pro Ser Tyr Gly Leu Arg Trp Gln
145                 150                 155                 160

Ser Asn Ala Ile Leu Ala Leu Gln Glu Ala Ser Glu Ser Phe Leu Ile
                165                 170                 175

His Leu Leu Glu Asp Thr Asn Leu Cys Ala Ile His Ala Lys Arg Val
            180                 185                 190

Thr Ile Met Gln Lys Asp Ile Gln Leu Ala Arg Arg Ile Arg Gly Gln
            195                 200                 205

Ser Trp Ile Leu
        210

<210> SEQ ID NO 139
<211> LENGTH: 520
<212> TYPE: PRT
<213> ORGANISM: Candida dubliensis

<400> SEQUENCE: 139

Met Tyr Leu Ser Asn Leu Gly Gly Gln Ser Arg Lys Thr Gly Ile Arg
1               5                   10                  15

Pro Lys Thr Asn Leu Lys Thr Asp Lys Tyr Gly Met Glu Asp Val Asp
            20                  25                  30

Asp Phe Phe Glu Asp Asp Asp Asp Arg Ile Asn Lys Ser Lys Gly
        35                  40                  45

Gln Lys Ser Thr Ile Ala Leu Pro Arg Gly Glu Val Ser Asn Tyr
    50                  55                  60

Lys Ser Thr Ile Ser Gln Pro Phe Asn Asn Ile Ala Arg Lys Ile Asn
65                  70                  75                  80

Phe Asn Gln Glu Asp Asp Glu Thr Phe Asn Leu Pro Ser Thr Ser Ser
                85                  90                  95

Ser Ser Ala Thr Val Thr Ala Ser Ser Val Ser Asn Lys Lys Ser Pro
            100                 105                 110

Val Thr Thr Gln Gln Ser Pro Leu Arg Ser Pro Leu Pro Glu Gln Asp
            115                 120                 125

Tyr Asp Tyr Asn Gln Phe Asp Val Glu Glu Asp Tyr Gly Asp Ile Thr
            130                 135                 140

Glu Glu Asp Lys Gln Pro Ser Pro Pro Pro Val Pro Lys Thr Lys
145                 150                 155                 160

Ser Lys Ala Lys Thr Lys Ala Lys Ala Ser Thr Thr Thr Asn Thr Asn
```

165                 170                 175
Thr Lys Ser Thr Lys Ala Ala Ser Ser Phe Thr Lys Lys Met Ala Leu
            180                 185                 190
Gly Lys Thr Lys Arg Leu Pro Ser Ser Phe Asp Ser Val Asn Thr Ser
        195                 200                 205
Ser Val Thr Glu Tyr Tyr Asp Glu Asp Glu Asp Asn Asp Arg Asp
    210                 215                 220
Tyr Gly Glu Ser Gln Gln Asp Ser Ile Glu Asp Ser Met Val Asp Ser
225                 230                 235                 240
Thr Phe Asn Asp Tyr Ser Gln Pro Ser Ser Asn Asn Asn Lys Thr Arg
                245                 250                 255
Arg Lys Ile Ile Lys Glu Ser Pro Leu Pro Ser Pro Pro Pro Asp Asn
            260                 265                 270
Pro Asn Gly Leu Arg Arg Ser Lys Arg Thr Arg Ile Lys Pro Leu Ala
        275                 280                 285
Phe Trp Arg Asn Glu Arg Ile Ile Tyr Ser Lys Asp Leu Asp Tyr Asp
    290                 295                 300
Asp Glu Gln Asp Thr Thr Leu Ala Arg Asp Ile His Asn Ile Pro Leu
305                 310                 315                 320
Gln Ser Ile Lys Glu Val Val His Ile Pro Asp Asn Glu Ser Val Asp
                325                 330                 335
Asn Ser Gly Ser Pro Asn Thr Thr Gly Ala Ala Gly Ser Thr Lys
            340                 345                 350
Thr Arg Ser Asn Arg Lys Arg Thr Tyr Lys Gln Thr Thr Thr Ala
        355                 360                 365
Pro Thr Asp Tyr Asp Tyr Glu Ser Asp Pro Glu Ile Ser Gly Ser Glu
    370                 375                 380
Trp Phe Lys Glu Asp Asn Leu Ser Leu Glu Val Asn Asp Asn Gly Glu
385                 390                 395                 400
Ser Lys Leu Arg Lys Ile Ala Tyr Asn His Lys Gly Gly Asn Tyr Val
                405                 410                 415
Lys Pro Thr Asp Asp Asn Tyr Leu Val Ala Ser Leu Phe Asp Glu Asp
            420                 425                 430
Lys Ser Phe Phe Ala Gly Gly Met Leu Gln Leu Pro Ser Asp Gly Phe
        435                 440                 445
Lys Pro Pro Val Thr Val Thr Gly Ser Thr Tyr Met Phe Asn Val Met
    450                 455                 460
Lys Gly Leu Ile Gln Val Thr Leu Asn Glu Asn Met Phe Val Val Thr
465                 470                 475                 480
Lys Gly Cys Lys Val Gln Ile Pro Glu Gly Asn Glu Tyr Ser Leu Arg
                485                 490                 495
Asn Ile Gly Gln Gly Asp Ala Tyr Leu Phe Phe Val Gln Ile Arg Lys
            500                 505                 510
Pro Glu Glu Ile Asp Thr Asn Trp
        515                 520

<210> SEQ ID NO 140
<211> LENGTH: 516
<212> TYPE: PRT
<213> ORGANISM: Candida dubliensis

<400> SEQUENCE: 140

Met Tyr Leu Ser Asn Leu Gly Gly Gln Ser Arg Lys Thr Gly Ile Arg
1               5                   10                  15

Pro Lys Thr Asn Leu Lys Thr Asp Lys Tyr Gly Met Glu Asp Val Asp
            20                  25                  30

Glu Phe Phe Glu Asp Asp Glu Asp Arg Met Asn Lys Leu Lys Gly
        35                  40                  45

Gln Lys Leu Thr Ile Ser Leu Pro Arg Ala Glu Glu Val Ser Lys Tyr
    50                  55                  60

Lys Ser Thr Ile Ser Gln Pro Phe Asn Asn Ile Ala Arg Lys Ile Asn
65                  70                  75                  80

Phe Asn Gln Glu Asp Asp Glu Thr Phe Asn Leu Pro Ser Thr Ser Thr
                85                  90                  95

Ser Ser Ala Thr Ala Thr Thr Ser Ser Val Ser Asn Lys Lys Ser Pro
                100                 105                 110

Val Thr Thr Gln Gln Ser Pro Leu Arg Ser Pro Leu Glu Gln Asp
            115                 120                 125

Tyr Asp Tyr Asn Gln Phe Asp Val Glu Glu Asp Tyr Gly Asp Ile Thr
        130                 135                 140

Glu Glu Asp Arg Gln Pro Ser Pro Pro Pro Pro Ser Val Pro Lys
145                 150                 155                 160

Ser Asn Thr Glu Thr Lys Ser Asn Thr Lys Ser Ser Lys Ala Ala Ser
                165                 170                 175

Ser Phe Thr Lys Lys Met Ala Leu Gly Lys Thr Lys Lys Leu Pro Ser
            180                 185                 190

Ser Phe Asp Ser Ala Asn Thr Thr Ser Val Thr Glu Tyr Phe Asp Glu
        195                 200                 205

Glu Glu Asp Asp Asp Asp Arg Asp Tyr Gly Glu Ser Gln Gln Asp
210                 215                 220

Ser Ile Glu Asp Ser Met Met Asp Ser Thr Phe Asn Asp Tyr Ser Gln
225                 230                 235                 240

Pro Ser Ser Asn Ile Lys Ser Lys Thr Arg Arg Lys Ile Ile Lys Glu
            245                 250                 255

Ser Pro Leu Pro Ser Pro Pro Asp Asn Pro Asn Gly Leu Arg Arg
        260                 265                 270

Ser Lys Arg Thr Arg Ile Lys Pro Leu Ala Phe Trp Arg Asn Glu Arg
    275                 280                 285

Ile Ile Tyr Ser Lys Asp Leu Asp Tyr Asp Asp Glu Gln Asp Thr Thr
290                 295                 300

Leu Ala Arg Asp Ile His Asn Ile Pro Leu Gln Leu Ile Lys Glu Val
305                 310                 315                 320

Val His Ile Pro Asp Asn Glu Thr Val Asp Asn Ser Arg Ser Pro Asn
            325                 330                 335

Ser Thr Thr Gly Ala Ala Ala Ser Gly Ser Thr Lys Arg Arg Leu Asn
        340                 345                 350

Arg Lys Arg Thr Tyr Lys Gln Ser Ser Val Val Ala Pro Thr Asp Tyr
    355                 360                 365

Asp Tyr Glu Ser Asp Pro Glu Ile Ser Gly Ser Glu Trp Phe Lys Glu
        370                 375                 380

Asp Asn Leu Leu Leu Glu Val Asn Asp Asn Gly Glu Ser Arg Val Arg
385                 390                 395                 400

Lys Ile Ala Tyr Asn His Lys Gly Gly Asn Tyr Val Lys Pro Thr Asp
            405                 410                 415

Asp Asn Tyr Leu Val Ala Ser Leu Phe Asp Glu Asp Lys Ser Phe Phe
        420                 425                 430

Ala Gly Gly Met Leu Gln Leu Pro Val Asp Gly Phe Lys Pro Pro Val

-continued

```
                435                 440                 445
Thr Val Thr Gly Ser Thr Tyr Met Phe Asn Val Met Lys Gly Leu Ile
        450                 455                 460

Gln Val Thr Leu Asn Glu Asn Met Phe Val Val Thr Lys Gly Cys Lys
465                 470                 475                 480

Val Gln Ile Pro Glu Gly Asn Glu Tyr Ser Leu Arg Asn Ile Gly Gln
                485                 490                 495

Gly Asp Ala Tyr Leu Phe Phe Val Gln Ile Arg Lys Pro Glu Glu Ile
            500                 505                 510

Asp Thr Asn Trp
        515
```

POLYNUCLEOTIDE SEQUENCES OF *CANDIDA DUBLINIENSIS* AND PROBES FOR DETECTION

FIELD OF THE INVENTION

Figure 1:
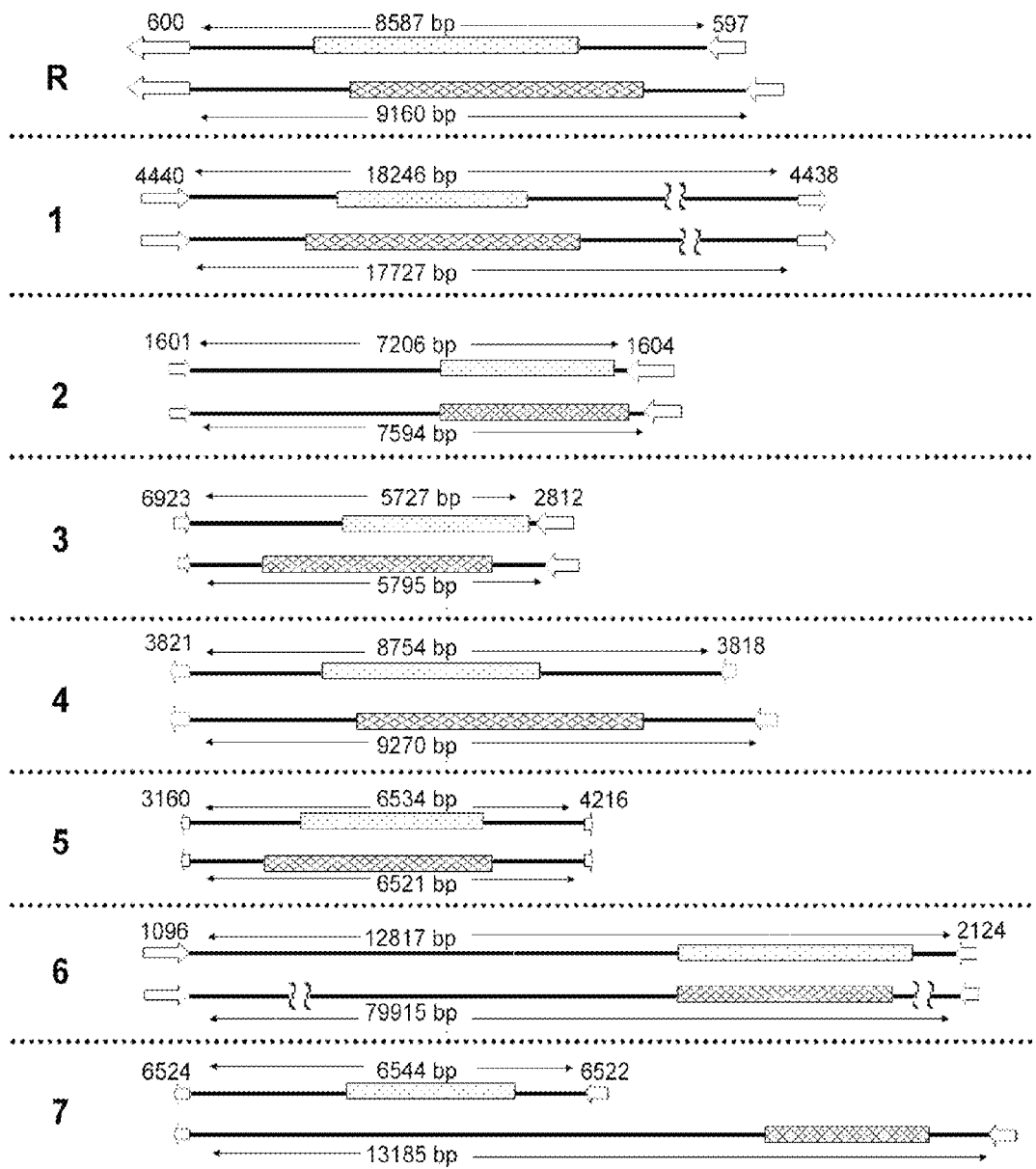

The present invention relates to identification of centromeric sequences of *Candida dubliniensis* and localization of CdCse4p centromeric histone to the identified region. Also the present invention relates to distinguishing *Candida dubliniensis* from other members of genus *Candida*.

REFERENCE TO SEQUENCE LISTING

A Sequence Listing submitted as an ASCII text file via EFS-Web is hereby incorporated by reference in accordance with 35 U.S.C. §1.52(e). The name of the ASCII text file for the Sequence Listing is 22089435_1.TXT, the date of creation of the ASCII text file is Nov. 18, 2015, and the size of the ASCII text file is 73.5 KB.

BACKGROUND AND PRIOR ART OF THE INVENTION

*Candida* is a genus of yeasts. Many species of this genus are endosymbionts of animal hosts including humans. While usually living as commensals, some *Candida* species have the potential to cause disease. Clinically, the most significant member of the genus is *Candida albicans*, which can cause infections (called candidiasis or thrush) in humans and other animals, especially in immunocompromised patients. Many *Candida* species are members of gut flora in animals, including *C. albicans* in mammalian hosts, whereas others live as endosymbionts in insect hosts.

Among the other important members of this genus *Candida dubliniensis* is a significant pathogenic fungi. *Candida dubliniensis* is an organism often associated with AIDS patients but can be associated with immunocompetent patients as well. It is a germ cell-positive yeast of the genus *Candida*, similar to *Candida albicans* but it forms a different cluster upon DNA fingerprinting. It appears to be particularly adapted for the mouth but can be found at very low rates in other anatomical sites. *Candida dubliniensis* is found all around the world. The species was only described in 1995. It is thought to have been previously identified as *Candida albicans*. Retrospective studies support this, and have given an indication of the prevalence of *C. dubliniensis* as a pathogen.

This isolate is germ tube positive which accounts for its historic miss-identification as *C. albicans*. The most useful test for distinguishing *C. dubliniensis* from *C. albicans* is to culture at 42° C. Most *C. albicans* grows well at this temperature, but most *C. dubliniensis* do not. There are also significant differences in the chlamydiospores between *C. albicans* and *C. dubliniensis* although they are otherwise phenotypically very similar.

A study done in Europe of 2,589 isolates that were originally reported as *C. albicans* revealed that 52 of them (2.0%) were actually *C. dubliniensis*. Most of these isolates were from oral or faecal specimens from HIV positive patients, though one vaginal and two oral isolates were from healthy volunteers. Another study done in the United States, used 1,251 yeasts previously identified as *C. albicans*, it found 15 (1.2%) were really *C. dubliniensis*. Most of these samples were from immunocompromised individuals: AIDS, chemotherapy, or organ transplant patients. The yeast was most often recovered from respiratory, urine and stool specimens. The Memorial Sloan-Kettering Cancer Center also did several studies, both retrospective, and current. In all 974 germ-tube positive yeasts, 22 isolates (2.3%) from 16 patients were *C. dubliniensis*.

Molecular analysis show that *C. dubliniensis* is distinct from *C. albicans* by 13-15 nucleotides in the ribosomal RNA gene sequences. Early reports purported that *C. dubliniensis* was responsible for fluconazole-resistant thrush but susceptibility studies reveal that its categorical distribution is similar to *C. albicans* with isolates ranging from susceptible to resistant.

Previous literature describes that Centromeric DNA sequences in the pathogenic yeast *Candida albicans* are all different and unique (Sanyal et al, 2004). The Cse4p-containing centromere regions of *Candida albicans* have unique and different DNA sequences on each of the eight chromosomes. However similar studies have not been carried out in *C. dubliniensis*.

Amongst the most prevalent methods of distinguishing *C. dubliniensis* from *C. albicans* are the compositions and methods for the detection and identification of species of *Candida*, in particular, to nucleic acid probes that specifically hybridize to the internal transcribed spacer 2 (ITS2) of the ribosomal DNA (rDNA) repeat region of *Candida* species (such as *C. albicans* and *C. dubliniensis*).

Another method of identification includes use of multiplex PCR which uses essentially three factors: (i) the elevated number of copies from the rRNA genes (about 100 copies per genome), (ii) the differences regarding the sizes of the ITS regions and (iii) the elevated variability of these region sequences among the different species of *Candida*. Thus, this technique is based on the amplification of DNA fragments specific of the internal transcribed spacer regions 1 (ITS-I) and 2 (ITS-2) by multiplex PCR. The methodology uses the combination of two universal primers and seven specific primers for each one of the *Candida* species studied, in a single PCR reaction, originating two fragments of different sizes for each species (European publication no: EP1888745).

Most techniques used so far distinguish *C. dubliniensis* from other species by identification of rDNA or RNA sequences of the genome.

The genome of *C. dubliniensis* has not been sequenced completely and the work to find out more information about its genome is in progress.

However the present invention has been able to assign centromeric functions to the sequence identified and these centromeric sequences are further used to distinguish *Candida dubliniensis* from other members of the genus based on the localization of histone proteins CdCse4p.

Faithful chromosome segregation during mitosis and meiosis in eukaryotes is performed by a dynamic interaction between spindle microtubules and kinetochores. The kinetochore is a proteinaceous structure that forms on a specific DNA locus on each chromosome, termed as the centromere (CEN). Centromeres have been cloned and characterized in several organisms from yeasts to humans. Interestingly, there is no centromere-specific cis-acting DNA sequence that is conserved across species (1). However, centromeres in all eukaryotes studied to date assemble into specialized chromatin containing a histone H3 variant protein in the CENP-A/Cse4p family. Members of this family are called centromeric histones (CenH3s) and are regarded as possible epigenetic markers of CEN identity (1, 2). The *Saccharomyces cerevisiae* centromere, the most intensively studied budding yeast centromere, is a well defined, short 125 bp) region (hence called a "point" centromere), and consists of two conserved consensus sequences (Centromere DNA Elements; CDEs), CDEI (8 bp) and CDEIII (25 bp) separated by CDEII, a 78-86 bp non-conserved AT-rich (>90%) "spacer"-sequence (3). CDEI is not absolutely necessary for mitotic centromere function (4). Retention of a portion of CDEII is essential for CEN activity, but changes in length or base composition of CDEII cause only partial inactivation (4, 5). The *S. cerevisiae* CenH3, ScCse4p, has been shown to bind to a single nucleosome containing the non-conserved CDEII and to flanking CDEI and CDEIII regions (6). CDEIII is absolutely essential: centromere function is completely inactivated by deletion of CDEIII, or even by single base substitutions in the central CCG sequence. Centromeres of most other eukaryotes, including the fission yeast *Schizosaccharomyces pombe*, are much longer and more complex than those of *S. cerevisiae* and are called "regional" centromeres (3). The centromeres of *S. pombe* are 40-110 kb in length, and organized into distinct classes of repeats which are further arranged into a large inverted repeat. The non-repetitive central region, also known as the central core (cc), contains a 4-7 kb non-homologous region that is not conserved in all three chromosomes (3). The CenH3 homolog in *S. pombe*, Cnp1p, binds to the central core and the inner repeats (7). However, the central domain alone cannot assemble centromere chromatin de novo, but requires the cis-acting dg/K repeat present at the outer repeat array to promote de novo centromere assembly (8, 9). Several experiments suggest that unlike in *S. cerevisiae*, no unique conserved sequence within *S. pombe* centromeres is sufficient for establishment and maintenance of centromere function, although flanking repeats play a crucial role in establishing heterochromatin that is important for centromere activity (10). Studies in a pathogenic budding yeast, *Candida albicans*, containing regional centromeres suggest that each of its eight chromosomes contains a different, 3-5 kb, non-conserved DNA sequence that assembles into Cse4p-rich centromeric chromatin (11, 12). *C. albicans* centromeres partly resemble those of *S. pombe* but lack any pericentric repeat that is common to all of its eight centromeres (12). Therefore, the mechanisms by which CenH3s confer centromere identity, are deposited at the right location, and are epigenetically propagated for several generations in *C. albicans* without any centromere-specific DNA sequence remain largely unknown.

OBJECTIVES OF THE INVENTION

The main objective of the present invention is to obtain a polynucleotide sequence. Another main objective of the present invention is to obtain sets of primers for amplification of the polynucleotide sequences of *Candida dubliniensis*.

Yet another main objective of the present invention is to obtain a process for identification of centromeric sequences of *Candida* dubliniensis Still another main objective of the present invention is to obtain a method of distinguishing *Candida dubliniensis* from *Candida albicans*.

Still another main objective of the present invention is to obtain a kit for identification of *Candida dubliniensis*.

STATEMENT OF THE INVENTION

Accordingly, the present invention relates to a polynucleotide sequence having SEQ ID NO 1, 2, 3, 4, 5, 6, 7 or 8; a set of 20 primers having SEQ ID NOS. 9, 11, 13, 15, 17, 19, 21, 23, 25 and 27 as forward primers and SEQ ID NOS. 10, 12, 14, 16, 18, 20, 22, 24, 26 and 28 as corresponding reverse primers respectively; a set of 14 primers having SEQ ID NOS. 29, 31, 33, 35, 37, 39 and 41 as forward primers and SEQ ID NOS. 30, 32, 34, 36, 38, 40 and 42 as corresponding reverse primers respectively; a set of 10 primers having SEQ ID NOS. 43, 45, 47, 49 and 51 as forward primers and SEQ ID NOS. 44, 46, 48, 50 and 52 as corresponding reverse primers respectively; a set of 16 primers having SEQ ID NOS. 53, 55, 57, 59, 61, 63, 65 and 67 as forward primers and SEQ ID NOS. 54, 56, 58, 60, 62, 64, 66 and 68 as corresponding reverse primers respectively; a set of 10 primers having SEQ ID NOS. 69, 71, 73, 75 and 77 as forward primers and SEQ ID NOS. 70, 72, 74, 76 and 78 as corresponding reverse primers respectively; a set of 16 primers having SEQ ID NOS. 79, 81, 83, 85, 87, 89, 91 and 93 as forward primers and SEQ ID NOS. 80, 82, 84, 86, 88, 90, 92 and 94 as corresponding reverse primers respectively; a set of 18 primers having SEQ ID NOS. 95, 97, 99, 101, 103, 105, 107, 109 and 111 as forward primers and SEQ ID NOS. 96, 98, 100, 102, 104, 106, 108, 110 and 112 as corresponding reverse primers respectively; a set of 14 primers having SEQ ID NOS. 114, 116, 118, 120, 122, 123 and 126 as forward primers and SEQ ID NOS. 113, 115, 117, 119, 121, 124 and 125 as corresponding reverse primers respectively; a process of identification of centromeric sequences of *Candida dubliniensis*, said method comprising steps of a) identifying putative Cse4p binding region and b) amplifying the putative Cse4p binding region to identify centromeric sequences of the *Candida dubliniensis*; a method of distinguishing *Candida dubliniensis* from *Candida albicans* in a sample, said method comprising steps of a) isolating DNA from the organism in the sample and b) amplifying the Cse4p binding regions with primers capable of amplifying said regions in the *Candida dubliniensis* to distinguish it from *Candida albicans* and a kit for identification of *Candida dubliniensis* comprising set of primers having SEQ ID NOS. 9 to 126.

BRIEF DESCRIPTION OF ACCOMPANYING SEQUENCE LISTINGS

SEQ ID NOS. 1, 2, 3, 4, 5, 6, 7 and 8: Centromeric polynucleotide sequences for Chromosome 1, 2, 3, 4, 5, 6, 7 and 8 of *Candida dubliniensis*.

SEQ ID NOS. 9, 11, 13, 15, 17, 19, 21, 23, 25 and 27: Forward Primers for Chromosome 1 of *Candida dubliniensis*.

SEQ ID NOS. 10, 12, 14, 16, 18, 20, 22, 24, 26 and 28: Reverse Primers for Chromosome 1 of *Candida dubliniensis*.

SEQ ID NOS. 29, 31, 33, 35, 37, 39 and 41: Forward Primers for Chromosome 2 of *Candida dubliniensis*.

SEQ ID NOS. 30, 32, 34, 36, 38, 40 and 42: Reverse Primers for Chromosome 2 of *Candida dubliniensis*.

SEQ ID NOS. 43, 45, 47, 49 and 51: Forward Primers for Chromosome 3 of *Candida dubliniensis*.

SEQ ID NOS. 44, 46, 48, 50 and 52: Reverse Primers for Chromosome 3 of *Candida dubliniensis*.

SEQ ID NOS. 53, 55, 57, 59, 61, 63, 65 and 67: Forward Primers for Chromosome 4 of *Candida dubliniensis*.

SEQ ID NOS. 54, 56, 58, 60, 62, 64, 66 and 68: Reverse Primers for Chromosome 4 of *Candida dubliniensis*.

SEQ ID NOS. 69, 71, 73, 75 and 77: Forward Primers for Chromosome 5 of *Candida dubliniensis*.

SEQ ID NOS. 70, 72, 74, 76 and 78: Reverse Primers for Chromosome 5 of *Candida dubliniensis*.

SEQ ID NOS. 79, 81, 83, 85, 87, 89, 91 and 93: Forward Primers for Chromosome 6 of *Candida dubliniensis*.

SEQ ID NOS. 80, 82, 84, 86, 88, 90, 92 and 94: Reverse Primers for Chromosome 6 of *Candida dubliniensis*.

SEQ ID NOS. 95, 97, 99, 101, 103, 105, 107, 109 and 111: Forward Primers for Chromosome 7 of *Candida dubliniensis*.

SEQ ID NOS. 96, 98, 100, 102, 104, 106, 108, 110 and 112: Reverse Primers for Chromosome 7 of *Candida dubliniensis*.

SEQ ID NOS. 114, 116, 118, 120, 122, 123 and 126: Forward Primers for Chromosome 8, also known as Chromosome R, of *Candida dubliniensis*.

SEQ ID NOS. 113, 115, 117, 119, 121, 124 and 125: Reverse Primers for Chromosome 8, also known as Chromosome R, of *Candida dubliniensis*.

BRIEF DESCRIPTION OF ACCOMPANYING FIGURES

FIG. 1: Orthologous Cse4p-rich centromere regions in *C. albicans* and *C. dubliniensis*.

Figure 2:
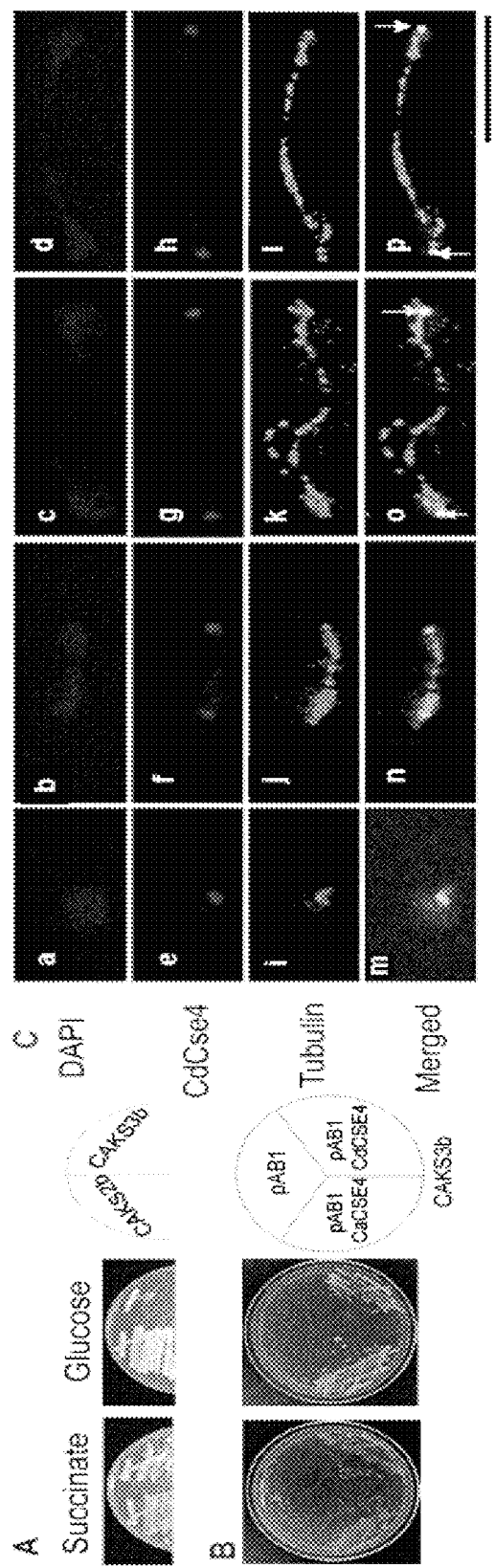

FIG. 2: Localization of CdCse4p at the kinetochore of *C. dubliniensis*. (A) CAKS3b can grow on succinate medium but is unable to grow on glucose medium. (B) CAKS3b is transformed with pAB1, pAB1CaCSE4 or pAB1CdCSE4. These transformants were streaked on plates containing complete media lacking histidine with succinate or glucose as the carbon source. (C) *C. dubliniensis* strain Cd36 was grown in YPD and fixed. Fixed cells were stained with DAPI (a-d), anti-Ca/CdCse4p (e-h) and anti-tubulin (i-l) antibodies. The intense dot-like CdCse4p signals were observed in unbudded (e) and at different stages of budded cells (f-h). Corresponding spindle structures are shown by co-immunostaining with anti-tubulin antibodies (i-l). Arrows indicate the position of spindle pole bodies in large-budded cells at anaphase. (Bar=10 μm).

Figure 3:
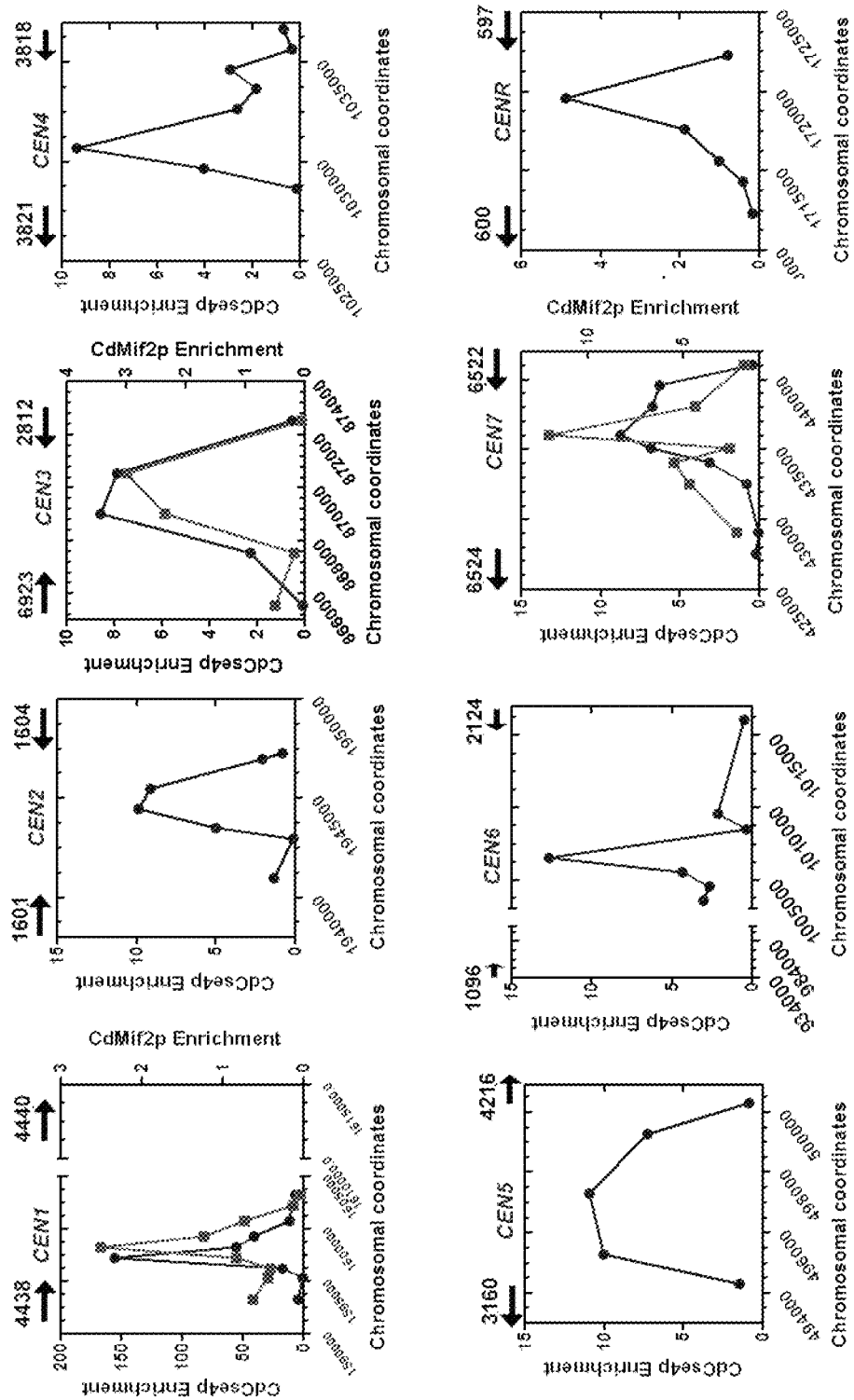

FIG. 3: Binding of two evolutionarily conserved key kinetochore proteins, CdCse4p (CENP-A homolog) and CdMif2p (CENP-C homolog) to the same regions of different *C. dubliniensis* chromosomes.

Figure 4:
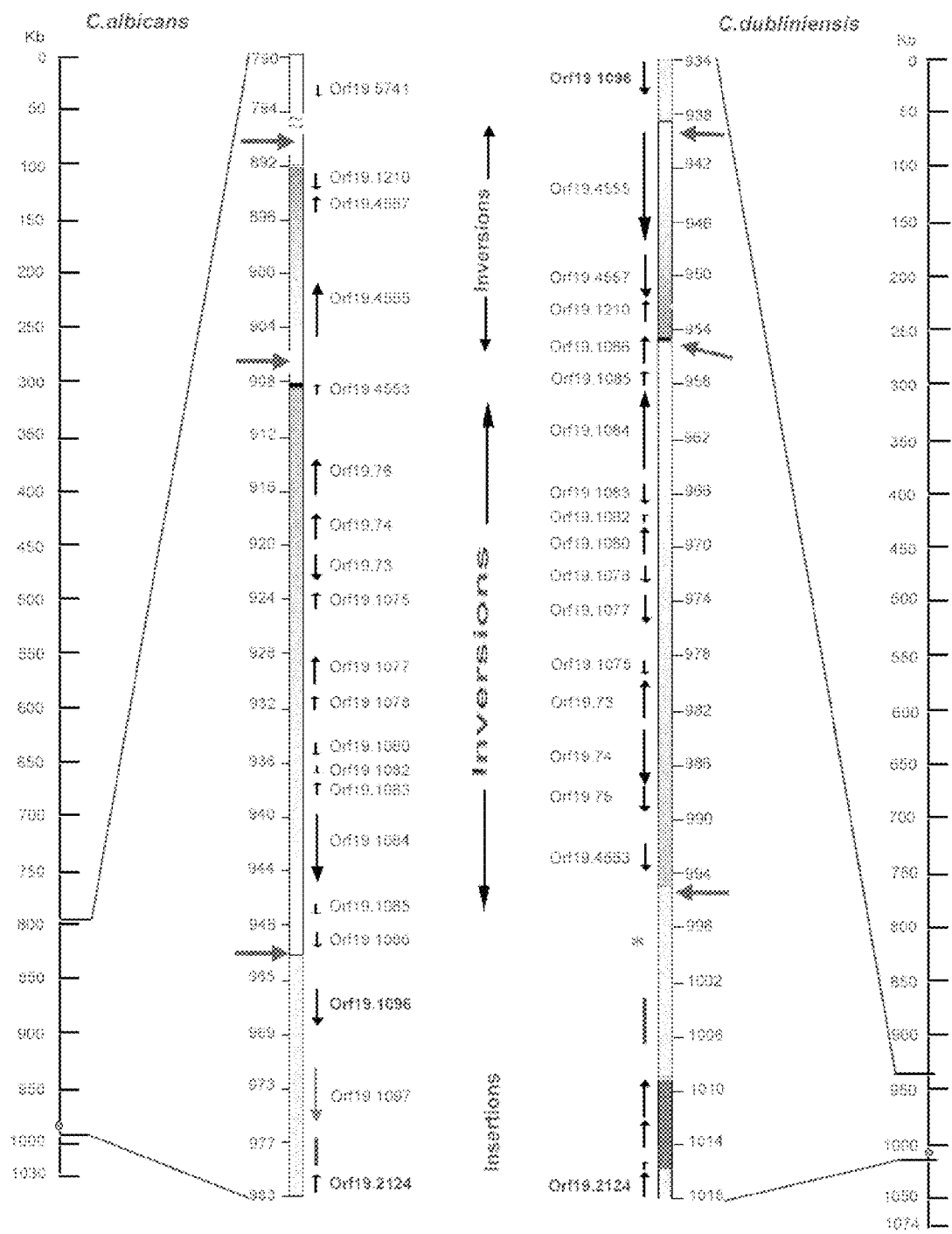

FIG. 4: Comparative analysis of CEN6 region of *C. albicans* and its orthologous region in *C. dubliniensis* showing genome rearrangement.

Figure 5:
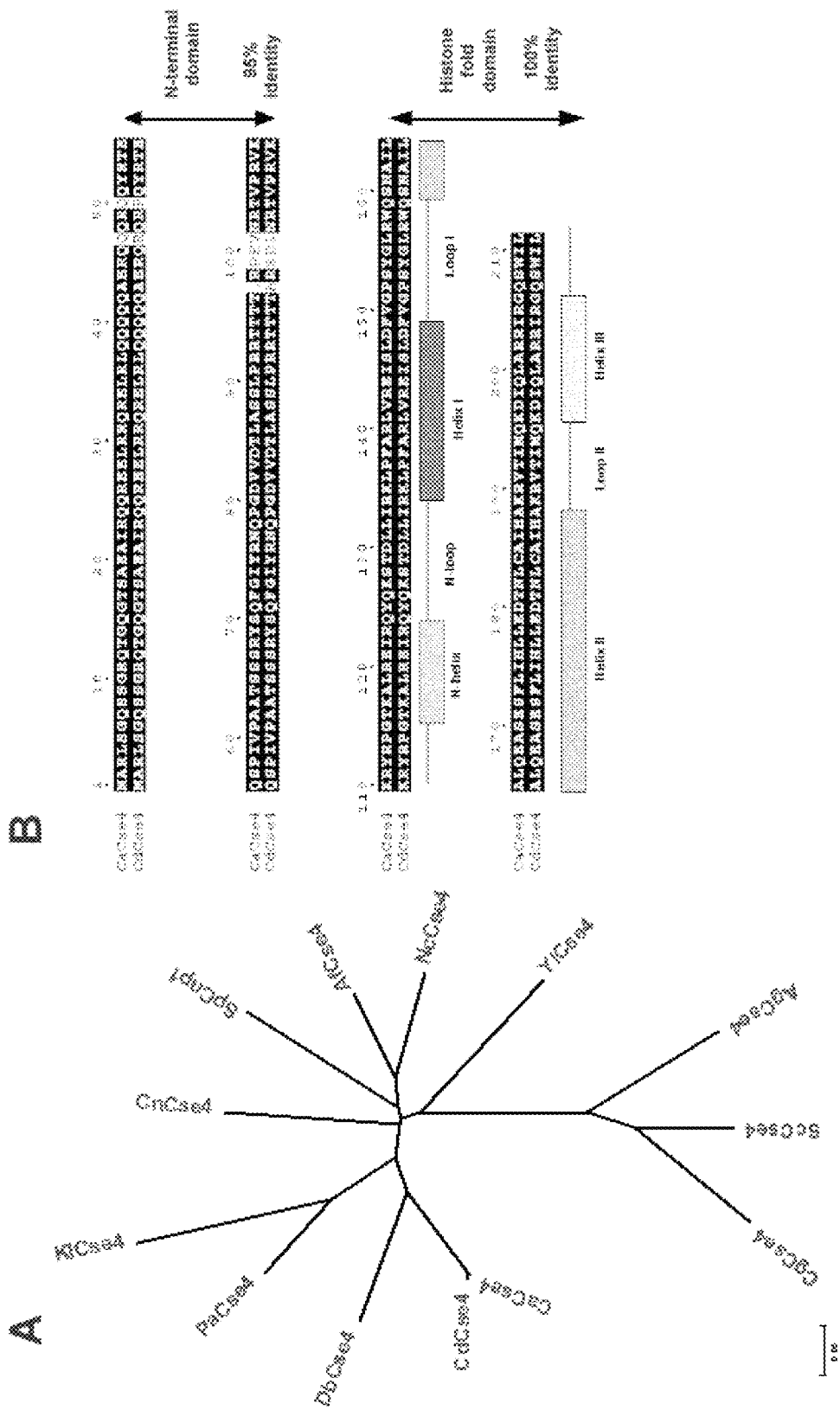

FIG. 5: The centromeric histone in *C. dubliniensis*, CdCse4p, belongs to the Cse4p/CENP-A family. (A) Phylogenetic tree of the Cse4 protein sequences in yeasts in the radiation format using neighbor-joining method of Molecular Evolutionary Genetics Analysis version 3.1 (MEGA) software showing Cse4 proteins in *C. albicans* and *C. dubliniensis* are highly related. Ca—*Candida albicans*, Cd—*Candida dubliniensis*, Db—*Debaryomyces hansenii*, Pa—*Pichia angusta*, Kl—*Kluyveromyces lactis*, Cn—*Cryptococcus neoformans*, Sp—*Schizosaccharomyces pombe*, Af—*Aspergillus fumigatus*, Nc—*Neurospora crassa*, Yl—*Yarrowia lipolytica*, Ag—*Ashbya gossypii*, Sc—*Saccharomyces cerevisiae*, Cg—*Candida glabrata*. (B) Pairwise comparison of Cse4p in *C. albicans* (SEQ ID NO: 137) and *C. dubliniensis* (SEQ ID NO: 138) showing homologies in N-terminal region and C-terminal histone fold domain.

Figure 6:
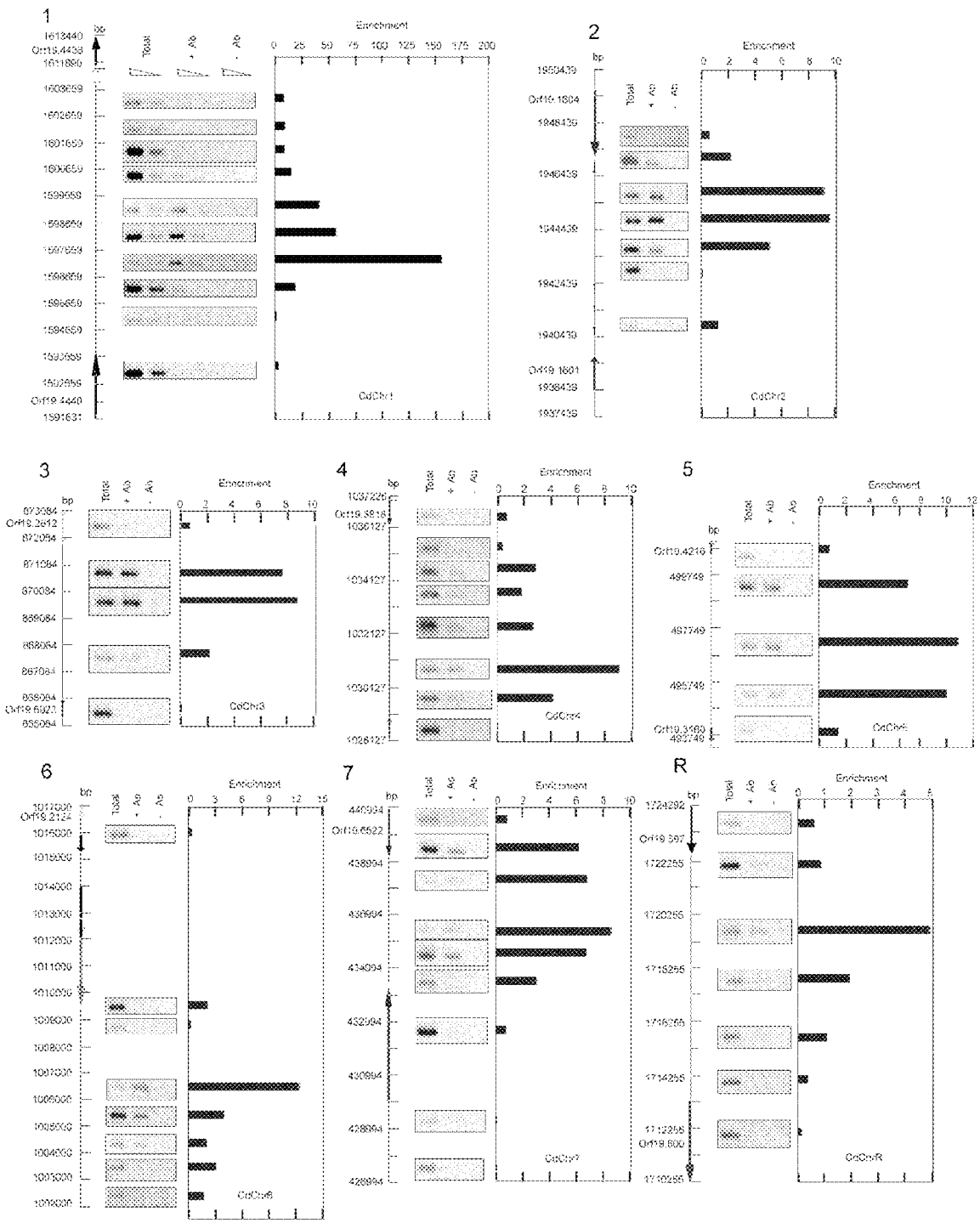

FIG. 6: Relative enrichment profiles of CdCse4p in various *C. dubliniensis* chromosomes.

Figure 7:
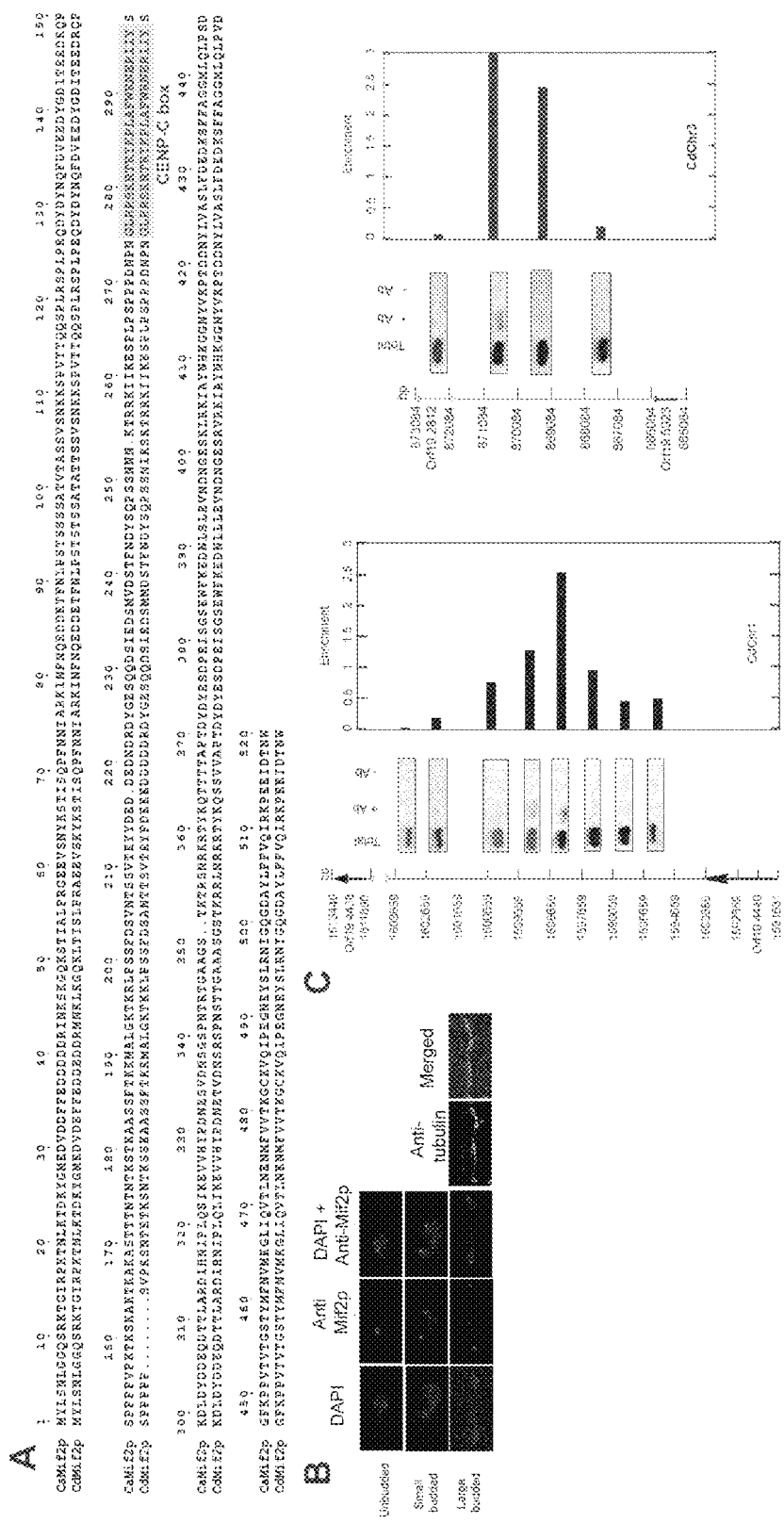

FIG. 7: The CENP-C homolog in *C. dubliniensis* (CdMif2p) is co-localized with CdCse4p. (A) Sequence alignment of CaMif2p (SEQ ID NO: 139) and CdMif2p (SEQ ID NO: 140) showing the conserved CENP-C block (box) (B) Localization of CdMif2p at various stages of cell cycle in *C. dubliniensis*. (C) ChIP enrichment profiles of CdMif2p on chromosomes 1 and 3 in the strain CDM1 by determining the intensities of (+Ab) minus (−Ab) signals divided by the total DNA signals and are normalized to a value of 1 for the same obtained using primers for a non-centromeric locus (CdLEU2).

Figure 8:
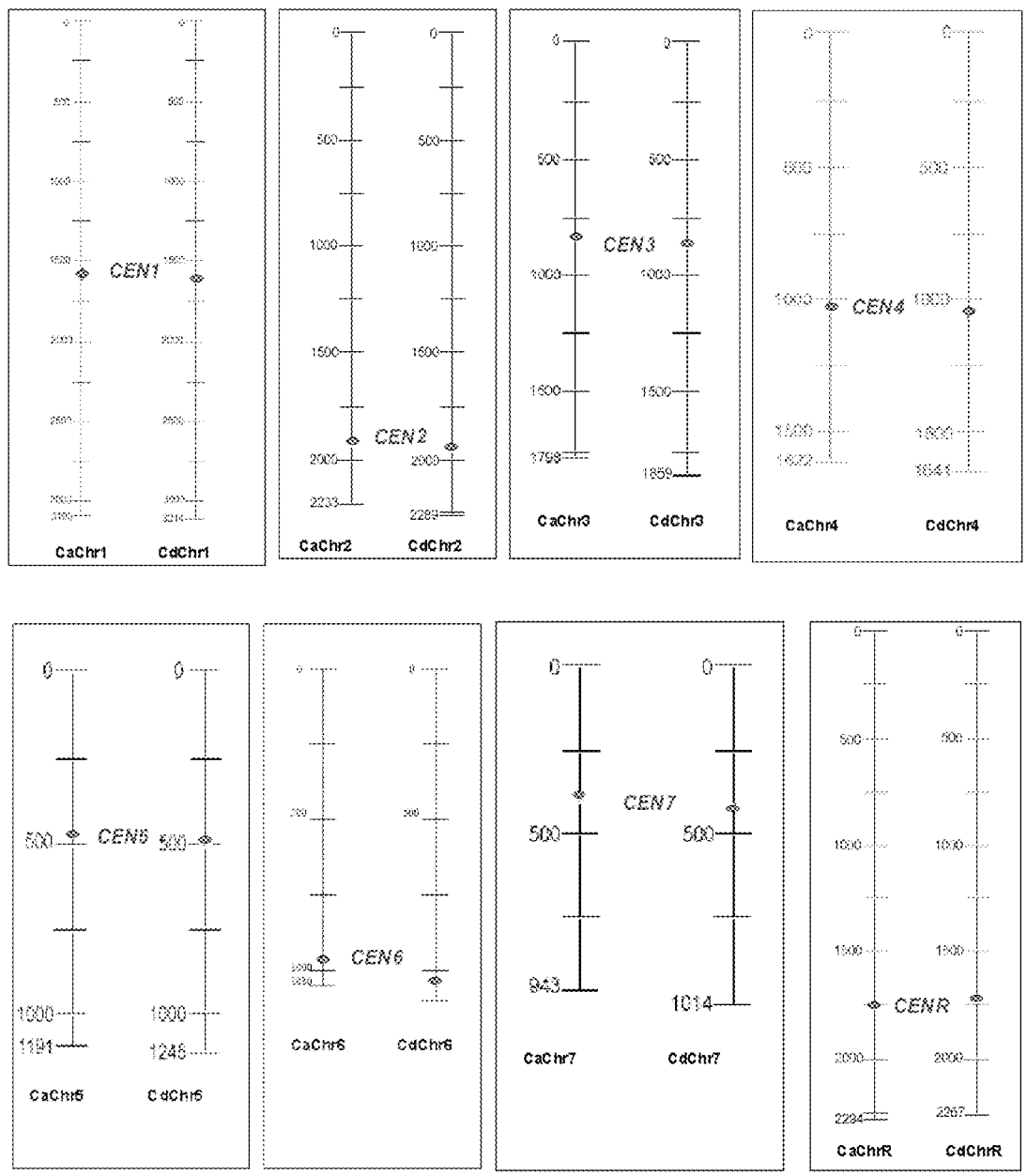

FIG. 8: Relative chromosomal positions of Cse4p-binding regions in *C. albicans* and *C. dubliniensis*.

Figure 9:
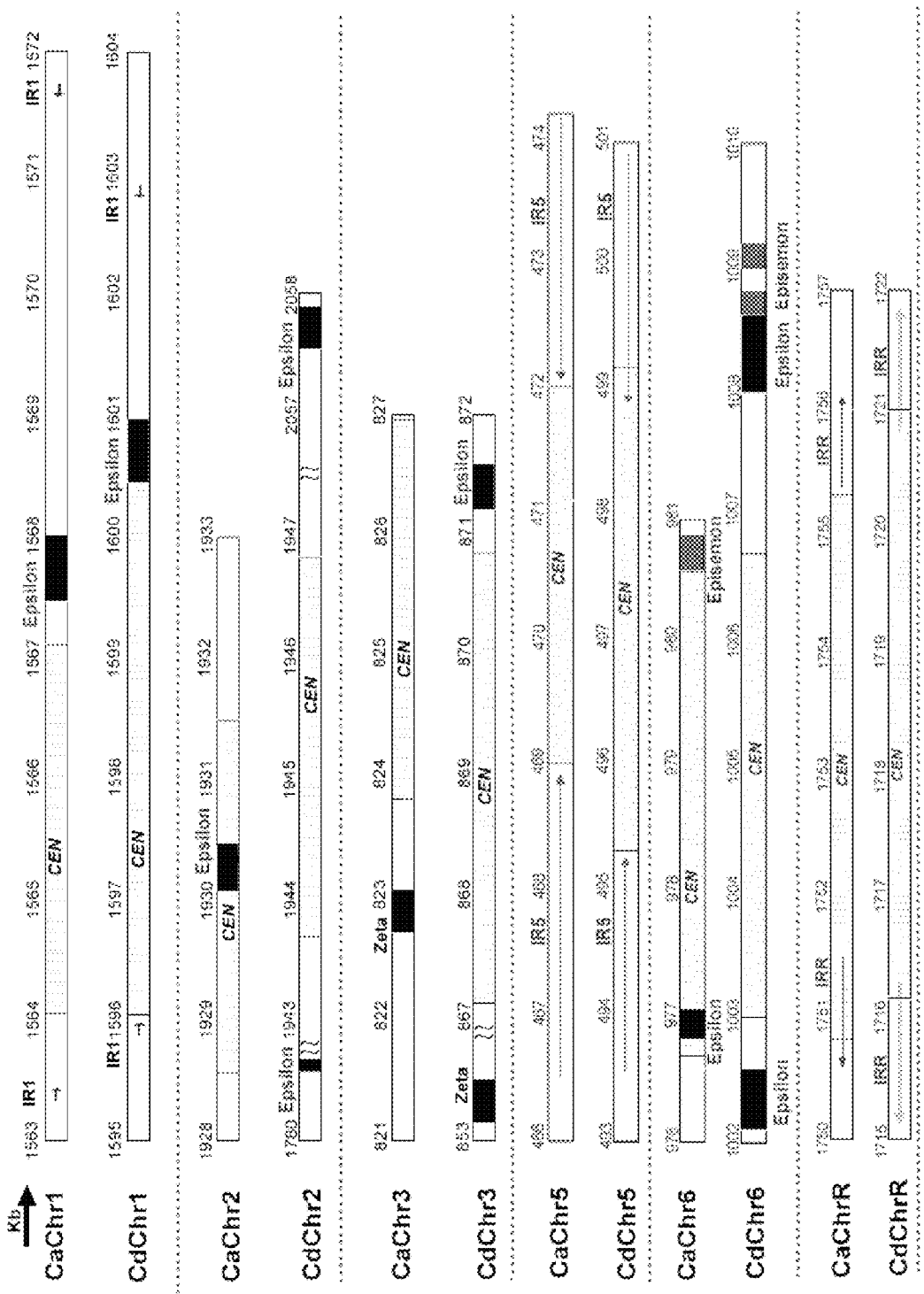

FIG. 9: Conserved blocks in the pericentric regions of various chromosomes of *C. dubliniensis* and *C. albicans*.

BRIEF DESCRIPTION OF ACCOMPANYING TABLES

Table 1: Comparison of the amino acid sequence homology of the ORFs flanking the CEN regions in *C. albicans* and *C. dubliniensis*

Table 2: List of PCR Primers used for ChIP assays.

Table 2B: List of PCR primers used for Cse4 complementation experiments

Table 3: Sequence coordinates of the Cse4p-binding and the pericentric regions in all the chromosomes of *C. albicans* and *C. dubliniensis*

Table 4: List of strains

Table 5: Comparison of mutation rates in Cse4p-binding and other genomic noncoding regions in *C. albicans* and *C. dubliniensis*.

Table 6: Homology between the repeats in the pericentric region of *C. albicans* and *C. dubliniensis*

DETAILED DESCRIPTION OF THE INVENTION

The present invention relates to a polynucleotide sequence having SEQ ID NO 1, 2, 3, 4, 5, 6, 7 or 8.

The present invention also relates to a set of 20 primers having SEQ ID NOS. 9, 11, 13, 15, 17, 19, 21, 23, 25 and 27 as forward primers and SEQ ID NOS. 10, 12, 14, 16, 18, 20, 22, 24, 26 and 28 as corresponding reverse primers respectively.

In another embodiment of the present invention, the forward and the reverse primers are used for amplification of centromeric region of chromosome 1 of *Candida dubliniensis*.

The present invention also relates to a set of 14 primers having SEQ ID NOS. 29, 31, 33, 35, 37, 39 and 41 as forward primers and SEQ ID NOS. 30, 32, 34, 36, 38, 40 and 42 as corresponding reverse primers respectively.

In another embodiment of the present invention, the forward and the reverse primers are used for amplification of centromeric region of chromosome 2 of *Candida dubliniensis*.

The present invention also relates to a set of 10 primers having SEQ ID NOS. 43, 45, 47, 49 and 51 as forward primers and SEQ ID NOS. 44, 46, 48, 50 and 52 as corresponding reverse primers respectively.

In another embodiment of the present invention, the forward and the reverse primers are used for amplification of centromeric regions of chromosome 3 of *Candida dubliniensis*.

The present invention also relates to a set of 16 primers having SEQ ID NOS. 53, 55, 57, 59, 61, 63, 65 and 67 as forward primers and SEQ ID NOS. 54, 56, 58, 60, 62, 64, 66 and 68 as corresponding reverse primers respectively.

In another embodiment of the present invention, the forward and the reverse primers are used for amplification of centromeric regions of chromosome 4 of *Candida dubliniensis*.

The present invention also relates to a set of 10 primers having SEQ ID NOS. 69, 71, 73, 75 and 77 as forward primers and SEQ ID NOS. 70, 72, 74, 76 and 78 as corresponding reverse primers respectively.

In another embodiment of the present invention, the forward and the reverse primers are used for amplification of centromeric regions of chromosome 5 of *Candida dubliniensis*.

The present invention also relates to a set of 16 primers having SEQ ID NOS. 79, 81, 83, 85, 87, 89, 91 and 93 as forward primers and SEQ ID NOS. 80, 82, 84, 86, 88, 90, 92 and 94 as corresponding reverse primers respectively.

In another embodiment of the present invention, the forward and the reverse primers are used for amplification of centromeric regions of chromosome 6 of *Candida dubliniensis*.

The present invention also relates to a set of 18 primers having SEQ ID NOS. 95, 97, 99, 101, 103, 105, 107, 109 and 111 as forward primers and SEQ ID NOS. 96, 98, 100, 102, 104, 106, 108, 110 and 112 as corresponding reverse primers respectively.

In another embodiment of the present invention, the forward and the reverse primers are used for amplification of centromeric regions of chromosome 7 of *Candida dubliniensis*.

The present invention also relates to a set of 14 primers having SEQ ID NOS. 114, 116, 118, 120, 122, 123 and 126 as forward primers and SEQ ID NOS. 113, 115, 117, 119, 121, 124 and 125 as corresponding reverse primers respectively.

In another embodiment of the present invention, the forward and the reverse primers are used for amplification of centromeric regions of chromosome 8, also known as Chromosome R, of *Candida dubliniensis*.

The present invention also relates to a process of identification of centromeric sequences of *Candida dubliniensis*, said method comprising steps of:
 a) identifying putative Cse4p binding region; and
 b) amplifying the putative Cse4p binding region to identify centromeric sequences of the *Candida dubliniensis*.

In another embodiment of the present invention, the identification of putative Cse4p biding regions is carried out by sequence analysis and chromatin immunoprecipitation.

In yet another embodiment of the present invention the amplification of the putative Cse4p binding regions is carried out using any set of forward primer and its corresponding reverse primer selected from a group comprising SEQ ID NOS. 9, 11, 13, 15, 17, 19, 21, 23, 25 and 27 and SEQ ID NOS. 10, 12, 14, 16, 18, 20, 22, 24, 26, 28 respectively, for chromosome 1 of *Candida dubliniensis*; SEQ ID NOS. 29, 31, 33, 35, 37, 39 and 41 and SEQ ID NOS. 30, 32, 34, 36, 38, 40 and 42 respectively, for chromosome 2 of *Candida dubliniensis*; SEQ ID NOS. 43, 45, 47, 49 and 51 and SEQ ID NOS. 44, 46, 48, 50 and 52 respectively, for chromosome 3 of *Candida dubliniensis*; SEQ ID NOS. 53, 55, 57, 59, 61, 63, 65 and 67 and SEQ ID NOS. 54, 56, 58, 60, 62, 64, 66 and 68 respectively, for chromosome 4 of *Candida dubliniensis*; SEQ ID NOS. 69, 71, 73, 75 and 77 and SEQ ID NOS. 70, 72, 74, 76 and 78 respectively, for chromosome 5 of *Candida dubliniensis*; SEQ ID NOS. 79, 81, 83, 85, 87, 89, 91 and 93 and SEQ ID NOS. 80, 82, 84, 86, 88, 90, 92 and 94 respectively, for chromosome 6 of *Candida dubliniensis*; SEQ ID NOS. 95, 97, 99, 101, 103, 105, 107, 109 and 111 and SEQ ID NOS. 96, 98, 100, 102, 104, 106, 108, 110 and 112 respectively, for chromosome 7 of *Candida dubliniensis* and SEQ ID NOS. 114, 116, 118, 120, 122, 123 and 126 and SEQ ID NOS. 113, 115, 117, 119, 121, 124 and 125 respectively, for chromosome 8, also known as Chromosome R, of *Candida dubliniensis* or any combination of said primers thereof.

The present invention also relates to a method of distinguishing *Candida dubliniensis* from *Candida albicans* in a sample, said method comprising steps of
 a) isolating DNA from the organism in the sample; and
 b) amplifying the Cse4p binding regions with primers capable of amplifying said regions in the *Candida dubliniensis* to distinguish it from *Candida albicans*.

In another embodiment of the present invention, the identification of putative Cse4p biding regions is carried out by sequence analysis and chromatin immunoprecipitation.

In yet another embodiment of the present invention, the amplification of the putative Cse4p binding regions is carried out using any set of forward primer and its corresponding reverse primer selected from a group comprising SEQ ID NOS. 9, 11, 13, 15, 17, 19, 21, 23, 25 and 27 and SEQ ID NOS. 10, 12, 14, 16, 18, 20, 22, 24, 26, 28 respectively, for chromosome 1 of *Candida dubliniensis*; SEQ ID NOS. 29, 31, 33, 35, 37, 39 and 41 and SEQ ID NOS. 30, 32, 34, 36, 38, 40 and 42 respectively, for chromosome 2 of *Candida dubliniensis*; SEQ ID NOS. 43, 45, 47, 49 and 51 and SEQ ID NOS. 44, 46, 48, 50 and 52 respectively, for chromosome 3 of *Candida dubliniensis*; SEQ ID NOS. 53, 55, 57, 59, 61, 63, 65 and 67 and SEQ ID NOS. 54, 56, 58, 60, 62, 64, 66 and 68 respectively, for chromosome 4 of *Candida dubliniensis*; SEQ ID NOS. 69, 71, 73, 75 and 77 and SEQ ID NOS. 70, 72, 74, 76 and 78 respectively, for chromosome 5 of *Candida dubliniensis*; SEQ ID NOS. 79, 81, 83, 85, 87, 89, 91 and 93 and SEQ ID NOS. 80, 82, 84, 86, 88, 90, 92 and 94 respectively, for chromosome 6 of *Candida dubliniensis*; SEQ ID NOS. 95, 97, 99, 101, 103, 105, 107, 109 and 111 and SEQ ID NOS. 96, 98, 100, 102, 104, 106, 108, 110 and 112 respectively, for chromosome 7 of *Candida dubliniensis* and SEQ ID NOS. 114, 116, 118, 120, 122, 123 and 126 and SEQ ID NOS. 113, 115, 117, 119, 121, 124 and 125 respectively, for chromosome 8, also known as Chromosome R, of *Candida dubliniensis* or any combination of said primers thereof.

The present invention also relates to a kit for identification of *Candida dubliniensis* comprising set of primers having SEQ ID NOS. 9 to 126.

In another embodiment of the present invention, the amplification of the putative Cse4p binding regions is carried out using any set of forward primer and its corresponding reverse primer selected from a group comprising SEQ ID NOS. 9, 11, 13, 15, 17, 19, 21, 23, 25 and 27 and SEQ ID NOS. 10, 12, 14, 16, 18, 20, 22, 24, 26, 28 respectively, for chromosome 1 of *Candida dubliniensis*; SEQ ID NOS. 29, 31, 33, 35, 37, 39 and 41 and SEQ ID NOS. 30, 32, 34, 36, 38, 40 and 42 respectively, for chromosome 2 of *Candida dubliniensis*; SEQ ID NOS. 43, 45, 47, 49 and 51 and SEQ ID NOS. 44, 46, 48, 50 and 52 respectively, for chromosome 3 of *Candida dubliniensis*; SEQ ID NOS. 53, 55, 57, 59, 61, 63, 65 and 67 and SEQ ID NOS. 54, 56, 58, 60, 62, 64, 66 and 68 respectively, for chromosome 4 of *Candida dubliniensis*; SEQ ID NOS. 69, 71, 73, 75 and 77 and SEQ ID NOS. 70, 72, 74, 76 and 78 respectively, for chromosome 5 of *Candida dubliniensis*; SEQ ID NOS. 79, 81, 83, 85, 87, 89, 91 and 93 and SEQ ID NOS. 80, 82, 84, 86, 88, 90, 92 and 94 respectively, for chromosome 6 of *Candida dubliniensis*; SEQ ID NOS. 95, 97, 99, 101, 103, 105, 107, 109 and 111 and SEQ ID NOS. 96, 98, 100, 102, 104, 106, 108, 110 and 112 respectively, for chromosome 7 of *Candida dubliniensis* and SEQ ID NOS. 114, 116, 118, 120, 122, 123 and 126 and SEQ ID NOS. 113, 115, 117, 119, 121, 124 and 125 respectively, for chromosome 8, also known as Chromosome R, of *Candida dubliniensis* or any combination of said primers thereof.

The Cse4p-containing centromere regions of *Candida albicans* have unique and different DNA sequences on each of the eight chromosomes. In closely related yeast, *Candida dubliniensis*, the centromeric histone, CdCse4p, has been identified and it is shown to be localized at the kinetochore. The putative centromeric regions, orthologous to the *C. albicans* centromeres, in each of the eight *C. dubliniensis* chromosomes have been identified by bioinformatics analysis. Chromatin immunoprecipitation followed by polymerase chain reaction using a specific set of primers confirmed that these regions bind CdCse4p in vivo. As in *C. albicans*, the CdCse4p-associated core centromeric regions are 3-5 kb in length, and show no sequence similarity to one another. Comparative sequence analysis suggests that the Cse4p-rich centromere DNA sequences in these two species have diverged faster than other orthologous intergenic regions, and even faster than our best estimated "neutral" mutation rate. However, the location of the centromere and the relative position of Cse4p-rich centromeric chromatin in the orthologous regions with respect to adjacent open reading frames are conserved in both species, suggesting that centromere identity is not solely determined by DNA sequence. Unlike known point and regional centromeres of other organisms, centromeres in *C. albicans* and *C. dubliniensis* have no common centromere-specific sequence motifs or repeats except some of the chromosome-specific pericentric repeats that are found to be similar in these two species. The centromeres of these two *Candida* species are thus of an intermediate type between point and regional centromeres.

Several lines of evidence suggest that primary DNA sequence may not be the only determinant of CEN identity in regional centromeres. A recent study on several independent clinical isolates of *C. albicans* reveals that, despite having no centromere specific DNA sequence motifs or repeats common to all of its eight centromeres, centromere sequences remain conserved and their relative chromosomal positions are maintained (12). As a first step toward understanding the importance of cis-acting CEN DNA sequences in centromere function in *C. albicans*, centromeres of a closely related pathogenic yeast, *Candida dubliniensis*, which was identified as a less pathogenic independent species in 1995 were identified and characterized. It was thought that CEN DNA comparisons between related *Candida* species might uncover properties that were not evident from inter-chromosomal comparisons of *C. albicans* CEN sequences alone. Moreover, functional characterization of centromeres of these two related *Candida* species may be helpful in understanding the evolution of centromeres. Several studies indicate that both CEN DNA and its associated proteins in animals and plants are rapidly evolving, although the relative position of the centromere is maintained for a long time. The identification and characterization of Cse4p-rich centromere sequences of each of the eight chromosomes of *C. dubliniensis* was carried out. Comparative genomic analysis of CEN DNA sequences of *C. albicans* and *C. dubliniensis* reveals no detectable conservation among Cse4p-associated CEN sequences. Nonetheless, the lengths of Cse4p-enriched DNAs assembled as specialized centromeric chromatin and their relative locations in orthologous regions have been maintained for millions of years. A genome wide analysis also revealed that centromeres are probably the most rapidly evolving genomic loci in *C. albicans* and *C. dubliniensis*.

*Candida dubliniensis* has a total of 8 chromosomes. Chromosomes 1 to 7 are identified based on their respective sizes. The chromosome number 8 has an extensive number of R-DNA repeat sequences. Hence this chromosome is also referred to as Chromosome R.

The invention is further elaborated with the help of following examples. However, these examples should not be construed to limit the scope of the invention.

EXAMPLE 1

Synteny of Centromere-Adjacent Genes is Maintained in *C. albicans* and *C. dubliniensis*.

*C. albicans* and *C. dubliniensis* diverged about 20 million years ago from a common ancestor (12). Gene synteny (collinearity) is maintained almost throughout the genome in these two organisms. Therefore, potential orthologous CEN regions in *C. dubliniensis* were examined by identifying open reading frames (ORFs) of *C. dubliniensis* with homology to CEN-proximal ORFs of *C. albicans*. *C. dubliniensis* homologs of *C. albicans* ORFs that are adjacent to centromere regions were identified by BLAST analysis of the *C. dubliniensis* genome database available at the Wellcome Trust Sanger Institute website.

Result:

The homology of amino acid sequences coded by CEN-adjacent genes in *C. albicans* and *C. dubliniensis* ranges from 81% to 99%, as shown in Table 1 below.

TABLE 1

| | | | C. albicans | | C. dubliniensis | | | Amino |
|---|---|---|---|---|---|---|---|---|
| Chr No. | C. albicans ORF No. | C. dubliniensis ORF No. | Chromosomal coordinates | Amino acid length | Chromosomal coordinates | Amino acid length | Orientation | acid homology (%) |
| 1 | 4438 | Cd36__06830 | 1580117-1581640 | 507 | 1611890-1613440 | 516 | Direct | 88 |
| | 4440 | Cd36__06810 | 1559352-1561871 | 839 | 1591631-1594162 | 843 | Direct | 91 |
| 2 | 1601 | Cd36__23540 | 1923194-1924363 | 389 | 1938439-1939608 | 389 | Direct | 99 |
| | 1604 | Cd36__23560 | 1934775-1931570 | 916 | 1947203-1949623 | 806 | Reverse | 84 |
| 3 | 2812 | Cd36__83930 | 828667-827105 | 503 | 871879-873366 | 495 | Reverse | 84 |
| | 6923 | Cd36__83920 | 820347-821378 | 343 | 865253-866083 | 276 | Direct | 90 |
| 4 | 3818 | Cd36__44310 | 1010148-1009312 | 278 | 1036396-1037226 | 276 | Reverse | 88 |
| | 3821 | Cd36__44290 | 1000558-999371 | 395 | 1025948-1027126 | 392 | Reverse | 81 |
| 5 | 3160 | Cd36__51930 | 467208-466702 | 168 | 493689-494072 | 127 | Reverse | 95 |
| | 4216 | Cd36__51940 | 473741-474247 | 168 | 500592-500975 | 127 | Direct | 94 |
| 6 | 1096 | Cd36__64780 | 965934-968573 | 879 | 934029-936683 | 884 | Direct | 84 |
| | 2124 | Cd36__65100 | 982460-981390 | 353 | 1016599-1017672 | 357 | Reverse | 87 |
| 7 | 6522 | Cd36__71800 | 431903-430173 | 586 | 439178-440899 | 573 | Reverse | 94 |
| | 6524 | Cd36__71780 | 423631-422459 | 390 | 424821-425993 | 390 | Reverse | 99 |
| R | 597 | Cd36__33630 | 1759087-1757405 | 560 | 1722610-1724292 | 560 | Reverse | 97 |
| | 600 | Cd36__33620 | 1748818-1745649 | 1056 | 1710255-1713449 | 1064 | Reverse | 90 |

The synteny of these genes is maintained in all chromosomes except chromosome 6. FIG. 1 shows orthologous Cse4p-rich centromere regions in *C. albicans* and *C. dubliniensis*. Based on BLAST analysis, the putative homologs of *C. albicans* CEN-adjacent ORFs in *C. dubliniensis* have been identified. Chromosome numbers are shown on the left (R through 7). The top line for each chromosome denotes *C.* albicans centromere regions and the bottom line corresponds to the orthologous regions in *C. dubliniensis*. The dotted and crossed boxes correspond to Cse4p-binding regions in *C. albicans* and *C. dubliniensis* respectively. Only one homolog is shown for each chromosome of *C. albicans* and *C. dubliniensis*. ORFs and the direction of transcription of corresponding ORFs are shown by open arrows. Only those ORFs which have homologs in both *C. albicans* and *C. dubliniensis* are shown. The number on the top of each arrow corresponds to the *C. albicans* assembly 19 ORF numbers (for example, orf19.600 has been shown as 600). The length of CEN-containing intergenic regions of *C. albicans* and orthologous regions in *C. dubliniensis* are shown. This analysis was done based on Assembly 20 of *Candida albicans* Genome Database and the present version (16 May 2007) of the *Candida dubliniensis* Genome database.

*C. albicans* CEN6 is flanked by Orf19.1097 and Orf19.2124. Since there is no Orf19.1097 homolog in *C. dubliniensis*, the *C. dubliniensis* homolog of Orf19.1096, the gene adjacent to Orf19.1097 in *C. albicans* were identified. The distance between Orf19.1096 and Orf19.2124 is 12.8 kb in *C. albicans* as opposed to 80 kb in *C. dubliniensis*. A systematic analysis of this 80 kb region of *C. dubliniensis* reveals that two paracentric inversions followed by an insertion between Orf19.1096 homolog and its downstream region occurred in *C. dubliniensis* at the left arm of the orthologous pericentric region as compared to *C. albicans*. FIG. 4 shows comparative analysis of CEN6 region of *C. albicans* and its orthologous region in *C. dubliniensis* showing genome rearrangement. Chromosomal maps of the chromosome 6 of *C. albicans* and *C. dubliniensis* where the red dots represent the CEN regions. Black arrows along with the ORF numbers show the gene arrangement and the direction of transcription. Two paracentric inversions in *C. dubliniensis* are marked in shaded red and grey boxes. The direction of the shaded boxes (gradation of colors) represents the inversions that have occurred in *C. dubliniensis* when compared to *C. albicans*. The green arrows show the breakpoints where the inversions have occurred. The blue region in *C. dubliniensis* shows the region of insertions of ORFs from other chromosomes. The yellow regions are unaltered. The orange arrow shows the Orf19.1097 in *C. albicans* and the orange star in the *C. dubliniensis* map shows that there is a premature termination codon in the Orf19.1097 homolog of *C. albicans* in *C. dubliniensis*. Brown bar indicates Cse4p-binding region.

EXAMPLE 2

The Centromeric Histone Protein of *C. dubliniensis* (CdCse4p) is Localized at the Kinetochore.

CenH3 proteins in the Cse4p/CENP-A family have been shown to be uniquely associated with centromeres in all organisms studied to date (1). Using CaCse4p as the query in a BLAST analysis against the *C. dubliniensis* genome, the centromeric histone of *C. dubliniensis*, CdCse4p were identified.

Identification of CdCse4p and CdMif2p:

The *C. dubliniensis* Cse4p was identified by a BLAST search with *C. albicans* Cse4p (CaCse4p) as the query sequence against the *C. dubliniensis* genome sequence database. This sequence analysis revealed three protein sequences with high homology to CaCse4p; two are the *C. dubliniensis* putative histone H3 proteins (Chr RCd36_32350; Chr1-Cd36_04010) and the other CdCse4p (Chr 3-Cd36_80790). The CdCSE4 gene encodes a putative 212 aa-long protein with 100% identity in the C terminal histone fold domain of CaCse4p. A pair wise comparison of the CaCse4p and CdCse4p sequences revealed that they share 97% identity and 1.4% similarity over a 212 aa overlap as shown in FIG. 5.

Using CaMif2p as the query sequence in the BLAST search against the *C. dubliniensis* genome database, a single hit was retrieved, which was identified as the CENP-C homolog (Cd36_63360) in *C. dubliniensis* showing 77% identity and 5% similarity in 516 aa overlap with CaMif2p. FIG. 7 shows the CENP-C homolog in *C. dubliniensis* (CdMif2p) is co-localized with CdCse4p. (A) Sequence alignment of CaMif2p and CdMif2p showing the conserved CENP-C block (red box) (B) Localization of CdMif2p at various stages of cell cycle in *C. dubliniensis*. (C) ChIP enrichment profiles of CdMif2p on chromosomes 1 and 3 in the strain CDM1 by determining the intensities of (+Ab) minus (−Ab) signals divided by the total DNA signals and are normalized to a value of 1 for the same obtained using primers for a non-centromeric locus (CdLEU2). The CdMIF2 gene codes for a putative 520 aa-long protein with a conserved CENP-C box required for centromere targeting (11) that is identical in *C. albicans* and *C. dubliniensis* as shown in FIG. 5. This histone is found to be highly similar (97% identity over 211 aa) to CaCse4p. CdCse4p codes for a 212-aa-long predicted protein with a C-terminal (aa residues 110-212) histone-fold domain (HFD). The HFD of Cse4p in *C. albicans* and *C. dubliniensis* is identical as shown in FIG. 5. FIG. 5 shows the centromeric histone in *C. dubliniensis*, CdCse4p, belongs to the Cse4p/CENP-A family. A) Phylogenetic tree of the Cse4 protein sequences in yeasts in the radiation format using neighbor-joining method of Molecular Evolutionary Genetics Analysis version 3.1 (MEGA) software showing Cse4 proteins in *C. albicans* and *C. dubliniensis* are highly related. Ca—*Candida albicans*, Cd—*Candida dubliniensis*, Db—*Debaryomyces hansenii*, Pa—*Pichia angusta*, Kl—*Kluyveromyces lactis*, Cn—*Cryptococcus neoformans*, Sp—*Schizosaccharomyces pombe*, Af—*Aspergillus fumigatus*, Nc—*Neurospora crassa*, Yl—*Yarrowia lipolytica*, Ag—*Ashbya gossypii*, Sc—*Saccharomyces cerevisiae*, Cg—*Candida glabrata*. B) Pairwise comparison of Cse4p in *C. albicans* and *C. dubliniensis* showing homologies in N-terminal region and C-terminal histone fold domain.

EXAMPLE 3

The Centromeric Histone Protein of *C. dubliniensis* (CdCse4p) can Functionally Compliment Histone Protein of *C. albicans* (CaCse4p).

In order to examine whether CdCse4p can functionally complement CaCse4p, CdCSE4 from its native promoter (pAB1CdCSE4) cloned in an ARS2/HIS1 plasmid (pAB1) in a *C. albicans* strain (CAKS3b) carrying the only full length copy of CaCSE4 under control of the PCK1 promoter was expressed.

Complementation Assay:

To examine whether CdCse4p can complement CaCse4p function, a *C. albicans* strain was constructed, where the first allele of CaCSE4 was disrupted using URA-blaster cassette followed by recycling of URA3 marker, and the second allele was placed under control of the PCK1 promoter. To disrupt the first CaCSE4 allele, a 4.9 kb URA-blaster-based CaCSE4 deletion cassette was released from pDC3 (Sanyal & Carbon, 2002) as SalI-SacI fragment and transformed BWP17 selecting for uridine prototrophy. The correct integrant (CAKS1b) was selected by Southern analysis. Thereafter, Ura-strain, obtained by intrachromosomal recombination between hisG repeats resulting in the loss of URA3 marker, was selected on medium containing 5-fluoroorotic acid (5-FOA). The correct revertant (CAKS2b) was identified by PCR analysis. To place the wild type CSE4 allele under regulation of the PCK1 promoter in CAKS2b, pPCK1-CSE4 was linearized (Sanyal & Carbon, 2002) by EcoRV and used it to transform strain CAKS2b, selecting transformants for uridine prototrophy. The desired integrant (CAKS3b) carrying the only full-length copy of CSE4 under control of the PCK1 promoter was identified by PCR analysis. CAKS3b can grow on succinate medium (where the PCK1 promoter is induced) but is unable to grow on glucose medium (where PCK1 promoter is repressed) as shown in FIG. 2A. To test whether CdCse4p can complement CaCse4p function, both CdCSE4 and CaCSE4 genes were cloned in an ARS2/HIS1 plasmid, pAB1 (Baum et al., 2006). A 2.14-kb fragment carrying CdCSE4 (CdChr3 coordinates 170543-172683) and a 2.13-kb fragment carrying CaCSE4 (CaChr3 coordinates 172252-174384) genes along with their respective promoters and terminators were amplified using FCdCSE4/RCdCSE4 and FCaCSE4/RCaCSE4 primer pairs, respectively, as listed in Table 2 below.

TABLE 2

| Primer | Sequence | Chromosomal locations | SEQ ID NO |
|---|---|---|---|
| For CdCEN1 | | | |
| CdCEN1-1(F) | AAGCCCTTTGGATGTTGACTACGC | 1593208-1593231 | 9 |
| CdCEN1-2(R) | CCATCGACAGGGCCCATGTG | 1593417-1593398 | 10 |
| CdCEN1-3(F) | TATGATTATACCCCAATCCA | 1595086-1595105 | 11 |
| CdCEN1-4(R) | AGGATCAGTTACCAATGTTG | 1595287-1595268 | 12 |
| CdCEN1-3'(F) | CAACAATCAACAATTTCTGCTCCTCATG | 1596131-1596158 | 13 |
| CdCEN1-4'(R) | AAGTGGGTATCACCTTATTCGCAAATGA | 1596368-1596341 | 14 |
| CdCEN1-5(F) | CCTTTTTAAACGTGACACGCTCAAA | 1597063-1597087 | 15 |
| CdCEN1-6(R) | GGAAAAGTTGCGTGAGGAAATGGA | 1597302-1597279 | 16 |
| CdCEN1-5'(F) | CGGGTGCATCTAAGAAGGGTTTTA | 1598062-1598085 | 17 |
| CdCEN1-6'(R) | CAATATAACCTTGCACCCGTCAAATACG | 1598347-1598320 | 18 |
| CdCEN1-7(F) | GTTGCAGTGCATTGTACGAGGTAAGCTC | 1599081-1599108 | 19 |
| CdCEN1-8"(R) | TGCAACTGATCCGAGACAACTTCAAAC | 1599271-1599245 | 20 |
| CdCEN1-7'(F) | GATCGCAAGCGAAGCACGAAATGAC | 1600481-1600505 | 21 |
| CdCEN1-8'(R) | CAATGTCTGTTCGACCACCATTCCC | 1600721-1600697 | 22 |
| CdCEN1-9(F) | AGAGCGAGCACCTGGTATTCCCAAG | 1601290-1601314 | 23 |
| CdCEN1-10(R) | CACCCAAAGCCCAGCTTAAATTCC | 1601509-1601486 | 24 |
| CdCEN1-9'(F) | TTTCAATTTAGCTGACTCCTTACCCTGG | 1602167-1602194 | 25 |
| CdCEN1-10'(R) | TTTTCGGTGATTTTGCCAAGAAGTTC | 1602410-1602385 | 26 |
| CdCEN1-11(F) | CAGCATTCATCCGGGTAAAGTGTTG | 1603320-1603344 | 27 |
| CdCEN1-12(R) | CAACGGATCCAAGGTCACCACATAG | 1603543-1603519 | 28 |
| Control (Non centromeric locus in chromosome 7) | | | |
| CdLeu2-1(F) | AACTATCACAGTCTTGCCTGGTGA | 119386-119409 | 127 |
| CdLeu2-2(R) | ACAGCACCAGTGCCCCATTT | 119618-119637 | 128 |
| For CdCEN2 | | | |
| CdCEN2-1(F) | CGCGGTCCAAGAAGATAATC | 1940515-1940534 | 29 |
| CdCEN2-2(R) | CATCATGGGATGTAATTGCT | 1940649-1940668 | 30 |
| CdCEN2-3(F) | AGTGTAAGTCTTCGGGATAC | 1942509-1942528 | 31 |
| CdCEN2-4(R) | GTGAGCGAATAGAATAATTG | 1942685-1942704 | 32 |
| CdCEN2-5(F) | AGCTACATCTATTTTCAATGCACTC | 1944606-1944630 | 33 |
| CdCEN2-6(R) | AATTGCTCTGAAACAGCCAG | 1944877-1944896 | 34 |
| CdCEN2-7(F) | TATACCCCCGAATTAACAAGTGCGC | 1943700-1943724 | 35 |
| CdCEN2-8(R) | CAGTGCAGGTGCTTTCGTTTACCAG | 1943847-1943871 | 36 |

TABLE 2-continued

| Primer | Sequence | Chromosomal locations | SEQ ID NO |
|---|---|---|---|
| CdCEN2-9(F) | CATCAGTTCAATTGATGGGGTTGTTCTG | 1945542-1945569 | 37 |
| CdCEN2-10(R) | AAACTGGCATAGCTTTTTGCATTATTGCC | 1945736-1945764 | 38 |
| CdCEN2-11(F) | ATTTCGAGAGGACTTGGTTCGTGC | 1946646-1946669 | 39 |
| CdCEN2-12(R) | CCGTACCCAAATAAAACTCCCAGC | 1946844-1946867 | 40 |
| CdCEN2-15(F) | TACAAAGCGGGTGATAAGGA | 1947305-1947054 | 41 |
| CdCEN2-16(R) | GGCGCAAAAGGAAATAGC | 1947234-1947217 | 42 |
| For CdCEN3 | | | |
| CdCEN3-1(F) | ACACTGTCTTGTCTTGTGTCTGAAGTCG | 865133-865160 | 43 |
| CdCEN3-2(R) | TTCTCTGTGTGTGGGCCCTCAGTAC | 865293-865317 | 44 |
| CdCEN3-3(F) | TCATCCATCATATCACAAATCCTACTG | 867274-867300 | 45 |
| CdCEN3-4(R) | GTTATTTTGAAAGTTGGGGAGAGGG | 867456-867480 | 46 |
| CdCEN3-5(F) | CCTACGACATGAACACATCAAACTACTC | 869090-869117 | 47 |
| CdCEN3-6(R) | TGCTTTTGTTGAAAACTTGCGAAAC | 869243-869267 | 48 |
| CdCEN3-7(F) | AGGCTAGTCGGTGGTTAACGGTTGTGTG | 870638-870665 | 49 |
| CdCEN3-8(R) | GACTCGGAATAAACACCATCGCCGATGC | 870856-870883 | 50 |
| CdCEN3-9(F) | GGTCCAATTAGAATCGGGTCGTTCCATG | 872528-872555 | 51 |
| CdCEN3-10(R) | CGTCATCCCTTCTATCTCTAACGTG | 872683-872707 | 52 |
| For CdCEN4 | | | |
| CdCEN4-1(F) | ATCATATCATGCAGCCCAACTCCG | 1028245-1028268 | 53 |
| CdCEN4-2(R) | CGGACGTAGTGAAACGATTGTTGG | 1028410-1028433 | 54 |
| CdCEN4-3(F) | ACAATTCCCAGTAAACCATTATAAAAG | 1029835-1029861 | 55 |
| CdCEN4-4(R) | CATTCATAATCTGATTTGTAGGCTC | 1029965-1029989 | 56 |
| CdCEN4-3'(F) | TGCTAAACGACCCCCTCAAAA | 1030554-1030574 | 57 |
| CdCEN4-4'(R) | GTACGACGATCATCAGCAACCAA | 1030776-1030798 | 58 |
| CdCEN4-5(F) | AATTAATTCGGATAGTTGGGGGAGACCG | 1032446-1032473 | 59 |
| CdCEN4-6(R) | ATTGAGCTGCTCACTTCACTGCCAC | 1032619-1032643 | 60 |
| CdCEN4-5'(F) | GCAGCGTTCTTGTGACCGTGAG | 1033199-1033220 | 61 |
| CdCEN4-6'(R) | TTGAATTGGACAGGGGCTTAGG | 1033477-1033498 | 62 |
| CdCEN4-7(F) | TGTGGTGGAGGGTCATCCATTTGTTGGTTG | 1034406-1034435 | 63 |
| CdCEN4-8(R) | GGCGACCCTCATGCACCCTACCAAATAAA | 1034609-1034637 | 64 |
| CdCEN4-7'(F) | AAGTACGGATGGTTGTTA | 1035010-1035028 | 65 |
| CdCEN4-8'(R) | TAGTCATTCTGCCATCTCTTAT | 1035231-1035252 | 66 |
| CdCEN4-9(F) | CCATGAACAAAAGGTTAGGTGGTGCTCC | 1036158-1036185 | 67 |
| CdCEN4-10(R) | GGGGAGTTGAATGGTGTGGTGTTAC | 1036367-1036391 | 68 |
| For CdCEN5 | | | |
| CdCEN5-7(F) | TCCAGCGTCAGACATTTTTCCAGT | 494058-494081 | 69 |
| CdCEN5-8(R) | TGCCCCGCGGTTGACAGT | 494213-494230 | 70 |
| CdCEN5-1(F) | TGGCCTCTCCCTTACAAAATTTGCCC | 495324-495349 | 71 |
| CdCEN5-2(R) | GGGAGATGAGGGGTGATTGAGGTAATAG | 495504-495531 | 72 |

TABLE 2-continued

| Primer | Sequence | Chromosomal locations | SEQ ID NO |
|---|---|---|---|
| CdCEN5-3(F) | GCTCCAGTACCAACGAAAACGACTTC | 496907-496932 | 73 |
| CdCEN5-4(R) | GCATTTGAAAACTGCCAATGTAGTC | 497035-497059 | 74 |
| CdCEN5-5(F) | GCTGGGATAGTTTAGAGGCAGACTGTG | 498944-498971 | 75 |
| CdCEN5-6(R) | CCTCAATCACCCCTCATCTCCCTAC | 499130-499155 | 76 |
| CdCEN5-9(F) | AAGGGCAAGGAACAAGTCACAAGT | 500673-500696 | 77 |
| CdCEN5-10(R) | TATCAGCGCCGGTTTTAGCAC | 500941-500961 | 78 |
| For CdCEN6 | | | |
| CdCEN6-15(F) | GTGCCAACTTTCTCCTGAT | 1002806-1002824 | 79 |
| CdCEN6-16(R) | AGCGATTATTAAGTCTATGTGG | 1002985-1002964 | 80 |
| CdCEN6-13(F) | GAAGCAGCGACCCAACAGATAA | 1003044-1003065 | 81 |
| CdCEN6-14(R) | TTGAGCGAAATTGGGTAGAGTC | 1003262-1003283 | 82 |
| CdCEN6-5(F) | TGTCCATTCCCCAAACTTCATACGGACCAC | 1004039-1004068 | 83 |
| CdCEN6-6(R) | GAATGCTGGAAGGACTTGAGAAATG | 1004175-1004199 | 84 |
| CdCEN6-5'(F) | GAAACCAATAACAAGGAAAGAGTA | 1005046-1005069 | 85 |
| CdCEN6-6'(R) | CAATGGGAAAAGAAATCAGTAG | 1005313-1005335 | 86 |
| CdCEN6-7(F) | GACGAGAGCATGTACTCAACTACGTGTC | 1006472-1006499 | 87 |
| CdCEN6-8(R) | GAATCTTGATTGAAATGCGAGGAAC | 1006668-1006692 | 88 |
| CdCEN6-9(F) | CATCCAATAACATTGATTTACTACTTTTAG | 1008985-1009014 | 89 |
| CdCEN6-10(R) | TTTTTTTTTCTCAAAGATTTAGCAG | 1009115-1009139 | 90 |
| CdCEN6-9'(F) | TGTACGATCAACCCAGAGTGC | 1009504-1009524 | 91 |
| CdCEN6-10'(R) | ACATGCCATTACCAACAACAGTC | 1009749-1009771 | 92 |
| CdCEN6-3(F) | TAGCTGTATTAAAAAATTCTGGCCGCATA | 1015917-1015945 | 93 |
| CdCEN6-4(R) | TCTGACAAAAAACCTCGTATGACCC | 1016066-1016042 | 94 |
| For CdCEN7 | | | |
| CdCEN7-1(F) | CTAGAGCTATGTTGTGACAGTCCACC | 427615-427640 | 95 |
| CdCEN7-2(R) | CTTCTGGAATTGAGCCAATCCCTAG | 427777-427801 | 96 |
| CdCEN7-3(F) | CTAGCTATTCAAGCATCCGTAGGCAGTC | 429103-429130 | 97 |
| CdCEN7-4(R) | CCCATACCCGGGTGGTGTAGTATAA | 429228-429252 | 98 |
| CdCEN7-5(F) | GTAGGCGCTACATATGAACTTCGTGC | 436328-436354 | 99 |
| CdCEN7-6(R) | AGATAATGTCTGAATGTCATTCGGG | 436479-436504 | 100 |
| CdCEN7-9'(F) | TCCAATGGGTGCTAAGATGAA | 434047-434068 | 101 |
| CdCEN7-10'(R) | TCCCGCCTGATTTTTGAA | 434292-434310 | 102 |
| CDCEN7-7(F) | TTATTTGATAGCCTAATTTCACCTGATG | 438005-438031 | 103 |
| CdCEN7-8(R) | ATTAACTGACTTTGAACCAGCAATG | 438205-438230 | 104 |
| CdCEN7-9(F) | AACGGTCACCTGATGAATAGAGTGGC | 432732-432758 | 105 |
| CdCEN7-10(R) | GACTGAAGCGTCCATACTTGGGATC | 432956-432981 | 106 |
| CdCEN7-11(F) | CCCAGAAGTATCCACTAGGGAACTTG | 435240-435268 | 107 |
| CdCEN7-12(R) | TTGTTCTGGTCAATGGTACAGCAAC | 435365-435390 | 108 |
| CdCEN7-13(F) | CACGCAACTAGAATGGCATGAATATATG | 439500-439527 | 109 |

TABLE 2-continued

| Primer | Sequence | Chromosomal locations | SEQ ID NO |
|---|---|---|---|
| CdCEN7-14(R) | AGATCCGGTGTCTGTCTTATTGCTC | 439630-439654 | 110 |
| CdCEN7-15(F) | CCTGCGTTGTAATCATTTGTTGTC | 440443-440466 | 111 |
| CdCEN7-16(R) | TTACTCCGCCTTTGATCCCTATTT | 440640-440617 | 112 |
| For CdCENR | | | |
| CdCENR-1(R) | ATTAAGGAGCTTCGTGAGGCTGTCG | 1723671-1723647 | 113 |
| CdCENR-2(F) | CATTTCCTTCAAAGGCACCGGGATG | 1723429-1723453 | 114 |
| CdCENR-3(R) | ACGTTGCTTACTGGTGGCTATGCGG | 1721710-1721686 | 115 |
| CdCENR-4(F) | AAGCTTTTATTGCGGTGAACTGGGG | 1721461-1721485 | 116 |
| CdCENR-5(R) | ACATATAATAGCCTACCACACGCCTTGC | 1719373-1719346 | 117 |
| CdCENR-6(F) | TGACATTGTGGAAAGTTAATCGCGG | 1719202-1719226 | 118 |
| CdCENR-7(R) | TGAAATTGGAGACTAAGTGTTGCATTCG | 1717531-1717504 | 119 |
| CdCENR-8(F) | ACAGTTTCCACACAACTCAGCAAGACA | 1717330-1717356 | 120 |
| CdCENR-9(R) | TTTGCCGGGATAAGCTTTTATTGCG | 1715642-1715618 | 124 |
| CdCENR-10(F) | TTTCAGGACACCAGAAGATGGCCAC | 1715409-1715433 | 122 |
| CdCENR-9'(F) | CCCCCGCCGTGAAAAACA | 1713200-1713217 | 123 |
| CdCENR-10'(R) | CTACAAACGCCACACCCGAAACT | 1713426-1713404 | 124 |
| CdCENR-11(R) | ACCTCAACATCGACACAGTCGCACC | 1712709-1712185 | 125 |
| CdCENR-12(F) | AGCAGAAACCTCGATGTTTGAGCCG | 1712487-1712511 | 126 |

TABLE 2B

| Primer | Sequence | SEQ ID NO |
|---|---|---|
| FCaCse4 | *CCCGAGCTCCAATTAACAAATATTAATTACAAATG* | 129 |
| RCaCse4 | TGCTCTAGACCAAAATCCCTCTTTCTGTATTTG | 130 |
| FCdCse4 | CCCGAGCTCCAAGTGTATTTTTCATCTTTGGTAG | 131 |
| RCdCse4 | CCCAAGCTTCTATTTTGCCACCAAAACCCATCTT | 132 |

These amplified CdCSE4 and CaCSE4 sequences were digested with SacI/HindIII and SacI/XbaI, respectively, and cloned into corresponding sites of pAB1 to get pAB1CdCSE4 and pAB1CdCSE4. Subsequently CAKS3b was transformed with pAB1, pAB1CaCSE4 or pAB1CdCSE4 and transformants were selected for histidine prototrophy on succinate medium followed by streaking on succinate as well as glucose containing media.

Result:

The ability of the strain CAKS3b carrying pAB1CdCSE4 to grow as good as the same strain carrying a control plasmid pAB1CaCSE4 on glucose medium (where endogenous CaCSE4 expression is suppressed) suggests that CdCse4p can complement CaCse4p function and hence codes for the centromeric histone in *C. dubliniensis* (FIG. 2B).

FIG. 2 shows localization of CdCse4p at the kinetochore of *C. dubliniensis*. (A) The *C. albicans* strain CAKS3b was streaked on media containing succinate and glucose and incubated at 30° C. for 3 days. (B) CAKS3b is transformed with pAB1, pAB1CaCSE4 or pAB1CdCSE4. These transformants were streaked on plates containing complete media lacking histidine with succinate or glucose as the carbon source. (C) *C. dubliniensis* strain Cd36 was grown in YPD and fixed. Fixed cells were stained with DAPI (a-d), anti-Ca/CdCse4p (e-h) and anti-tubulin (i-l) antibodies. The intense red dot-like CdCse4p signals were observed in unbudded (e) and at different stages of budded cells (f-h). Corresponding spindle structures are shown by co-immunostaining with anti-tubulin antibodies (i-l). Arrows indicate the position of spindle pole bodies in large-budded cells at anaphase. (Bar=10 μm).

EXAMPLE 4

Subcellular Localization of CdCse4p in *C. dubliniensis*.

The subcellular localization of CdCse4p in *C. dubliniensis* strain Cd36 was further examined by indirect immunofluorescence.

Indirect Immunofluorescence:

Intracellular CdCse4p or CdMif2p were visualized by indirect immunofluorescence microscopy as described previously. Asynchronously grown cells of Cd36 or CDM1 were fixed with 37% formaldehyde at room temperature for an hour. Antibodies were diluted as follows: 1:30 for anti-a-tubulin (YOL1/34) (Abcam); 1:500 for affinity purified rabbit anti-Ca/CdCse4p and rabbit anti-Protein A (Sigma); 1:500 for Alexa fluor 488 goat anti-rat IgG (Invitrogen) and 1:500 for Alexa fluor 568 goat anti-rabbit IgG (Invitrogen). The positions of nuclei of the cells were determined by staining with 4',6-diamidino-2-phenylindole (DAPI) as described previously. Cells were examined at 100× magnification on a confocal laser scanning microscope (LSM 510 META, Carl Zeiss). Using LSM 5 Image Examiner, digital images were captured. Images were processed by Adobe PhotoShop software.

Result:
 Indirect immunofluorescence microscopy using affinity purified polyclonal anti-Ca/CdCse4p antibodies (against aa1-18 of CaCse4p/CdCse4p) revealed bright dot-like signals in all cells. The dots always co-localized with nuclei stained with DAPI (FIG. 2C). Each bright dot-like signal represents a cluster of 16 centromeres. Unbudded G1 cells exhibited one dot per cell, while large-budded cells at later stages of the cell cycle exhibited two dots that co-segregated with the DAPI-stained nuclei in daughter cells (FIG. 2C). The localization patterns of CdCse4p appear to be identical to those of CaCse4p in *C. albicans* at corresponding stages of the cell cycle. Co-immunostaining of fixed Cd36 cells with anti-tubulin and anti-CdCse4p antibodies showed that CdCse4p signals are localized close to the spindle pole bodies, analogous to typical localization patterns of kinetochore proteins in *S. cerevisiae* and *C. albicans* (FIG. 2C). Together, these results strongly suggest that CdCse4p is the authentic centromeric histone of *C. dubliniensis*.

EXAMPLE 5

Centromeric Chromatin on Various *C. dubliniensis* Chromosomes is Restricted to a 3-5 kb Region.
 Standard chromatin immunoprecipitation (ChIP) assays with anti-Ca/CdCse4p antibodies to assay for enrichment of CdCse4p on putative CEN regions (orthologous to *C. albicans* CENs) in *C. dubliniensis* strain Cd36.
Chromatin Immunoprecipitation (ChIP) Assay and Sequence Analysis:
 Chromatin immunoprecipitation (ChIP) by anti-CdCse4 antibodies followed by PCR analysis was done as described previously (9, 11). This suggests that the predicted centromeric regions of all chromosomes of *C. dubliniensis* are enriched in centromeric specific histone (CdCse4p) binding. Asynchronously grown culture of Cd36 was crosslinked with formaldehyde and sonicated to get chromatin fragments of an average size of 300-500 bp. The fragments were Immunoprecipitated with anti-Ca/CdCse4p antibodies and checked by PCR. PCR reaction was set up using 10 pmol of both forward and reverse primers (MWG Biotech & Ocimum Biosolutions), 5 µl of 10× Taq buffer (Sigma), 5 µl of 2.5 mM dNTPs mix, 2 µl of DNA template and 0.3 µl of Taq polymerase (Sigma) in 50 µl reaction volume. PCR amplification was carried out using PCR machine (BIORAD) with the following conditions: 1 min at 94° C. (denaturation), 30 s at 45° C.-55° C. (annealing temperature is variable with the primers used) and 1 min at 72° C. (extension). A final extension of 4 min was given at 72° C. PCR with total DNA (1:10 dilution) and ±antibody ChIP DNA fractions were performed using ½sth of the template. The boundaries of the CEN regions on each chromosome of *C. dubliniensis* were mapped using semi-quantitative ChIP-PCR in strain Cd36. Sequence-specific PCR primers were designed at approximately 1 kb sequence intervals that spans the putative CEN region of each chromosome of *C. dubliniensis* (Table 2 above). CdLEU2 PCR primers were used as an internal control in all PCR reactions. PCR amplification was performed and the PCR products were resolved on 1.5% agarose gels and band intensities were quantified using Quantity One 1-D Analysis Software (BioRad). Enrichment values equal (+Ab) minus (−Ab) signals divided by the total DNA signal and were normalized to a value of 1 for LEU2. The PCR primers used in this study are listed in Table 2 above. Similarly, a ChIP assay to determine occupancy of TAP tagged CdMif2p was performed using the strain CDM1 with anti-Protein A antibodies. All other conditions were identical as it was described above for CdCse4p ChIP antibodies.
Result:
 The immunoprecipitated DNA sample was analyzed by PCR using a specific set of primers designed from the putative CEN sequences (Table 2 above). These regions are, indeed, found to be associated with CdCse4p as shown in FIG. 3. This ChIP-PCR analysis precisely localized the boundaries of CdCse4p-binding to a 3-5 kb region on each chromosome (FIG. 3).
 FIG. 3 shows two evolutionarily conserved key kinetochore proteins, CdCse4p (CENP-A homolog) and CdMif2p (CENP-C homolog) bind to the same regions of different *C. dubliniensis* chromosomes. Standard ChIP assays were performed on strains Cd36 and CDM1 (CdMif2-TAP-tagged strain) using anti-Ca/CdCse4p or anti-Protein A antibodies and analyzed with specific primers corresponding to putative centromere regions of *C. dubliniensis* to PCR amplify DNA fragments (150 to 300 bp) located at specific intervals as indicated (Table 2 above). Graphs showing relative enrichment of CdCse4p (blue lines) and CdMif2p (red lines) that mark the boundaries of centromeric chromatin in various *C. dubliniensis* chromosomes. PCR was performed on total, immunoprecipitated (+Ab), and beads only control (−Ab) ChIP DNA fractions (see Supporting FIGS. 6 and 7). The coordinates of primer locations are based on the present version (16 May 2007) of the *Candida dubliniensis* genome database. The coordinates are listed in Table 3 below. Enrichment values are calculated by determining the intensities of (+Ab) minus (−Ab) signals divided by the total DNA signals and are normalized to a value of 1 for the same obtained using primers for a noncentromeric locus (CdLEU2) and plotted. The chromosomal coordinates are marked along X-axis while the enrichment values are marked along Y-axis. Black arrows show the location and arrowheads indicate the direction of transcription.

TABLE 3

| Chr No. | Regions | *C. albicans* coordinates | *C. dubliniensis* coordinates |
|---|---|---|---|
| R | Region from left ORF | 1748819-1750873 | 1713450-1716138 |
|   | Cse4 binding region | 1750874-1755348 | 1716139-1720954 |
|   | Region from right ORF | 1755349-1757404 | 1720955-1722609 |
| 1 | Region from left ORF | 1561872-1564187 | 1594163-1596130 |
|   | Cse4 binding region | 1564188-1567117 | 1596131-1600697 |
|   | Region from right ORF | 1567118-1580116 | 1600698-1611889 |
| 2 | Region from left ORF | 1924364-1928514 | 1939609-1943699 |
|   | Cse4 binding region | 1928515-1931474 | 1943700-1946867 |
|   | Region from right ORF | 1931475-1931569 | 1946868-1947202 |
| 3 | Region from left ORF | 821379-823848 | 866084-867273 |
|   | Cse4 binding region | 823849-826997 | 867274-870883 |
|   | Region from right ORF | 826998-827104 | 870884-871878 |
| 4 | Region from left ORF | 1000559-1002628 | 1027127-1029834 |
|   | Cse4 binding region | 1002629-1006266 | 1029835-1034637 |
|   | Region from right ORF | 1006267-1009311 | 1034638-1036395 |
| 5 | Region from left ORF | 467209-469044 | 494073-495323 |
|   | Cse4 binding region | 469045-472074 | 495324-499155 |
|   | Region from right ORF | 472075-473740 | 499156-500591 |
| 6 | Region from left ORF | 975879-976872 | 993828-1003043 |
|   | Cse4 binding region | 976873-980625 | 1003044-1006692 |
|   | Region from right ORF | 980626-981389 | 1006693-1009568 |
| 7 | Region from left ORF | 423632-426037 | 425994-435239 |
|   | Cse4 binding region | 426038-428938 | 435240-438230 |
|   | Region from right ORF | 428939-430172 | 438231-439177 |

However, as mentioned earlier, the homologs of two genes adjacent to the CEN6 region in *C. albicans* are 80 kb apart in chromosome 6 of *C. dubliniensis* due to chromosome rearrangement (FIG. 4).

Since other CEN regions of *C. dubliniensis* are present in ORF-free regions that are greater than 3 kb, first all the intergenic regions, 3 kb or longer were identified, to find CEN6 in this 80 kb region. The ChIP-PCR analysis using specific primers from such regions delimited Cse4p-binding to a 3.6 kb region that is adjacent to the *C. albicans* Orf19.2124 homolog in *C. dubliniensis* (FIG. 3 and FIG. 6; not all ChIP data are shown). FIG. 6 shows relative enrichment profiles of CdCse4p in various *C. dubliniensis* chromosomes. CdCse4p-associated chromosome regions were enriched by ChIP using anti-Ca/CdCse4p antibodies. Specific primers corresponding to putative centromere regions of *C. dubliniensis* were used to PCR amplify DNA fragments (150 to 300 bp) located at specific intervals as indicated (Table 2). PCR was performed on total, immunoprecipitated (+Ab), and beads only control (−Ab) DNA fractions. Reverse images of ethidium bromide stained PCR products resolved on 1.5% agarose gels are aligned with respect to their chromosomal map position of each CEN region. The coordinates of primer locations are based on the present version (16 May, 2007) of the *Candida dubliniensis* genome database. Enrichment values are calculated by determining the intensities of (+Ab) minus (−Ab) signals divided by the total DNA signals and are normalized to a value of 1 for the same obtained using primers for a non-centromeric locus (CdLEU2). The intensity of each band was determined by using Quantity One 1-D Analysis Software (Bio-Rad, USA). Panels show the CdCse4p enrichment profiles on *C. dubliniensis* chromosomes at corresponding regions as indicated. Black arrows and grey arrows correspond to complete and incomplete ORFs, respectively, and indicate the direction of transcription.

Thus, CdCse4p-rich CEN regions and determined the boundaries of centromeric chromatin in all eight chromosomes in *C. dubliniensis* were successfully identified. It was also found that the relative distance of Cse4p-rich centromeric chromatin from orthologous neighboring ORFs is similar in both species in most cases (FIG. 1).

EXAMPLE 6

The Evolutionarily Conserved Kinetochore Protein CENP-C Homolog in *C. dubliniensis*, CdMif2p Binds Preferentially to CdCse4p-Associated DNA.

Proteins in the CENP-C family are shown to be associated with kinetochores in a large number of species. Using CaMif2p as the query sequence, the CENP-C homolog (CdMif2p) in *C. dubliniensis* was identified.

Homology Detection and Mutation Rate Measurement:

For homology detection, Sigma (version 1.1.3) and DIALIGN (version 2.2.1), to align ORF-free DNA sequences were used. Default parameters were used for both programs, but Sigma was given an auxiliary file of intergenic sequences from which to estimate a background model. Orthologous genes were aligned (at amino-acid level) with T-Coffee. Instances of the following seven codons where the first two positions were conserved in both species were examined: GTn (valine), TCn (serine), CCn (proline), ACn (threonine), GCn (alanine), CGn (arginine), GGn (glycine) (n=any nucleotide). Third position mutations here do not change the amino acid. (Leucine was ignored because of a variant codon in these species). A naïve count of mutation rates in the third position yields 0.27. Taken into consideration genome-wide bias for each codon, an upper-bound mutation rate of 0.42 was obtained.

For this analysis Sigma (version 1.1.3) (4) and DIALIGN 2 (5), to align ORF-free centromeric and other intergenic sequences were used. Default parameters were used for both programs, but Sigma was given an auxiliary file of intergenic sequence from which to estimate a background model. For protein-coding sequence, WU-BLAST 2.0 (tblastn) querying each annotated coding region of *C. albicans* against the chromosome sequences of *C. dubliniensis* was run. Parameters used were "filter=seg matrix=blosum62 hspsepQmax=1000 hspsepSmax=2000". Hits with a summed P-value of 1e-30 or less were identified as potential orthologs. Criteria for ortholog assignment were sequence similarity and synteny (requiring at least two common syntenous immediate neighbors out of four). This led to 2653 high-confidence predictions. These orthologous genes were aligned (at amino-acid level) with T-Coffee (6). Then the following seven amino acids were considered, when conserved, and coded by the indicated codons, in both species: GTn (valine), TCn (serine), CCn (proline), ACn (threonine), GCn (alanine), CGn (arginine), GGn (glycine) (n=any nucleotide). Other synonymous codons, if any, were ignored. Leucine was ignored because of a variant codon, CTG, that codes for serine in these species. A naïve count of mutation rates in the third position yields 0.27. This was improved on by considering the genome-wide bias for each codon, as follows: let the third-position conservation probability be q. Then if a third position nucleotide in *C. albicans* is b, in *C. dubliniensis* it stays b with probability q, and mutates with probability (1-q). If it mutates, it was assumed that the probability of the new nucleotide is drawn from the known codon bias. For each amino acid A, the individual mutation rate, $P(b_2/b_1,A)$ for third-position codon changing from $b_1$ in *C. albicans* to $b_2$ in *C. dubliniensis* was measured (the results are mathematically identical for evolution from a common ancestor), and solved for q; the weighted average of q for all amino acids and all pairs of observed third-position nucleotides $b_1$ and $b_2$ were then taken This works out to q=0.58, giving a mutation rate of 0.42. (Technically, this mutation rate is a slight overestimate, because a mutated $b_2$ from a distribution was drawn that includes $b_1$; but it is a credible upper bound.)

Results:

CdMif2p shows 77% identity and 5% similarity in 516 aa overlap. The CdMif2p codes for a 520-aa-long predicted protein in which the CENP-C box (aa residues 275-297) is 100% identical in *C. albicans* and *C. dubliniensis*. FIG. 7 shows the CENP-C homolog in *C. dubliniensis* (CdMif2p) is co-localized with CdCse4p. (A) Sequence alignment of CaMif2p and CdMif2p showing the conserved CENP-C block (red box) (B) Localization of CdMif2p at various stages of cell cycle in *C. dubliniensis*. (C) ChIP enrichment profiles of CdMif2p on chromosomes 1 and 3 in the strain CDM1 by determining the intensities of (+Ab) minus (−Ab) signals divided by the total DNA signals and are normalized to a value of 1 for the same obtained using primers for a non-centromeric locus (CdLEU2).

EXAMPLE 7

Construction of CDM1 Carrying C-Terminally TAP-Tagged CdMIF2.

A strain (CDM1) to express CdMif2p with a C-terminal tandem affinity purification (TAP) tag from its native promoter in the background of one wild-type copy of CdMIF2 was constructed.

Strains, Media and Transformation Procedures.

The *Candida dubliniensis* and *C. albicans* strains used in this study are listed in Table 4.

TABLE 4

| Yeast strains | Genotype | Source |
|---|---|---|
| *Candida dubliniensis* | | |
| Cd36 | Clinical isolate | 10 |
| CdUM4B | ura3D1::FRT/ura3D2::FRT | 8 |
| CdM1 | ura3D1::FRT/ura3D2::FRT MIF2/MIF2-TAP (URA3) | This study |
| *Candida albicans* | | |
| BWP17 | Δura3::imm434/Δura3::imm434 Δhis1::hisG/Δhis1::hisG Δarg4::hisG/Δarg4::hisG | 11 |
| CAKS1b | Δura3::imm434/Δura3::imm434 Δhis1::hisG/Δhis1::hisG Δarg4::hisG/Δarg4::hisG CSE4/cse4::hisG: URA: hisG | This study |
| CAKS2b | Δura3::imm434/Δura3::imm434 Δhis1::hisG/Δhis1::hisG Δarg4::hisG/Δarg4::hisG CSE4/cse4::hisG | This study |
| CAKS3b | Δura3::imm434/Δura3::imm434 Δhis1::hisG/Δhis1::hisG Δarg4::hisG/Δarg4::hisG cse4::PCK1pr-CSE4(URA3)/cse4::hisG | This study |

These strains were grown yeast extract/peptone/dextrose (YPD), yeast extract/peptone/succinate (YPS), or supplemented synthetic/dextrose (SD) minimal media at 30° C. as described. *C. albicans* and *C. dubliniensis* cells were transformed by standard techniques.

CdMIF2 downstream sequence (from +1634 to +2198 with respect to the start codon of CdMIF2) was PCR amplified with primer pair CdM3 (CGG GGT ACC GAT TGC AAG AAG TAC TAC ATA AGA GAG; SEQ ID NO: 133) and CdM4 (GCC CGA GCT CGC AGG TAA AAT TGT TCT TGA GGA GCC G; SEQ ID NO: 134) thereby introducing KpnI and SacI restriction sites (underlined). The resulting PCR amplified fragment was digested with KpnI and SacI and cloned into corresponding sites of pUC19 to generate pCDM1. TAP cassette along with CaURA3 gene was released from plasmid pPK335 (7) as BamHI-KpnI fragment and cloned into corresponding sites of pCDM1 to generate pCDM2. Subsequently CdMIF2 RF sequence from +1090 to +1548 was PCR amplified using primer pair CdM1 (ACG CGT CGA CCC CCC ACT GAT TAC GAT TAT GAA TCT GAT CC; SEQ ID NO: 135) and CdM2 (CAT GCC ATG GCC CAA TTC GTA TCG ATT TCT TCT GGT TTC; SEQ ID NO: 136) and cloned into pCDM2 as NcoI-SalI fragment to get pCDM3. Finally, a 2 kb amplicon was PCR amplified by the primer pair CdM1 and CdM4 using pCDM3 as the template. This PCR fragment was used to transform CdUM4B strain (8). The correct Ura+ transformant (CDM1) was identified by PCR analysis.

Result:

The subcellular localization patterns using polyclonal anti-Protein A antibodies in *C. dubliniensis* strain (CDM1) at various stages of cell cycle is very similar to those observed for CdCse4p (FIG. 7). Binding of TAP tagged CdMif2p in the strain CDM1 was analyzed by standard ChIP assays using anti-Protein A antibodies This experiment suggests that CdMif2p binds to the same 3 kb CdCse4p-rich region of two different chromosomes (Chromosome 1 and 3) in *C. dubliniensis*. Binding of two different evolutionarily conserved kinetochore proteins CdCse4p and CdMif2p at the same regions strongly implies that these regions are centromeric. (FIG. 3 and FIG. 7).

EXAMPLE 8

Comparative Sequence Analysis Between *C. albicans* and *C. dubliniensis* Reveals that Cse4p-Rich Centromere Regions are the Most Rapidly Evolving Loci of the Chromosome.

Pairwise alignment of CdCse4p-rich sequences on different chromosomes with one another reveals no homology. To compare orthologous CEN regions of *C. albicans*

TABLE 5

| | Cse4p-binding | Cse4p-binding (shuffled) | Pericentric | Intergenic |
|---|---|---|---|---|
| Total bases | 26836 | 26836 | 40280 | 593782 |
| Aligned (DIALIGN2) | 12440 (46%) | 11650 (43%) | 27684 (68%) | 530847 (89%) |
| Mutated (DIALIGN2) | 7624 (61%) | 7201 (62%) | 10229 (36%) | 154473 (29%) |
| Aligned (Sigma) | 0 | 0 | 15015 (37%) | 334363 (56%) |
| Mutated (Sigma) | 0 | 0 | 3323 (22%) | 57548 (17%) | and *C. dubliniensis*, pairwise alignments using Sigma and DIALIGN2 were performed. These programs assemble global alignments from significant gapless local alignments. Sigma detects no homology in Cse4p-binding regions. DIALIGN2, with default parameters, reports a little homology; but when nonorthologous sequence were compared, (namely, CEN sequences from non-matching chromosomes), it reports almost identical results (Table 5).

Table 5

In other words, it finds no homology beyond what it would with the "null hypothesis" of unrelated sequence. Similar results were obtained with other sequence alignment programs. It is concluded that there is no significant homology in the orthologous Cse4p-containing CEN regions in *C. albicans* and *C. dubliniensis*, even though the CEN regions are flanked by orthologous, syntenous ORFs. However, neighboring (pericentric) ORF-free regions, located between the Cse4p binding regions and CEN-adjacent ORFs, do exhibit a higher degree of homology compared to Cse4p-rich regions. Mutation rates were counted only in aligned blocks (ignoring insertions and deletions); DIALIGN2 aligns 68% of these regions, with a mutation rate of 36%, while Sigma aligns 38% of the regions, with a mutation rate of 22% in aligned regions. Much of the conservation occurs towards the outer ends of these regions, that is, near the bounding ORFs.

To estimate a "neutral" DNA mutation rate, 2,653 putative gene orthologs of *C. albicans* in *C. dubliniensis* were identified. For homology detection, Sigma (version 1.1.3) and DIALIGN (version 2.2.1), to align ORF-free DNA sequences were used. Default parameters were used for both programs, but Sigma was given an auxiliary file of intergenic sequences from which to estimate a background model. Orthologous genes were aligned (at amino-acid level) with T-Coffee. Instances of the following seven codons where the first two positions were conserved in both species were examined: GTn (valine), TCn (serine), CCn (proline), ACn (threonine), GCn (alanine), CGn (arginine), GGn (glycine) (n=any nucleotide). Third position mutations here do not change the amino acid. (Leucine was ignored because of a variant codon in these species). A naïve count of mutation rates in the third position yields 0.27. Taken into consideration genome-wide bias for each codon, an upper-bound mutation rate of 0.42 was obtained.

The genes with T-Coffee were aligned, and the synonymous mutation rates using seven codons that are "fully degenerate" in the third position was measured (the first two bases determine the coded amino acid). A naïve count of the third-position mutation rate yields 27%. Correcting for genome-wide codon biases yields 42%, an upper-boundary estimate for the "neutral" rate of DNA mutation between these two yeasts (see Materials and Methods). This rate corresponds to a pairwise conservation rate ("proximity") q=0.58, or a proximity to a common ancestor of 0.76. Tests on synthetic DNA sequence (as reported in 21) suggest that Sigma would easily align such sequence; therefore, it appears that CaCse4p-binding sequences (but not pericentric regions) have diverged faster than expected from the neutral point-mutation rate in these yeasts.

309 homologous intergenic regions were also identified in these species that were between 1000 and 5000 bp long (comparable in length with the Cse4p-binding regions). These regions were aligned with Sigma and DIALIGN2, and measured mutation rates in aligned regions only (ignoring insertions and deletions). Sigma aligned 56% of the input intergenic sequence, with a mutation rate of 17%; DIALIGN2 aligned 89% of the input sequence, with a mutation rate of 29%. This rate is less than our estimated neutral mutation rate of 42%, suggesting constraints on the evolution of intergenic DNA sequences. Although pericentric regions evolve slower than the neutral rate determined above, they have a smaller fraction of conserved blocks and a greater mutation rate than intergenic sequences.

Interestingly, despite the rapid divergence of CEN DNA sequences, the relative position of the CEN on each chromosome is conserved in all cases. FIG. 8 shows relative chromosomal positions of Cse4p-binding regions in *C. albicans* and *C. dubliniensis*. Red oval shows Cse4p-binding region.

The relative location of the Cse4p-rich centromeric chromatin in the ORF-free region is also similar in both species (FIG. 7). Although no homology was found among Cse4p-binding regions in matching chromosomes, some of the ORF-free pericentric regions in matching chromosomes have repeated segments, both within the same species and across the two species (FIG. 9).

FIG. 9 shows conserved blocks in the pericentric regions of various chromosomes of *C. dubliniensis* and *C. albicans*. The cyan dotted blocks represent the Cse4p-binding regions. DNA sequence stretches of various chromosomes having significant similarities (ClustalW scores above 80) are shown by colored arrows as indicated. The numbers on each chromosome represent their coordinates in respective genome database. The direction of the arrows represents the orientation of repeats. A BLAST search was done to identify the repeats flanking the CEN region against the *C. dubliniensis* genome database with *C. albicans* CEN flanking repeats as the query sequences (10). The inverted repeats were observed in the chromosomes R, 1 and 5 of *C. albicans* and *C. dubliniensis* (Table 6). The LTRs such as epsilon, zeta, episemon) are also shown.

TABLE 6

| Chr No. | Repeat | Coordinates in C. dubliniensis | % homology between the inverted repeats ¶ |
|---|---|---|---|
| R | IRR | 1720958-1721270 (D) | 100 |
|   | IRR | 1716158-1715822 (R) |   |
| 1 | IR1 | 1595932-1595989 (D) | 96 |
|   | IR1 | 1602853-1602907 (R) |   |
| 5 | IR5 | 493690-494369 (D) | 99 |
|   | IR5 | 500277-500974 (R) |   |

These results strongly suggest that factors other than Cse4p binding DNA sequences determine centromere identity in these species. The role of pericentric regions in determining centromere identity remains unclear.

Result:

Thus, the core CdCse4p-rich centromeric DNA sequences of all eight chromosomes of *C. dubliniensis*. Two important evolutionarily conserved kinetochore proteins, CdCse4p and CdMif2p are shown to be bound to these regions. Each of these CEN regions has unique and different DNA sequence composition without any strong sequence motifs or centromere-specific repeats that are common to all the eight centromeres, and has A-T content similar to that of the overall genome. In these respects they are remarkably similar to CEN regions of *C. albicans* (11, 12). Though genes flanking corresponding CENs in these species are syntenous, the Cse4p-binding regions show no significant sequence homology. They appear to have diverged faster than other intergenic sequence of similar length, and even faster than our best estimated neutral mutation rate for ORFs.

A study, based on computational analysis of centromere DNA sequences and kinetochore proteins of several organisms, indicates that point centromeres have probably derived from regional centromeres and appeared only once during evolution. The core Cse4p-rich regions of *C. albicans* and *C. dubliniensis* are intermediate in length between the point *S. cerevisiae*-like centromeres and the regional *S. pombe* centromeres. The characteristic features of point and regional yeast centromeres are the presence of consensus DNA sequence elements and repeats, respectively, organized around a nonhomologous core CenH3-rich region (CDEII and central core of *S. cerevisiae* and *S. pombe*, respectively). Both *C. albicans* and *C. dubliniensis* centromeres lack such conserved elements or repeats around their non-conserved core centromere regions.

Based on these features, it is proposed that these *Candida* species possess centromeres of an "intermediate" type between point and regional centromeres. On rare occasions, functional neocentromeres form at non-native loci in some organisms. However, neocentromere activation occurs only when the native centromere locus becomes non-functional. Therefore, native centromere sequences may have components that cause them to be preferred in forming functional centromeres. Despite sequence divergence, the location of the Cse4p-rich regions in orthologous regions of *C. albicans* and *C. dubliniensis* has been maintained for millions of years. Homology was also observed in orthologous pericentric regions in a pair-wise chromosome-specific analysis in these two species. Moreover, several short stretches of DNA sequences are found to be common in pericentric regions of some, but not all, *C. albicans* and *C. dubliniensis* chromosomes. Both in budding and fission yeasts, pericentric regions contain conserved elements that are important for CEN function. In the absence of any highly specific sequence motifs or repeats in these regions, it is possible that specific histone modifications at more conserved pericentric regions facilitate the formation of a specialized three-dimensional common structural scaffold that favors centromere formation in these *Candida* species. It is an enigma that, despite their conserved function and conserved neighboring orthologous regions, core centromeres evolve so rapidly in these closely related species. Satellite repeats, that constitute most of the *Arabidopsis* and *Orzya* centromeres, have been shown to be evolving rapidly. However, because of their repetitive nature, these plant centromeres are subject to several events such as mutation, recombination, deletion and translocation that may contribute to rapid change in centromere sequence. In the absence of any such highly repetitive sequences at core centromere regions of *C. albicans* and *C. dubliniensis*, such accelerated evolution is particularly striking. It is important to mention that a very recent report based on comparison of chromosome III of three closely related species of *Saccharomyces paradoxus* suggests that centromere seems to be the fastest evolving part in the chromosome. One possible mechanism for rapid evolution is error-prone replication of CEN DNA followed by inefficient repair. In fact, pausing of replication forks at the centromeres has been reported in *S. cerevisiae*. If a similar situation exists in *C. albicans* and *C. dubliniensis*, it is possible that core CEN regions are replicated by error-prone DNA polymerases, a situation similar to translesion DNA synthesis. Several studies reveal that centromeres function in a highly species-specific manner. Henikoff and colleagues proposed that rapid evolution of centromeric DNA and associated proteins may act as a driving force of speciation (1). The consequence of the rapid change in centromere sequence that was observed in these two closely related *Candida* species may contribute to generation of functional incompatibility of centromeres to facilitate speciation. To understand the mechanisms of centromere formation in the absence of specific DNA sequence cues, it will be important to identify more genetic and epigenetic factors that may contribute to the formation of specialized centromeric chromatin architecture.

LIST OF SUPPORTING REFERENCES

1. Thompson J-D, Higgins D-G, Gibson T-J (1994) CLUSTAL W: improving the sensitivity of progressive multiple sequence alignment through sequence weighting, position-specific gap penalties and weight matrix choice. *Nucleic Acids Res* 22:4673-4680.
2. Kumar S, Tamura K, Nei M (2004) MEGA3: integrated software for Molecular Evolutionary Genetics Analysis and sequence alignment. *Brief Bioinform* 5:150-163.
3. Gouet P, Courcelle E, Stuart D-I, Metoz F (1999) ESPript: analysis of multiple sequence alignments in PostScript. *Bioinformatics* 15:305-308.
4. Siddharthan R (2006) Sigma: multiple alignment of weakly-conserved non-coding DNA sequence. *BMC Bioinformatics* 7:143.
5. Morgenstern B (1999) DIALIGN2: improvement of the segment-to-segment approach to multiple sequence alignment. *Bioinformatics* 15:211-218.
6. Notredame C, Higgins D, Heringa J (2000) T-Coffee: A novel method for multiple sequence alignments. *J Mol Biol* 302: 205-217.
7. Corvey C et al. (2005) Carbon Source-dependent assembly of the Snf1p kinase complex in *Candida albicans*. *J Biol Chem* 280:25323-25330.
8. Staib P, Moran G-P, Sullivan D-J, Coleman D-C, Morschhauser J (2001) Isogenic strain construction and gene targeting in *Candida dubliniensis*. *J Bacteriol* 183:2859-2865.
9. Sanyal K, Baum M, Carbon J (2004) Centromeric DNA sequences in the pathogenic yeast *Candida albicans* are all different and unique. *Proc Natl Acad Sci USA* 101:11374-11379.
10. Sullivan D-J, Westerneng T-J, Haynes K-A, Bennett D-E, Coleman D-C(1995) *Candida dubliniensis* sp. boy.: phenotypic and molecular characterization of a novel species associated with oral candidosis in HIV-infected individuals. *Microbiology* 141:1507-1521.
11. Wilson R-B, Davis D & Mitchell A-P (1999) Rapid hypothesis testing with *Candida albicans* through gene disruption with short homology regions. *J Bacteriol* 181: 1868-1874.
12. Mishra P-K, Baum M, Carbon J (2007) Centromere size and position in *Candida albicans* are evolutionarily conserved independent of DNA sequence heterogeneity. *Mol Genet Genomics* 278:455-465.

What is claimed is:

1. A method of identifying presence of *Candida dubliniensis* in a sample having or suspected of having *Candida dubliniensis*, said method comprising:
   a) isolating at least one DNA sequence from the sample;
   b) providing a reaction mixture comprising the isolated DNA sequence, at least one primer sequence capable of amplifying a Cse4p binding region of *Candida dubliniensis*, a DNA polymerase and PCR amplification reagents, wherein the at least one primer sequence capable of amplifying a Cse4p binding region of *Candida dubliniensis* is selected from the group consisting of SEQ ID. NO: 13-21, 29-125 and 126;
   c) heating the reaction mixture to a first predetermined temperature for a first predetermined time, followed by reducing the temperature to a second predetermined temperature for a second predetermined time to cool the reaction mixture and allowing amplification of the DNA sequence; and
   d) observing the amplification product to identify presence of *Candida dubliniensis* in the sample.

2. The method of claim 1, wherein the at least one primer sequence comprises a pair of primers that are complementary to SEQ ID NO: 1, wherein a first primer is selected from the group consisting of SEQ ID NO: 13, 15, 17, 19 and 21 as a forward primer and a second primer is selected from the group consisting of SEQ ID NO: 14, 16, 18 and 20 as a corresponding reverse primer respectively.

3. The method of claim 1, wherein the at least one primer sequence comprises a pair of primers that are complementary to SEQ ID NO: 2, wherein a first primer is selected from the group consisting of SEQ ID NO: 29, 31, 33, 35, 37, 39 and 41 as a forward primer and a second primer is selected from the group consisting of SEQ ID NO: 30, 32, 34, 36, 38, 40 and 42 as a corresponding reverse primer respectively.

4. The method of claim 1, wherein the at least one primer sequence comprises a pair of primers that are complementary to SEQ ID NO: 3, wherein a first primer is selected from the group consisting of SEQ ID NO: 43, 45, 47, 49 and 51 as a forward primer and a second primer is selected from the group consisting of SEQ ID NO: 44, 46, 48, 50 and 52 as a corresponding reverse primer respectively.

5. The method of claim 1, wherein the at least one primer sequence comprises a pair of primers that are complementary to SEQ ID NO: 4, wherein a first primer is selected from the group consisting of SEQ ID NO: 53, 55, 57, 59, 61, 63, 65 and 67 as a forward primer and a second primer is selected from the group consisting of SEQ ID NO: 54, 56, 58, 60, 62, 64, 66 and 68 as a corresponding reverse primer respectively.

6. The method of claim 1, wherein the at least one primer sequence comprises a pair of primers that are complementary to SEQ ID NO: 5, wherein a first primer is selected from the group consisting of SEQ ID NO: 69, 71, 73, 75 and 77 as a forward primer and a second primer is selected from the group consisting of SEQ ID NO: 70, 72, 74, 76 and 78 as a corresponding reverse primer respectively.

7. The method of claim 1, wherein the at least one primer sequence comprises a pair of primers that are complementary to SEQ ID NO: 6, wherein a first primer is selected from the group consisting of SEQ ID NO: 79, 81, 83, 85, 87, 89, 91 and 93 as a forward primer and a second primer is selected from the group consisting of SEQ ID NO: 80, 82, 84, 86, 88, 90, 92 and 94 as a corresponding reverse primer respectively.

8. The method of claim 1, wherein the at least one primer sequence comprises a pair of primers that are complementary to SEQ ID NO: 7, wherein a first primer is selected from the group consisting of SEQ ID NO: 95, 97, 99, 101, 103, 105, 107, 109 and 111 as a forward primer and a second primer is selected from the group consisting of SEQ ID NO: 96, 98, 100, 102, 104, 106, 108, 110 and 112 as a corresponding reverse primer respectively.

9. The method of claim 1, wherein the at least one primer sequence comprises a pair of primers that are complementary to SEQ ID NO: 8, wherein a first primer is selected from the group consisting of SEQ ID NO: 114, 116, 118, 120, 122, 123 and 126 as a forward primer and a second primer is selected from the group consisting of SEQ ID NO: 113, 115, 117, 119, 121, 124 and 125 as a corresponding reverse primer respectively.

10. A method of distinguishing *Candida dubliniensis* from *Candida albicans* in a sample, said method comprising steps of:
   (a) isolating DNA sequence from the sample;
   (b) providing a reaction mixture comprising the isolated DNA sequence, at least one primer sequence capable of amplifying a Cse4p binding region of *Candida dubliniensis*, a DNA polymerase and PCR amplification reagents, wherein the at least one primer sequence capable of amplifying a Cse4p binding region of *Candida dubliniensis* is selected from the group consisting of SEQ ID. NO: 13-21, 29-125 and 126;
   (c) heating the reaction mixture to a first predetermined temperature for a first predetermined time, followed by reducing the temperature to a second predetermined temperature for a second predetermined time to cool the reaction mixture and allowing amplification of the DNA sequence; and (d) observing the amplification product to distinguish *Candida dubliniensis* from *Candida albicans* in the sample.

11. The method of claim 10, wherein the at least one primer sequence comprises a pair of primers that are complementary to SEQ ID NO: 1, wherein a first primer is selected from the group consisting of SEQ ID NO: 13, 15, 17, 19 and 21 as a forward primer and a second primer is selected from the group consisting of SEQ ID NO: 14, 16, 18 and 20 as a corresponding reverse primer respectively.

12. The method of claim 10, wherein the at least one primer sequence comprises a pair of primers that are complementary to SEQ ID NO: 2, wherein a first primer is selected from the group consisting of SEQ ID NO: 29, 31, 33, 35, 37, 39 and 41 as a forward primer and a second primer is selected from the group consisting of SEQ ID NO: 30, 32, 34, 36, 38, 40 and 42 as a corresponding reverse primer respectively.

13. The method of claim 10, wherein the at least one primer sequence comprises a pair of primers that are complementary to SEQ ID NO: 3, wherein a first primer is selected from the group consisting of SEQ ID NO: 43, 45, 47, 49 and 51 as a forward primer and a second primer is selected from the group consisting of SEQ ID NO: 44, 46, 48, 50 and 52 as a corresponding reverse primer respectively.

14. The method of claim 10, wherein the at least one primer sequence comprises a pair of primers that are complementary to SEQ ID NO: 4, wherein a first primer is selected from the group consisting of SEQ ID NO: 53, 55, 57, 59, 61, 63, 65 and 67 as a forward primer and a second primer is selected from the group consisting of SEQ ID NO: 54, 56, 58, 60, 62, 64, 66 and 68 as a corresponding reverse primer respectively.

15. The method of claim 10, wherein the at least one primer sequence comprises a pair of primers that are complementary to SEQ ID NO: 5, wherein a first primer is selected from the group consisting of SEQ ID NO: 69, 71, 73, 75 and 77 as a forward primer and a second primer is selected from the group consisting of SEQ ID NO: 70, 72, 74, 76 and 78 as a corresponding reverse primer respectively.

16. The method of claim 10, wherein the at least one primer sequence comprises a pair of primers that are complementary to SEQ ID NO: 6, wherein a first primer is selected from the group consisting of SEQ ID NO: 79, 81, 83, 85, 87, 89, 91 and 93 as a forward primer and a second primer is selected from the group consisting of SEQ ID NO: 80, 82, 84, 86, 88, 90, 92 and 94 as a corresponding reverse primer respectively.

17. The method of claim 10, wherein the at least one primer sequence comprises a pair of primers that are complementary to SEQ ID NO: 7, wherein a first primer is selected from the group consisting of SEQ ID NO: 95, 97, 99, 101, 103, 105, 107, 109 and 111 as a forward primer and a second primer is selected from the group consisting of SEQ ID NO: 96, 98, 100, 102, 104, 106, 108, 110 and 112 as a corresponding reverse primer respectively.

18. The method of claim 10, wherein the at least one primer sequence comprises a pair of primers that are complementary to SEQ ID NO: 8, wherein a first primer is selected from the group consisting of SEQ ID NO: 114, 116, 118, 120, 122, 123 and 126 as a forward primer and a second primer is selected from the group consisting of SEQ ID NO: 113, 115, 117, 119, 121, 124 and 125 as a corresponding reverse primer respectively.

\* \* \* \* \*